(12) United States Patent
Heath

(10) Patent No.: US 8,260,413 B2
(45) Date of Patent: *Sep. 4, 2012

(54) RESUSCITATION AND LIFE SUPPORT SYSTEM, METHOD AND APPARATUS

(75) Inventor: Roger Lee Heath, Tempe, AZ (US)

(73) Assignee: Roger Lee Heath, Tempe, AZ (US)

( * ) Notice: Subject to any disclaimer, the term of this patent is extended or adjusted under 35 U.S.C. 154(b) by 167 days.

This patent is subject to a terminal disclaimer.

(21) Appl. No.: 12/686,064

(22) Filed: Jan. 12, 2010

(65) Prior Publication Data

US 2010/0114218 A1  May 6, 2010

Related U.S. Application Data

(63) Continuation of application No. 11/235,005, filed on Sep. 26, 2005, now Pat. No. 7,672,720.

(60) Provisional application No. 60/612,741, filed on Sep. 24, 2004, provisional application No. 60/614,627, filed on Sep. 29, 2004, provisional application No. 60/614,876, filed on Sep. 29, 2004, provisional application No. 60/615,137, filed on Oct. 1, 2004, provisional application No. 60/616,777, filed on Oct. 6, 2004, provisional application No. 60/616,693, filed on Oct. 7, 2004, provisional application No. 60/617,360, filed on Oct. 8, 2004.

(51) Int. Cl.
  *A61N 1/00* (2006.01)
(52) U.S. Cl. .......................................................... 607/5
(58) Field of Classification Search .................... 607/5
  See application file for complete search history.

(56) References Cited

U.S. PATENT DOCUMENTS

| | | | |
|---|---|---|---|
| 3,258,013 A | 6/1966 | Druz | |
| 4,928,674 A | 5/1990 | Halperin et al. | |
| 5,531,764 A | 7/1996 | Adams et al. | |
| 5,593,426 A * | 1/1997 | Morgan et al. | ..................... 607/5 |
| 5,974,339 A | 10/1999 | Baker, Jr. et al. | |
| 6,083,248 A | 7/2000 | Thompson | |
| 6,093,248 A | 7/2000 | Kohl et al. | |
| 6,128,531 A | 10/2000 | Campbell-Smith | |
| 6,292,692 B1 | 9/2001 | Skelton et al. | |
| 6,356,785 B1 | 3/2002 | Snyder et al. | |
| 2004/0143297 A1 | 7/2004 | Ramsey, III | |
| 2005/0048121 A1 | 3/2005 | East et al. | |

* cited by examiner

*Primary Examiner* — George Manuel
(74) *Attorney, Agent, or Firm* — Adam K. Sacharoff

(57) ABSTRACT

A method of applying electrotherapy to the heart of a patient includes positioning electrodes in communication with the heart of the patient; monitoring the patient's heart to determine if its fibrillating; and providing a first signal with a current generator to the heart through the electrodes in response to an indication that the heart is fibrillating. The first stimulus signal reduces the amount of fibrillation.

19 Claims, 30 Drawing Sheets

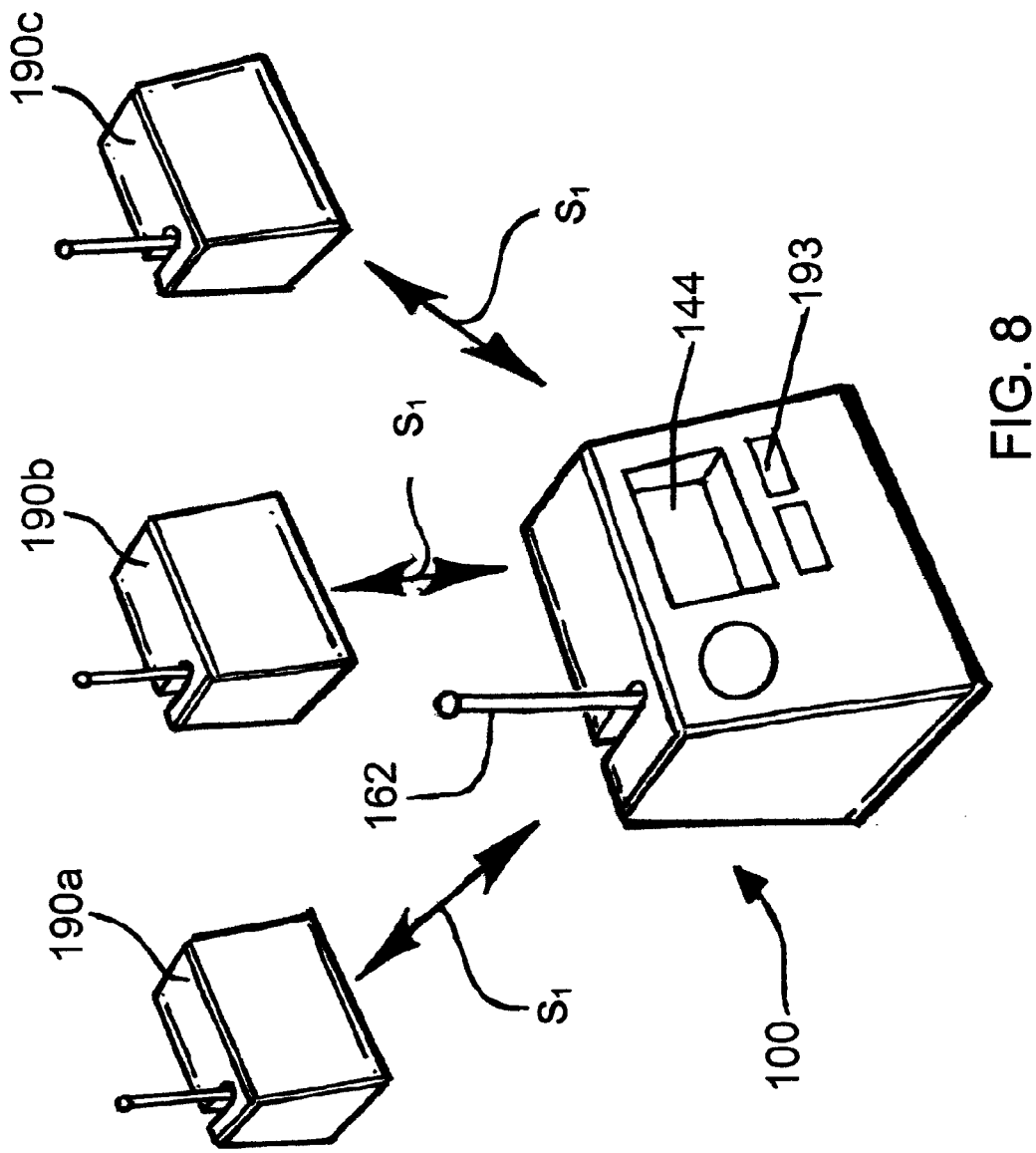

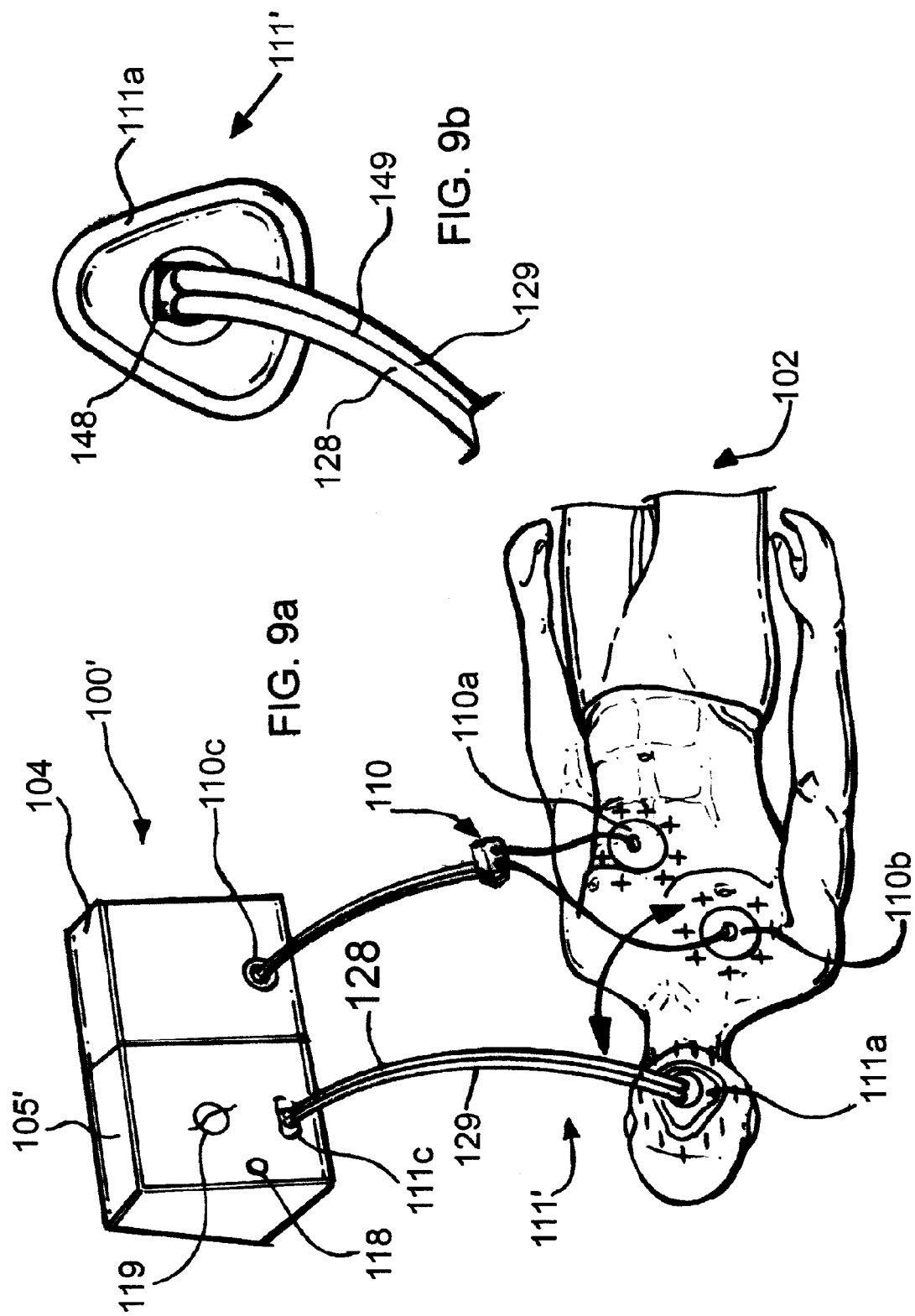

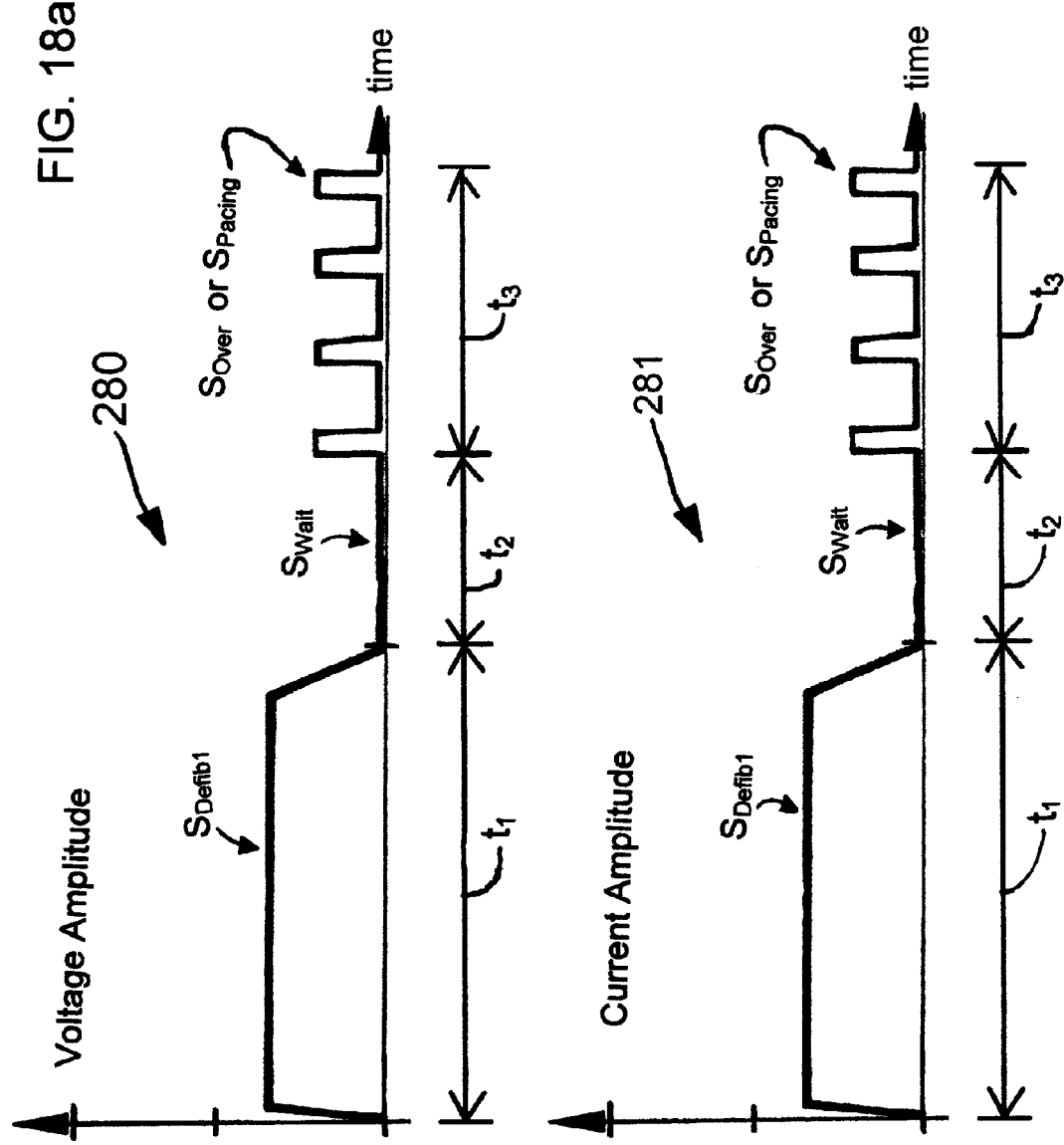

RESUSCITATION AND LIFE SUPPORT SYSTEM, METHOD AND APPARATUS

CROSS REFERENCE TO RELATED APPLICATIONS

The present application is a continuation application of U.S. Nonprovisional application Ser. No. 11/235,005, filed Sep. 26, 2005, which claims benefit to the following U.S. Provisional Applications: (1) Defibrillation and Pacing Waveform, Ser. No. 60/612,741; Filed Sep. 24, 2004; (2) Resuscitator with Patient Finder, Ser. No. 60/614,627; Filed Sep. 29, 2004; (3) Electrode Pads, Ser. No. 60/614,876; Filed Sep. 29, 2004; (4) Modular Resuscitation System, Ser. No. 60/615,137; Filed Oct. 1, 2004; (5) Resuscitator with Ion Agent Delivery System, Ser. No. 60/616,777; Filed Oct. 6, 2004; (6) Resuscitator with Telecommunication System, Ser. No. 60/616,693; Filed Oct. 7, 2004; and (7) Resuscitator Visual Status Display and Instruction System, Ser. No. 60/617,360; Filed Oct. 8, 2004.

FIELD OF THE INVENTION

The present invention relates to surgery and, more particularly, to portable resuscitation devices.

BACKGROUND OF THE INVENTION

Some medical systems include resuscitation and life support systems. A resuscitation system can include a defibrillator and a life support system can include pacemakers, ventilators, and a circulation support system. Prior art portable resuscitation systems are mostly directed to automatic external defibrillators (AEDs) and circulation resuscitators. These systems generally include portable airway resuscitators and portable breathing resuscitators. However, for emergency personal to carry and handle all of these devices separately is not efficient. Further, time lost by the emergency personal in gathering all of these devices and carrying them to a patient is critical. Therefore, there is a need to provide a single modular resuscitator system that is portable and includes modular devices that are directed to airway, breathing, and circulation (ABC) resuscitation. It is also preferred to save costs by having the ability to adapt to new modular devices as specific technology evolves.

In addition, 80% of cardiac arrest occurs outside the hospital often leading to critical time being wasted by emergency personal trying to locate the patient and/or communicate with an emergency center and/or healthcare facility and/or provider. For communications between the rescuer or the patient and the emergency center and/or healthcare facility and/or provider separate devices such as wireless or wire line telecommunication units are well known and used. However, if neither is readily available, the patient or rescuer is left by themselves. The ability to communicate reliable information quickly back and forth between everyone is extremely important but not readily provided. Hence, there is a need to solve these problems by providing a modular and integrated telecommunication unit to each resuscitator device.

In the difficulty of locating the patient, the emergency personal has nothing to rely on other than information given to them by a 911 center or if the patient or a third party with the patient is able to communicate their location. The prior art is devoid of a resuscitator with any ability to communicate a patient location. This can be invaluable when a patient is in distress or arrest and when the time for finding the victim can make all the difference in saving his or her life. This can also provide tremendous aid to rescue personnel and reduce the confusion and time required in finding victims, a costly issue for their time as well as potentially the patient's life.

It is known that resuscitators, and especially ventilators, do not exist to maintain ABC resuscitation procedures. As such, an integrated device and protocol program which coordinates the ventilator with defibrillation, cardiac (or heart) pacing, CPR, etc. does not exist. However, such devices are needed to enhance the speed and success of all these procedures. For example, defibrillation should occur near the peak of respiratory expiration and is more successful when done this way. There is also a need to improve oxygen delivery to oxygen starved tissues. This increases the ability to save the life of a cardiac arrest victim, or at least sustain the victim until advanced care arrives increasing the probability of ultimate survival. A system is needed in all emergency and prolonged ventilation procedures for providing simple, safe, and reliable ventilation. The prior art does recognize the need to introduce various chemical agents or regimens into a cardiac arrest patient. Some of these agents are introduced via the trachea and airway through aerosols or nebulizations. The prior art does not provide for any additional ionizing techniques to accelerate the introduction of the agent into the patient. There is a need for an ion infusion system that improves oxygen and agent or regimen delivery to oxygen starved tissues. There is also a need to more rapidly introduce agents via the airway, trachea, and lungs into a cardiac arrest victim. It is accepted that the rapid infusion of oxygen and epinephrine, etc. into the bloodstream will help save the heart and brain of an arrest victim.

The use of resuscitators has long been reserved to highly trained personnel. With the federal government endorsing the use of resuscitators, such as AEDs, by the general public, the ability to train and/or instruct the general populace with the proper placement of monitoring, defibrillation, and/or pacing pads, ventilation masks, or airways, and the general use of resuscitation procedures has now become vital. There is a need to make the use of resuscitators easy for the average person so that he or she can use the resuscitator effectively. Currently, resuscitators come with complicated instruction manuals and confusing displays. Visual and voice prompt resuscitators do exist in the marketplace, however, the images and displays are difficult to understand. In order to cut manufacturing costs, the use of liquid crystal displays has been reduced or eliminated. While the resuscitators may display illustrations or instructions, the user must interpret these quickly. Vital time is passing for the critical patient while the user takes time to figure this out. There is a need to provide a simple, less confusing, inexpensive, and clearer display of information that guides the user and eases the proper operation and use of the resuscitator.

Defibrillators commonly provide high amplitude electrical pulses or defibrillator shocks with relatively short durations. Typical high amplitude pulses are generally 1000 volts (V) to 3000 V and range in duration from about 10 milliseconds (ms) to 40 ms. High amplitude electrical pulses may damage heart tissue and short duration electrical pulses may not adequately halt chaotic depolarizing waves of the heart. Further, high amplitude defibrillators tend to be higher in both size and cost. In the new retail markets for AEDs, size and cost are very critical. Today's defibrillators are also not electrically designed to be "constant current" shock devices. Hence, the electrical characteristics or outcome of each shock is highly unpredictable. There is a need to produce smaller and less costly defibrillators with more predictable electrical characteristics.

Overdrive heart pacing is a technique, similar to defibrillation, of over-riding heart 'chaos' (tachyarrhythmia or fibrillation) whereby many small amplitude pacing pulses are delivered in rapid succession. After defibrillator shocks, sometimes the patient is converted to heart standstill (asystole). This could be an electrical problem with the heart and these victims are commonly provided with Cardio Pulmonary Resuscitation (CPR) instead of being paced right away. The fibrillating heart operates like it has irregular tissue depolarizing waves through it at about 600 ms to 800 ms duration, in which case fibrillation never exists in the first place and only tachycardia (very rapid heartbeats) exists, or multiple waves of tachycardia. This also suggests that short duration defibrillator pulses are not long enough in commercial defibrillators. This means that patients may be overdrive paced instead of defibrillated. This is because the treatment primarily prescribed for tachyarrhythmia is overdrive pacing or synchronized countershock, and defibrillation may be an improper interpretation and treatment.

Resuscitators typically include a pair electrode pads and there are two well accepted placements for them. In a first instance, the two pads are placed on the anterior or front portion of the patient's chest, known as anterior-anterior placement. In the first instance, one of the pads is placed near the lower left of the patient's thorax near the heart's apex and the other one is positioned on the upper right thorax to the right of the patient's sternum. In a second instance, a first electrode pad is positioned at the common apex position and the second electrode pad is positioned on the posterior or back of the patient behind the heart. In the second instance, the positioning of the electrode pads is typically called anterior-posterior placement, if these same pads are used for external cardiac pacing, the anterior-posterior electrode position is commonly preferred. However, no such resuscitator system exists for allowing the addition of a posterior electrode if anterior-anterior electrodes are already on the patient and then automatically switching to the preferred anterior-posterior mode for defibrillation and pacing. Accordingly, there is a need in the art for an improved resuscitation system incorporating these features.

SUMMARY OF THE INVENTION

The present invention provides a medical system that provides life support and resuscitation functions for a patient. The life support and resuscitation functions are typically implemented using airway, breathing, and circulation protocols. These functions, which generally include defibrillation, pacing, and/or ventilation, are provided in an automated and coordinated fashion so that patient survivability rates are increased. Further, these functions can be provided to the patient with fewer people. The medical system is also portable and can be easily carried from one location to another quickly and efficiently, which decreases the patient response time and increases patient survival rates.

These and other features, aspects, and advantages of the present invention will become better understood with reference to the following drawings, description, and claims.

BRIEF DESCRIPTION OF THE DRAWINGS

FIG. 1b shows several different arrangements for the medical system of FIG. 1a;

FIGS. 1c and 1d show simplified block diagrams of the medical system of FIG. 1a;

FIG. 4 is a simplified back view of another embodiment of a top portion of the defibrillator of FIG. 3a;

FIG. 8 is a simplified perspective view of a medical system in communication with emergency centers, in accordance with the present invention;

FIG. 9a is a simplified perspective view of an embodiment of a medical system which provides chemical agent delivery, in accordance with the present invention;

FIG. 9b is a simplified front view of air-way breathing circuit showing a mask with a contact, in accordance with the present invention;

FIG. 10b is a simplified side view of a patient connected to the medical system of FIG. 10a;

FIG. 11b is a simplified side view of a portion of the display of FIG. 11a;

FIGS. 18a and 18b are simplified graphs of various waveforms in accordance with the present invention.

DETAILED DESCRIPTION OF THE EMBODIMENTS

Figure 1A:
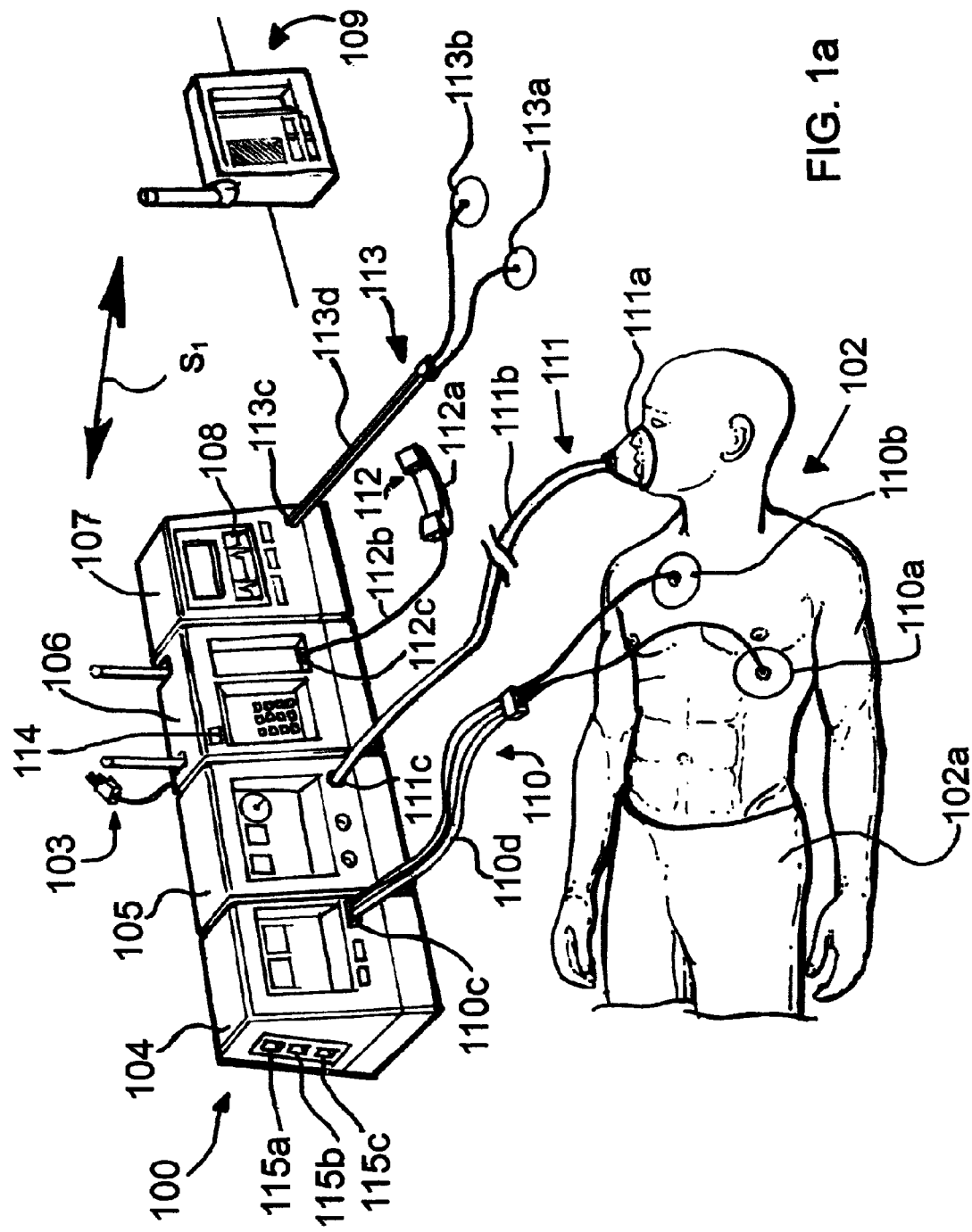
FIG. 1a is a simplified perspective view of a medical system in accordance with the present invention.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

The present invention improves upon known medical methods, procedures, and devices, some of which are disclosed in prior U.S. patents. See, for example U.S. Pat. Nos. 4,419,998; 4,494,552; and 4,850,356, the entirety of which are herein incorporated by reference. See also U.S. Pat. Nos. 4,102,332; 4,786,277; 4,890,177; 4,941,469; 6,095,138; 6,611,708; 6,668,192; 6,694,187; 6,697,671; 6,848,444; and 6,937,150, the entirety of which are herein incorporated by reference.

FIG. 1a is a simplified perspective view of a medical system 100 in accordance with the present invention. System 100 provides life support and/or ABC resuscitation functions for a patient 102. Medical system 100 has several advantages with one being that it provides for the more efficient management of patient 102. The management of patient 102 is more efficient because system 100 provides automated and coordinated resuscitation and life support functions. These functions include defibrillation, pacing, chemical delivery, chemical diffusion, and/or ventilation. System 100 provides these functions in an automated fashion so that fewer people are needed. System 100 also increases the chances of patient survival by coordinating procedures handled by separate modules (e.g. ventilation, AED, monitoring, communications, etc.). System 100 is also portable and can be easily carried from one location to another quickly and efficiently, which decreases the patient response time and increases patient survival rates.

Medical system 100 includes separate modules which are movable between attached (FIG. 1A) and detached conditions (FIG. 2). The separate modules communicate with each other and share information and resources, as will be discussed in more detail below. The sharing of information and resources optimizes and accelerates procedures and protocols typically implemented using these modules separately. In this embodiment, these modules include a defibrillator 104, ventilator 105, communication system 106, and monitor 107. In other embodiments, however, system 100 can include different combinations of these modules.

Figure 1B:
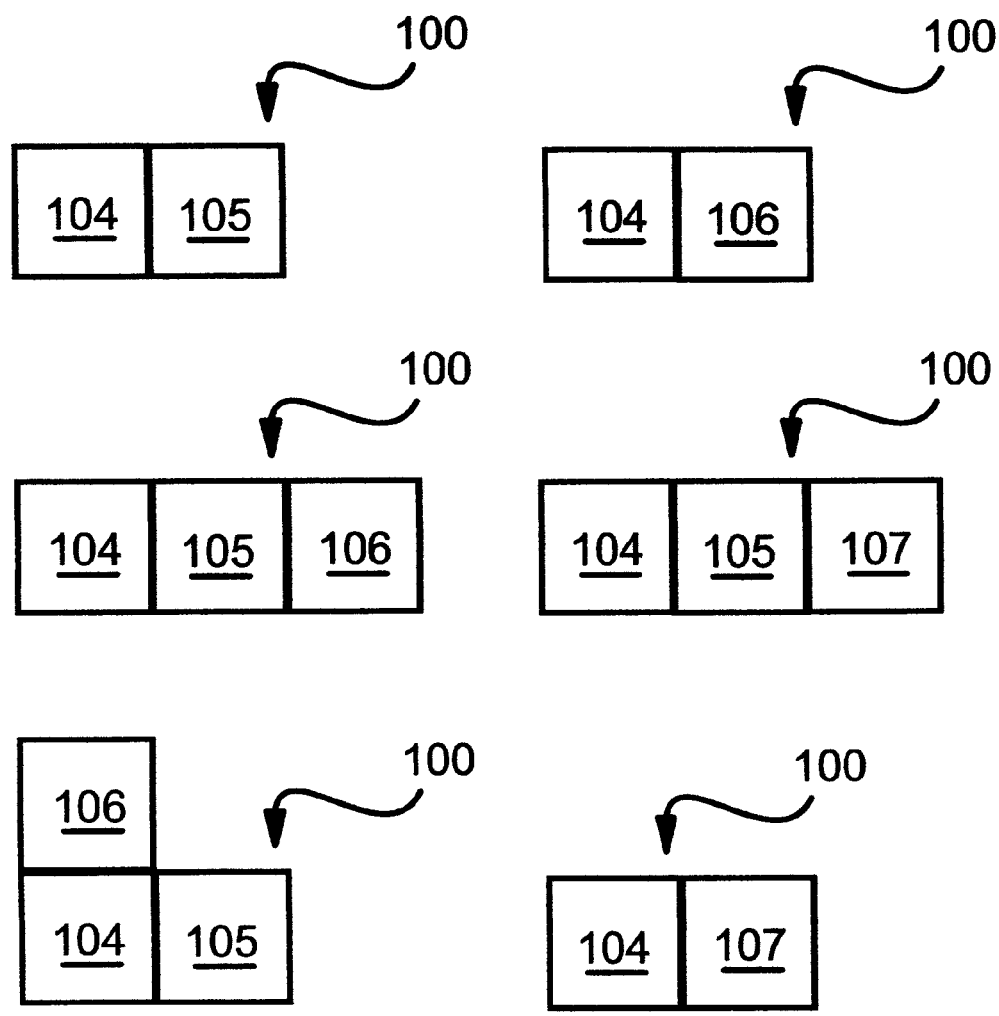

FIG. 1b shows several different arrangements for system 100. In one embodiment, system 100 includes defibrillator 104 and ventilator 105. In another embodiment, system 100 includes defibrillator 104 and communication system 106. In another embodiment, system 100 includes defibrillator 104, ventilator 105, and communication system 106. In still another embodiment, system 100 includes defibrillator 104, ventilator 105, and monitor 107. In one embodiment, system 100 includes defibrillator 104 and monitor 107. In accordance with the invention, at least two of the defibrillator 104, ventilator 105, communication system 106, and monitor 107 are moveable between attached and detached conditions, as shown in FIG. 2. It is preferred, however, that system 100 include communication system 106, for reasons to be discussed below.

Defibrillator 104 is in communication with the heart of patient 102 through an electrode system 110 coupled to anterior 102a of patient 102. Defibrillator 104 provides many different functions, such as circulatory resuscitation and/or pacing, for patient 102 as needed. Defibrillator 104 can be of many different types, but is an automatic external defibrillator (AED) in this example. These types of defibrillators are made by many different manufacturers known in the art. Electrode system 110 can be of many different types. In this example, electrode system 110 includes a cable 110d coupled to electrode pads 110a and 110b at an end and port 110c at an opposed end. Port 110c is an output of defibrillator 104 which outputs defibrillation and/or pacing signals therethrough. Electrode pads 110a and 110b are coupled to the thorax of patient 102 so that they are in communication with the heart of patient 102. In this way, defibrillator 102 provides circulatory resuscitation and/or pacing for patient 102.

Ventilator 105 is in communication with patient 102 through a breathing circuit 111. Ventilator 105 provides many different functions, such as breathing and oxygenation of the blood of patient 102, as needed. Ventilator 105 can be of many different types, but is an Airway Pressure Release Ventilation (APRV) type ventilator in this example. Further, breathing circuit 111 can be of many different types known in the art. In this example, it includes a air mask 111a coupled to the mouth of patient 102 and a hose 111b with an end coupled to air mask 111a and an opposed end coupled to ventilator 105 through a port 111c. Port 111c is an output of ventilator 105 which outputs oxygen and/or air therethrough. Mask 111a is held to patient 102 in a manner well-known in the art so that ventilator 105 provides breathing and oxygenation of the blood of patient 102.

Monitor 107 is in communication with patient 102 through an electrode system 113. In this embodiment, monitor 107 includes a display 108 and provides many different functions, such sensing, monitoring, and/or displaying the vital signs of patient 102. The vital signs generally include the heart rate and breathing rate of patient 102 and are displayed by display 108 as an Electrocardiogram (ECG) so that the user of system 100 can see them. The user is generally a medically trained responder. In some examples, the vital signs are flowed to communication system 106, as will be discussed in more detail below. Monitor 107 can be of many different types, but is an ECG monitor in this example. These types of monitors are made by many different manufacturers known in the art.

Electrode system 113 can be of many different types known in the art. In this example, electrode system 113 includes a cable 113d coupled to monitor pads 113a and 113b at an end and port 113c at an opposed end. Electrode system 113 typically includes more than two electrode pads 113a and 113b, but only two are shown here for simplicity. Port 113c is an input of monitor 107 which flows monitoring signals therethrough. Electrode pads 113a and 113b are coupled to anterior 102a so that they are in communication with the heart of patient 102. In this way, monitor 107 monitors and/or displays the vital signs of patient 102. Monitor 107 can have multiple sensors coupled to patient 102 to display multiple vital signs, such as pulse and blood gas information. In this way, system 100 is made more useful for trained medical personnel, such as paramedics and doctors.

Communication system 106 provides communications with an external communication system 109 by flowing a signal $S_1$ between systems 100 and 109. Signal $S_1$ generally includes voice and/or data information. Further, external communication system 109 generally includes an emergency services communication system, a computer system, and/or a public or private telephone system, among others. External communication system 109 can be used by many different people and organizations, such as a family member, family doctor, hospital, fire department, ambulance service, emergency medical team, a doctor's office, 911 dispatch center, or public and private medical personnel.

In accordance with the invention, communication system 106 allows system 100 to transmit and receive voice and data signals at the same time and at different times. System 106 can include communication components known in the art to reduce costs. Communications systems 106 and 109 can communicate with each other in many different ways. In this example, they communicate with each other through a wireless link, although in other examples the communication can be through a land line, WiFi link, or combinations thereof.

In this example, communication system 106 includes a voice/data communication system 112, which is a land line, although it can be wireless or hands free in other examples. In this example, system 112 includes a telephone 112a coupled to system 106 through a cable 112b. Cable 112b has an end connected to telephone 112a and an oppose end connected to a port 112c of system 106.

In some embodiments, voice/data communication system 112 provides "hands-free" operation, which is useful when patient 102 is unable to hold telephone 112a. Patient 102 may be unable to hold telephone 112a In many different situations, such as if they are in too much pain, too weak, or unconscious. In these "hands-free" embodiments, system 112 includes a speaker phone or other communication devices which provides "hands-free" operation.

As mentioned above, communication system 106 allows system 100 to transmit and receive voice and data signals at the same time and at different times. In this embodiment, system 106 does this by providing multiple communication links which transmit and receive data and voice information. The multiple communications links can be provided in several different ways, such as by a phone system, radio system, WiFi link, or combinations thereof. WiFi allows data and voice to be transmitted over the same link without significant interference between the voice and data signals, so in some examples a single communication link can be used. Some WiFi links can do this because they use a technology called voice over Internet protocol (VOIP).

It should be noted that it is preferred that communication system 106 provide multiple communication links for communication redundancy in case one communication link is not available. A communication link may not be available for several different reasons, such as a hardware or software problem or failure, the weather, etc. With this in mind, some embodiments can include multiple WiFi links, one of which is used as a primary voice/data communication link and the other of which is used as a backup voice/data communication link in case the primary communication link fails or is otherwise unavailable.

In this example, however, the data and voice information are flowed on separate links by system 106. This feature is advantageous because it can be used with a third party medical service, with or without 911 dispatch, or to flow data independently on a second link while using the first link to flow voice data. Hence, the user can use system 100 to call a third party medical service instead of a 911 dispatch center. This is desirable if the user does not want to call the 911 dispatch center because the dispatch center will often send the fire department, police, and/or ambulance service in response, which can cause unwanted attention and embarrassment. This is also advantageous for the patient's medical service or provider because the medical service or provider can be called first and provided with more control over where the patient goes. In most situations, the hospital is in control of this instead. Further, the patient will often feel more comfortable talking with his or her medical service or provider first because of their prior established relationship. This may also lower medical legal risks, because the service can simultaneously view the medical history of patient 102 to determine the appropriate safe medical treatment. This can also be conveyed in the "conference call" to the medical personnel assisting patient 102.

Another advantage of having multiple communication links is that a remotely located person can communicate with patient 102 by voice and also receive data regarding their status. This data often includes the vital signs of patient 102. If the remotely located person determines that it is beneficial for patient 102 to receive more assistance, then the remotely located person can use the second link provided by system 106 to call for more assistance.

Another advantage of providing multiple communication links with system 106 is that a conference call can be initiated using system 100. One situation where this is useful is when it is desired to provide a communication link between the patient, a third party, 911 dispatch, and medical personnel, for example.

In accordance with the invention, defibrillator 104, ventilator 105, communication system 106, and monitor 104 are moveable between attached and detached positions. The detached position is better seen in FIG. 2a, which is a simplified perspective view of system 100 showing defibrillator 104 detached from communication system 106. The modules in system 100 operate together as a unit when in their attached condition. One way the modules operate together is by sharing their power supplies, as will be discussed in more detail below. In one embodiment, each module has its own power supply which is connected to the power supply of each adjacent module. In this way, if one power supply fails, then that module can receive power from an adjacent module's power supply. This feature provides power system redundancy and reduces the likelihood that a power supply failure will interfere with the life support and resuscitation functions of system 100.

Figure 2A:
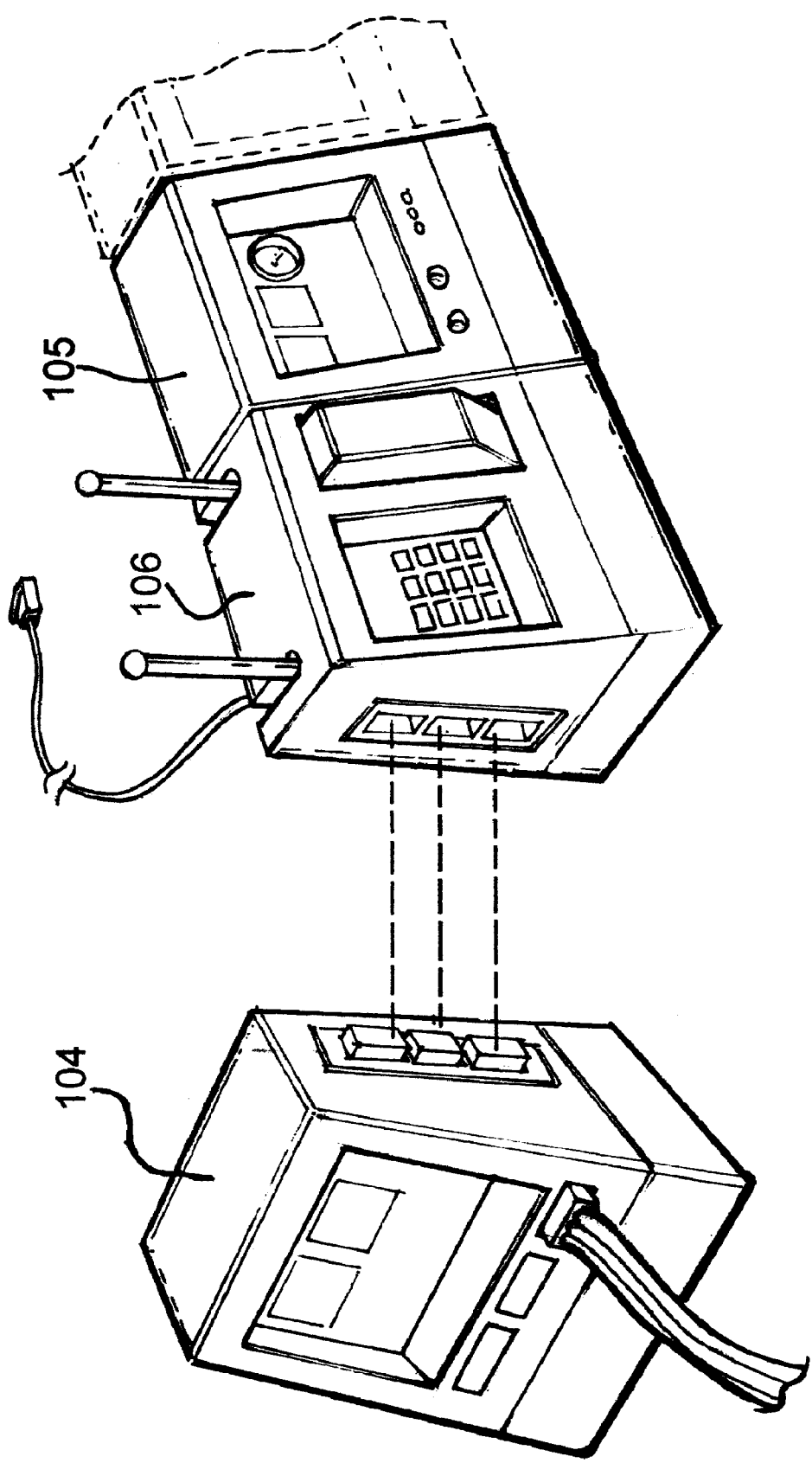
FIG. 2a shows the medical system of FIG. 1a in a detached condition.
Figure 2B:
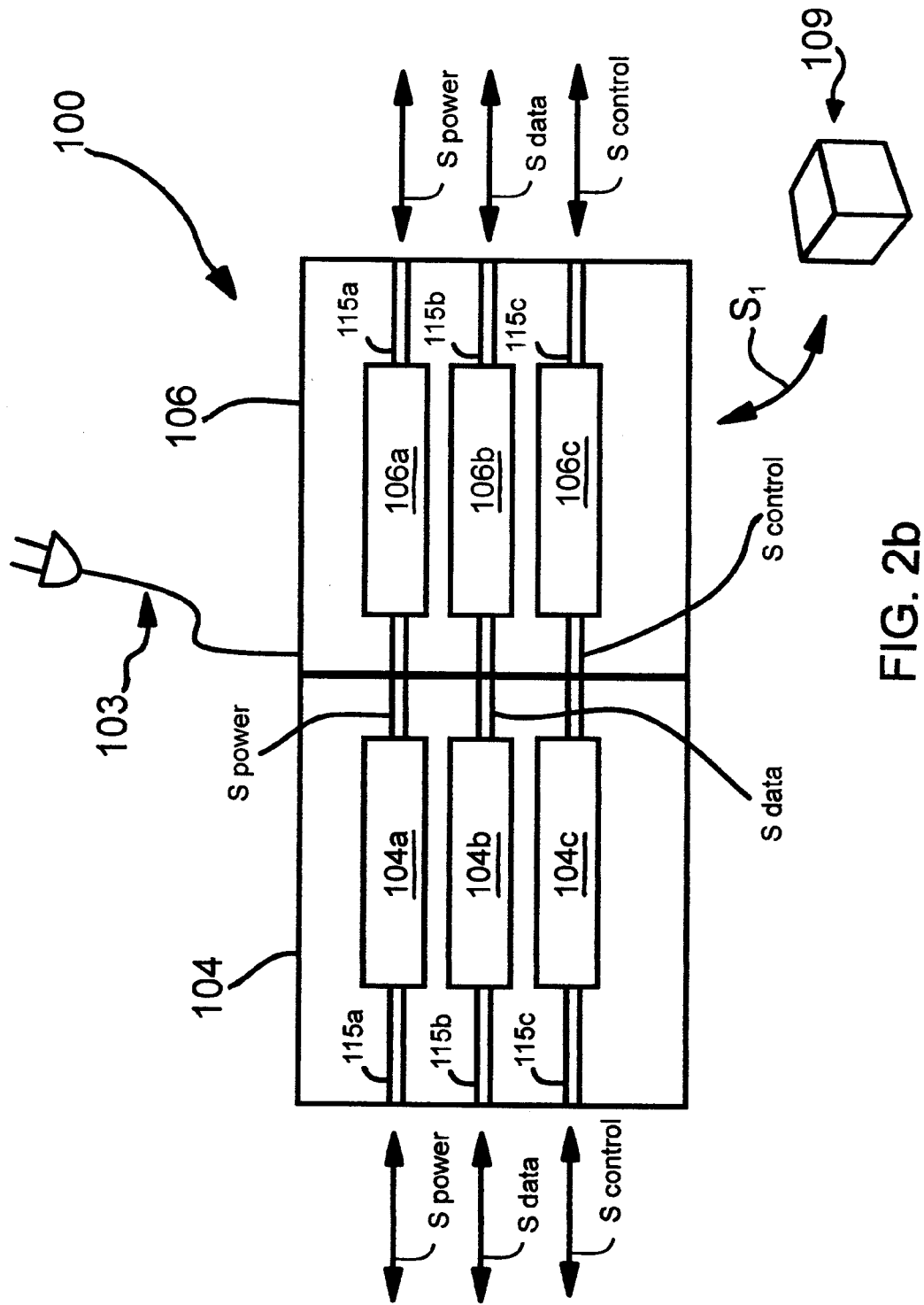
FIG. 2b is a simplified block diagram of an embodiment of the medical system of FIG. 1c which includes a defibrillator in an attached condition with a communication system.

FIG. 2b is a simplified block diagram of an embodiment of system 100 which includes defibrillator 104 in an attached condition with communication system 106. In accordance with the invention, adjacent modules included in system 100 are in communication with each other so that signals can flow between them. The signals can include voice and/or data information and power signals. In this embodiment, defibrillator 104 includes a power system 104a, data system 104b, control system 104c, and control system 104d. Similarly, communication system 106 includes a power system 106a, data system 106b, control system 106c, and control system 106d. Power system 104a, data system 104b, and control system 104c are in communication with power system 106a, data system 106b, and control system 106c, respectively.

The adjacent modules in system 100 are connected together with conductive lines, which can be of many different types. The conductive lines extend through 'both sides' so each module can be positioned next to an adjacent module on either side. In other examples, the conductive lines can extend through the top or bottom of a module so that they can be stacked on top of each other too and still be able to communicate.

In this embodiment, the conductive lines can be of several different types, such as wires or cables. Plugs, connectors, and/or sockets can also be included in system 100 to facilitate the flow of signals between defibrillator 104 and communication system 106. In this embodiment, power systems 104a and 106a are in communication with each other through a conductive line 115a, data systems 104b and 106b are in communication with each other through a conductive line 115b. Control systems 104c and 106c are in communication with each other through a conductive line 115c.

Control systems 104d and 106d include control circuitry which controls the operation of defibrillator 104 and communication system 106, respectively. In other examples, however, the flow of signals between the modules is wireless. The wireless flow of signals can be made with cellular or WiFi, for example. In other examples, the flow of signals can even be done optically, such as with an infrared signal.

In this embodiment, power systems 104a and 106a are battery power systems. Systems 104a and 106a can include rechargeable batteries, such as a fuel cell. Each module in system 100 includes a power system that is coupled to the power system of each adjacent module. This provides power system redundancy so that each module in system 100 will operate if the power system of one module fails. This is because the module with the failed power system can get power from an adjacent module's power system that is still working.

This also provides common power charging. Common power charging is provided because only one module in system 100 needs to be plugged into an external power source, such as an outlet, to charge it and the other modules it is connected to. System 100 is typically plugged into the external power source using a power cord 103. In this example, power cord 103 is coupled to power system 106a of communication system 106, but it could be coupled to the power systems of the other modules included in medical system 100 if desired. In still other examples, multiple power cords can be included in system 100 to provide power cord redundancy in case one power cord or its corresponding power system fails. This is shown in FIG. 2a where a separate power cord is coupled to defibrillator 104 and communication system 106.

Conductive line 115b provides for communications of data signals between defibrillator 104 and communication system 106. An advantage of this is that data can be received and provided by defibrillator 106 in response to a data signal $S_{Data}$. The data received can include ECG data and the data provided can include voice data. Signal $S_{Data}$ is typically flowed between system 106 and an external communication system 109.

Conductive line 115c provides for communications of control signals between defibrillator 104 and communication system 106. An advantage of this is that the operation of defibrillator 104 is controllable in response to signal $S_{Control}$ flowing between defibrillator 104 and communication system 106. Signal $S_{Control}$ is typically received by system 106 from an external communication system (not shown). An advantage of this is that defibrillation protocols can be adjusted in response to signal $S_{Control}$.

An advantage of system 100 is that the modules can be customized for the particular user since they can be detached from each other and rearranged. This feature provides several benefits. One benefit is that system 100 can be used to provide Advanced Life Support (ALS) and Basic Life Support (BLS). BLS typically includes protocols for the layperson or public safety first responders and ALS includes more advanced protocols for use by medically trained personnel.

System 100 can be customized which is useful for the end user. For example, if the end user includes trained medical personnel, then system 100 is preferably customized to provide ALS features. If the end user is a layperson, then system 100 is preferably customized to provide BLS features. This is useful because it is anticipated that more advanced ALS protocols, such as Automatic Transport Ventilator (ATV) procedures, will be approved for the layperson in the future, so system 100 can be upgraded to provide them without the need to purchase a whole new system. This saves the end user money because the system can be purchased in parts. Another advantage is that some end users can only afford to purchase one or two modules for system 100. System 100 allows them to do this with the option of buying more modules at a later date when more money becomes available. These new modules can be attached to the modules previously purchased.

Another benefit is that system 100 can be arranged by the end user according to his or her personal preference. For example, the various modules can be positioned on the left side of system 100 or the right side. This is useful for medical personnel who generally use more than one system 100 at different locations. They can change the configuration of system 100 to one that they are used to so that they can use system 100 in a more efficient and coordinated manner. This is also useful for right handed people verses left handed people because they often feel more comfortable using a particular setup which favors their dominant hand. It should be noted that the arrangement of the modules included in system 100 is different in FIGS. 1a and 2a. In FIG. 1a, ventilator 105 is next to defibrillator 104 and in FIG. 2a communication system 106 is next to defibrillator 104.

Being able to buy the modules separately allows the end user to choose how much they want to pay for the system. If one has a communication module that is cellular and the end user wants to use WiFi instead, then they only need to replace the communications module with the desired one and the other modules are left the same. This upgrading method saves the end user money. Thus, the user may avoid having to buy or replace the entire system because it is very expensive. Instead, one may selectively replace modules as desired at a much lower cost. This is of particular importance to municipal emergency providers or responders who may have limited funds due to budgeting constraints.

Figure 1C:
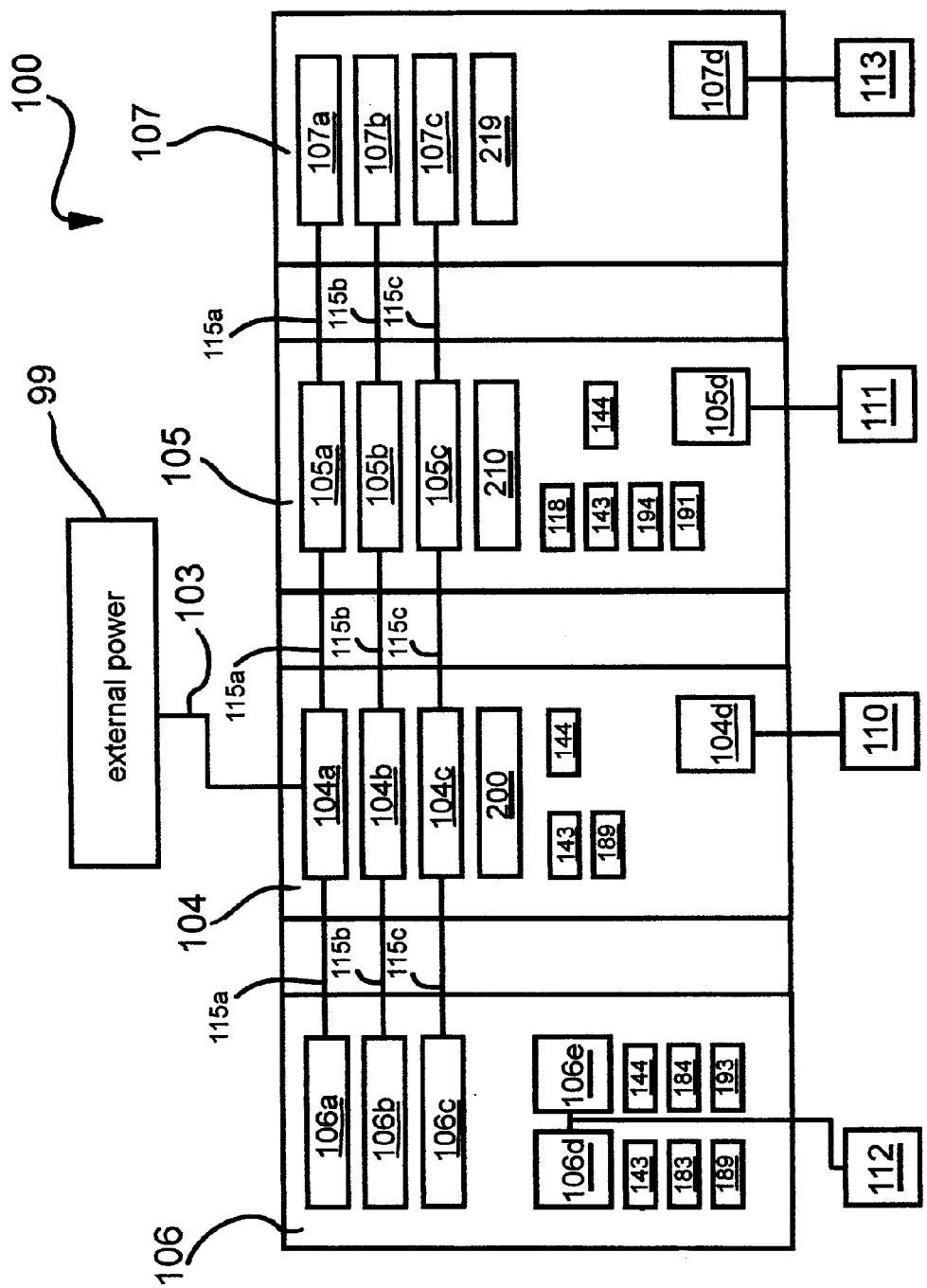
Figure 1D:
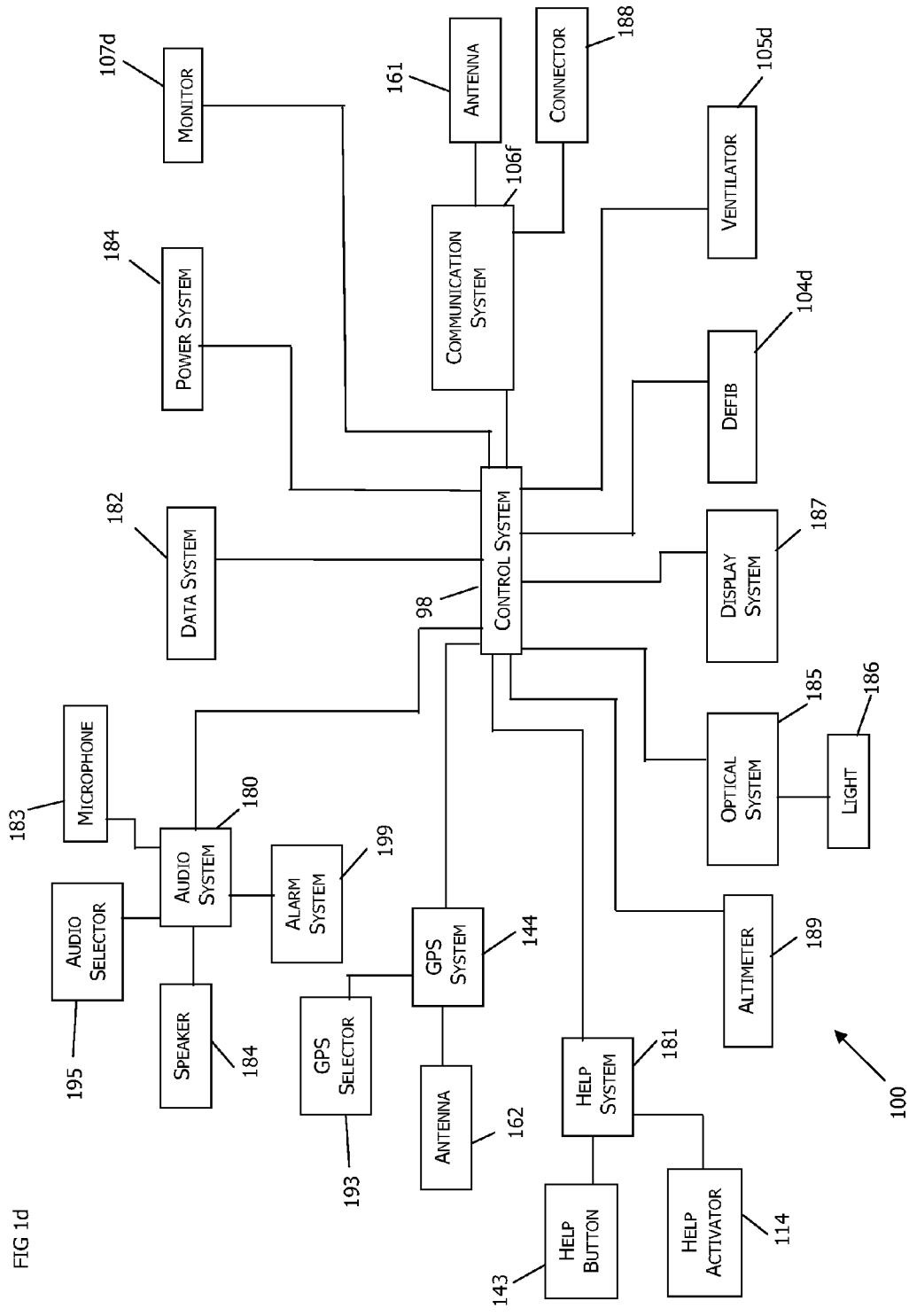

FIG. 1c is a simplified block diagram of one embodiment of the electrical system of system 100 showing the physical placement of electronic components included therein, FIG. 1d is a simplified block diagram of one embodiment of the electrical system of system 100 showing the electrical connections of electronic components included therein.

Figure 11A:
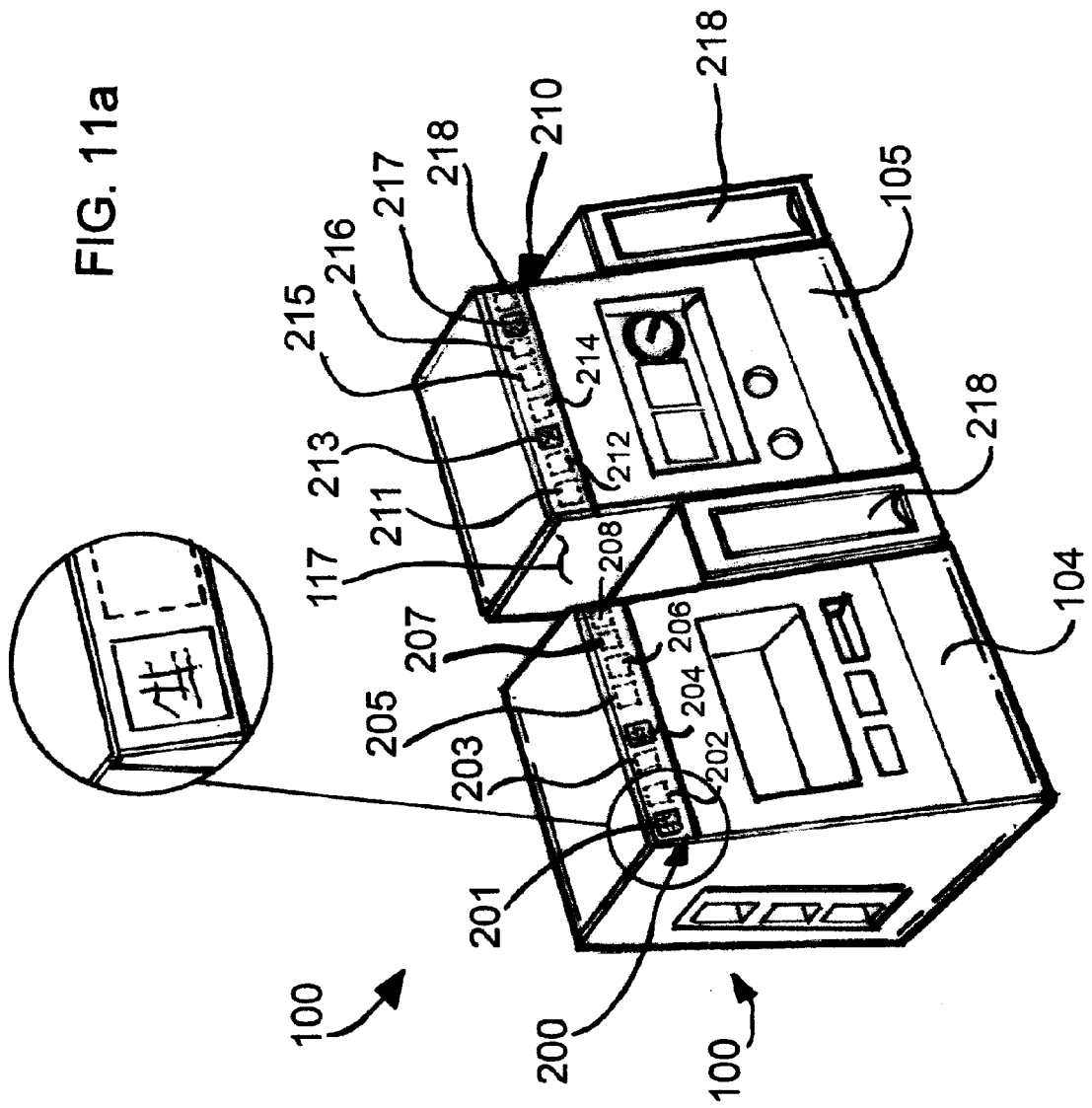
FIG. 11a is a simplified perspective view of the medical system of FIG. 1a with a defibrillator and a ventilator and displays, in accordance with the present invention.
Figure 11B:
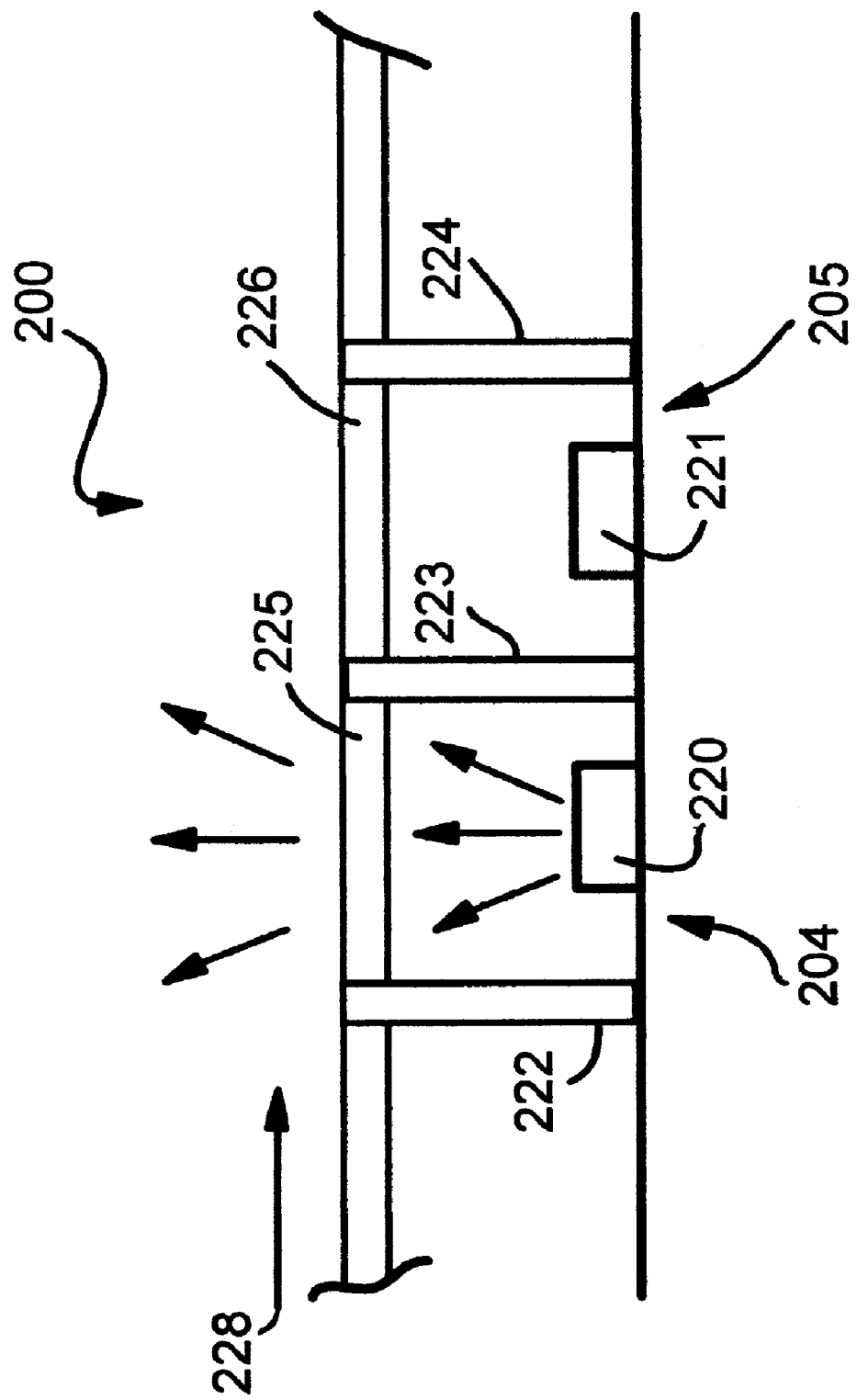

In this embodiment, defibrillator 104 includes a power circuit 104a, a data circuit 104b, and a control circuit 104c. Defibrillator 104 also includes a display 200 (FIGS. 11a and 11b). Electrode system 110 is coupled to a defibrillator circuit 104d. In this example, power circuit 104a is connected to an external power source 99.

In this embodiment, ventilator 105 includes a power circuit 105a, a data circuit 105b, and a control circuit 105c. Defibrillator 104 also includes a display 210 (FIGS. 11a and 11b). Ventilator 105 includes an air-way breathing circuit 105d connected to air-way breathing circuit 111. Ventilator 105 also includes a selector 118 (FIG. 9a) and an absorber 191. System 105 further includes a chemical source 194.

Figure 7:
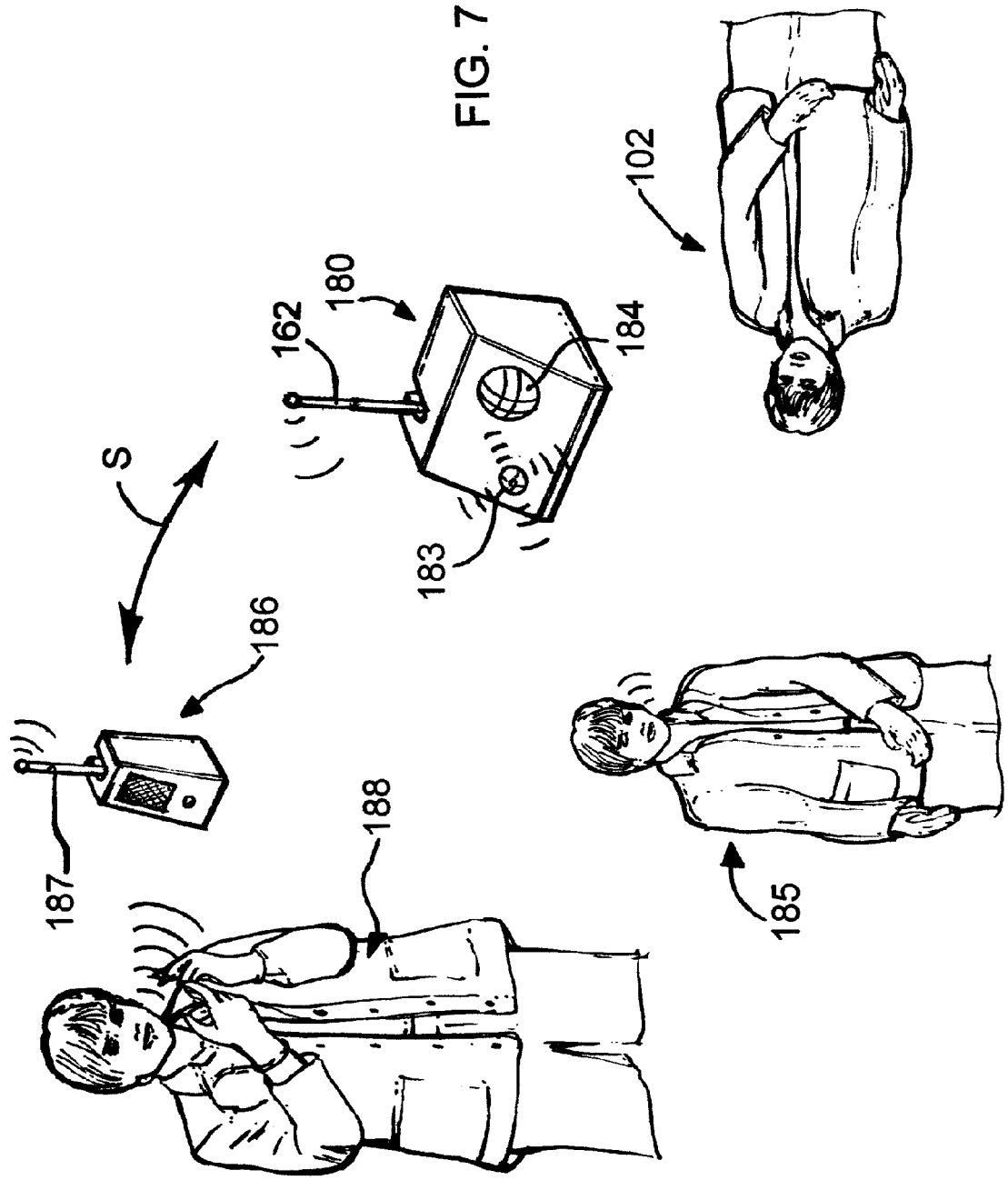
FIG. 7 is a simplified perspective view of a medical system in accordance with the present invention.

In this embodiment, communication system 106 includes a power circuit 106a, a data circuit 106b, and a control circuit 106c. Communication system 106 also includes communication modules 106d and 106e, a global positioning system (GPS) system 144 (FIG. 5a), help selector 143 (FIG. 5a), microphone 183 (FIG. 7), and speaker 184 (FIG. 7). Communication modules 106d and 106e are connected to phone system 112.

In this embodiment, monitor 107 includes a power circuit 107a, a data circuit 107b, and a control circuit 107c. Monitor 107 also includes a monitor circuit 107d connected to electrode system 113. Monitor 107 also includes a display 219 similar to displays 200 and 210 discussed in more detail with FIGS. 11a and 11b.

In accordance with the invention, power circuits 106a and 104a are connected together with conductive line 115a. Power circuits 104a and 105a are connected together with conductive line 115a. Power circuits 105a and 107a are connected together with conductive line 115a.

In accordance with the invention, data circuits 106b and 104b are connected together with conductive line 115b. Data circuits 104*b* and 105*b* are connected together with conductive line 115*b*. Data circuits 105*b* and 107*b* are connected together with conductive line 115*b*.

In accordance with the invention, control circuits 106*c* and 104*c* are connected together with conductive line 115*c*. Control circuits 104*c* and 105*c* are connected together with conductive line 115*c*. Control circuits 105*c* and 107*c* are connected together with conductive line 115*c*.

In this embodiment and as shown in FIG. 1*d*, power circuits 104*a*-107*a* operate together as a common power system 184, data circuits 104*b*-107*b* operate together as a common data system 182, and control circuits 104*c*-107*c* operate together as a common control system 98. Systems 182 and 184 are connected to system 98 as shown. Similarly, communication modules 106*d* and 106*e* operate together as a common communication system 106, which is also connected to control system 98. Selector 143 is connected to control system 98 through a help system 181. A GPS antenna 162 is connected to control system 98 through GPS system 144. Speaker 84 and microphone 183 are connected to control system 98 through an audio system 180. Defibrillation circuit 104*d*, ventilator circuit 105*d*, and monitor circuit 107*d* are also connected to control system 98. Antenna 161 is connected to communication system 106. A light 186 is connected to control system 98 through an optical control system 185. A display system 187 is connected to control system 98. Display system 187 includes displays 200, 210, and 219.

In this example, system 100 includes an alarm system 199 so that the patient can actuate locator selector 193 in several different situations. These situations are generally emergency situations, such as a fire and a heart attack, among others, and the activation of locator selector is desirable so that system 100 can be located faster. In accordance with the invention, system 100 includes control circuitry that activates locator selector 193 in response to a received locator signal. This is useful when system 100 is stored at a location where it is not visible so that a user looking for it can find it faster. In some examples, alarm system 199 can be a dual switch.

System 100 transmits an audio or visual signal in response to the locator signal. The audio signal is provided by a speaker similar to speaker 184 and the visual signal is provides by an optical indicators, such as a light 186. In this way, system 100 can be located faster. This is useful during an emergency because patient survival rates often increase if system 100 is brought to them faster. A concern is that the responder will spend time looking for the AED, fire extinguisher, etc. We want to decrease this time. Change arrest to medical emergency. The visual signal can be a blinking light, for example, and can have a color chosen to get the responders attention. One color that is generally used in an emergency is red.

Communications system 106 can be programmed to be language specific for the region required. It may sound off, with a computerized voice, the GPS location and situation information, even if the caller is disabled so the patient or victim needing help is located quickly.

Data system 182 can store many different types of information. A patient's age and/or weight can be stored by the user, to permit system 100 to adjust the amplitude and time of the defibrillation and pacing signals provided by defibrillator 104. This can also be accomplished by a common rotary control for both stimulation current and respiration.

Similarly, system 100 can select the flow rate and other parameters for respiration provide by ventilator 105. If pain is experienced by patient 102, then the air composition can be adjusted by adding nitrous oxide, oxygen anesthesia or both. Monitor 107 can monitor ECG and work "on demand" if patient 102 arrests during the use of system 100. In some examples, integrated into monitor 107 is the ability to test by finger or ear plethysmographic techniques or impedance cardiography to verify sufficient circulation in patient 102 and to automatically adjust stimulation-defibrillation current. System 100 can also be utilized at the bedside in ICCU units or by medical personnel. System 100 can also be used in or during surgery and complex medical procedures. System 100 preferably keeps patient 102 alive for a longer time period until help arrives. In other embodiments, the present invention could include matching instruments connected through a special interface to use.

The various systems in system 100 generally include electronic circuitry known in the art. This circuitry can provide many different functions, such as control, data processing, memory storage, etc.

Global positioning system (GPS) 144 provides the location of system 100. GPS system can be positioned at different places of system 100. Here, GPS system is integrated with communication system 106, but it could be integrated with defibrillator 104, ventilator 105, and monitor 107 in others.

Audio system 180 can be positioned at different places in system 100. Here, audio system 180 is integrated with communication system 106, but it could be integrated with defibrillator 104, ventilator 105, and monitor 107 in others. In one example, audio system 180 provides a sound in response to the location of system 100 as indicated by GPS system 144. In another example, audio system 180 provides a sound in response to the vital signs of patient 102 as indicated by monitor 107. In some embodiments, system 180 includes an audio alarm 192.

If ventilator 105 is connected to an audio system, such as audio system 180, then it can provide sounds to indicate warnings. The warning can be of several different types, such as a problem with patient 102 or it can indicate that system 104*d* is about to provide a defibrillation signal. If system 105 is connected to an audio system, such as audio system 180, then it can provide sounds to indicate a problem with system 105. The problem can be of several different types, such as a hardware failure or a gas leak. It should be noted that audio system 180 generally is coupled to one or more speakers and that speakers tend to be heavy and expensive. As a result, it is preferable to limit their numbers so that system 100 is cost effective and portable.

Speaker 184 or another speaker in system 100 is capable of providing prerecorded audio sounds to alert nearby people or responders of the location of patient 102.

Control system 98 can include a processor to detect the status of patient 102. This can be done in several different ways, such as through circuit 104*d* and/or 107*d*. This is usually done by monitoring the vital signs of patient 102. The prerecorded message can be provided through speaker 184 in response to an indication that there is a problem with patient 102. The problem can be cardiac arrest, for example.

In this embodiment, system 100 includes a help activator 114. Help activator 114 can be positioned at different places in system 100 and can include many different electronic devices, such as a button or switch. Here, help activator 114 is with communication system 106. Help activator 114 is useful so that patient 102 or another person can activate it to request assistance. In accordance with the invention, a signal from activator 114 is flowed to control system 98 through help system 181 in response to its activation. Help activator 114 can also be activated to turn off the various sounds provided by audio system 180.

System 100 includes an altimeter 189. Altimeter 189 can be positioned in many different locations within system 100. Altimeter 189 is preferably positioned within defibrillator 104. However, in this example, communication system 106 also includes altimeter 189. Altimeter 189 is connected to control circuit 98. In accordance with the invention, altimeter 189 and GPS system 144 preferably operate together to provide the longitude, latitude, and elevation of system 100.

In this embodiment, audio system 180 includes recording circuitry coupled to microphone 183 to record and store sounds, such as voices. The recording circuitry also preferably records and stores event data and/or information, such as ECG signals. In some examples, the recording circuitry records and stores communications flowed through communication system 106f. An advantage of the recording circuitry is that voice, communication, and/or data information can be recorded so that they can be reviewed later. This feature is useful for quality control reasons, medical malpractice problems, and/or to determine why the patient died or did not die. In this way, system 100 operates as an event recorder.

The present invention may also include a 'HYPER' or 'Hyperventilate' button that would trigger a single sequence or cycle of hyperventilating a patient in desperate need of oxygenization. This could be automated if the ventilator is informed that the patient is in cardiac arrest by an interconnected defibrillator or monitor, or though its own means of detecting that the patient is in arrest, or lacking oxygen. This is normally done manually and not automatically. The main goal is to increase the time the patient has before paramedics arrive. For a prolonged period. Response time. Patient access time. Decrease the time it takes for medical emergency services to arrive. This generally includes firefighters, paramedics, and ambulance, or other health personnel.

The operation of the defibrillator 104, ventilator 105, and/or monitor 107 is controllable in response to the signal flowing between communication system 106 and systems 109. In accordance with the invention, the protocols are adjustable in response to several different indications.

The protocols are adjustable in response to a signal flowing between the first and second communication system. In accordance with the invention, centralized programmable protocols are loaded into system 100 so that each device can be operated to provide coordinated resuscitation procedures. The protocols can be changed remotely and they can be changed because of communications between units.

A protocol is typically a procedure for performing a task, such as defibrillation and ventilation. The protocols are typically provided by medical personnel. The protocols are generally different for different medical equipment manufacturers. It is noted that the protocols for system 100 can be adjusted by preloading them into it. The protocols can be loaded into system 100 in many different ways. For example, they can be loaded using a memory disk known in the art, such as a floppy disk and a compact disk. They can also be loaded using a wireless or land line connection or through a USB port.

In conventional AEDs applications, it is most often first to be determined, in most protocols, that the patient has stopped breathing before recommendation of application of the AED electrode pads is allowed. Application of the ventilator can determine if the patient is breathing by pressure variations or sensors placed in or near the airway of the connected patient. Then, the ventilator can indicate the patient is not breathing, which can then 'justify' application of the AED. Following these lines it is contemplated herein to provide a second method of determining if a patient is breathing through the application of a self-adhesive stethoscope that may be applied to the chest of the victim or located within the airway of the victim. Sounds may then be amplified by an audio amplifier in the ventilator and 'broadcast' by a speaker in it. These sounds would also be transmitted to a connected communications unit so medical personal at a remote location could hear the patients breathing or chest sounds.

In FIG. 1a, the protocols are implemented by the remote control of a computer system 109. In other examples, a central protocol system is built into system 100 in case it is unable to contact computer system 109. In addition, a user of computer system 109 can override the protocols by sending appropriate commands to system 100. System 100 can record patient data (heart rate, etc.), communication signals, changes in protocols, etc. in an independent or centralized fashion to consolidate information for further care and critical review or quality improvement. The units in system 100 respond to each other in response to the protocols and then types of units interconnected together. Protocols are generally predefined programs or settings and are often based on the recommendations of emergency health professionals and/or health care organizations, such as the American Heart Association (AHA).

As mentioned, the protocols are programmed to function in accordance to predefined times and selected procedures. In one example, defibrillator 104 is programmed to determine the patient's expiration from ventilator 105 and provide defibrillation in response. To increase the success rate for patient survival, defibrillation is provided by defibrillator 104 when ventilator 105 indicates that the patient is breathing in the expiratory phase. It is preferred, however, that defibrillation is provided when the patient's lungs are the most retracted, which occurs near the peak of expiratory gas flow. This is desired because the patient's heart is more exposed to the external defibrillation or pacing signal when the patient's lungs are more deflated. This is also because the chest electrical impedances are lower.

In accordance with the invention, system 100 changes the protocols implemented by it in response to the types of modules it includes. For example, the protocols are different if system 100 includes a defibrillator and ventilator from if system 100 includes only the defibrillator.

In operation, if the patient has cardiac arrest, resuscitation system 100 communicates with emergency services communication system 135. System 135 can be a 911 communication center, the police, the fire department, and/or a medical service. This communication can take place wirelessly or through a land-line connection and defibrillation can be performed in response. The land-line connection can be a telephone land-line, for example. The telephone land-line can be coupled to telecommunications module 130 through many different types of phone connectors known in the art.

In yet another example, in the event the call is to computer system 109 (FIG. 1a), remote control and data and/or voice communications can also be used. In addition, computer system 109 can remotely and periodically call system 100 for event data, self-test data, and to perform maintenance checks. If system 100 fails its self-test, it reports to computer system 109 in response, so that medical system 100 can be repaired and/or the owner can be notified. The modules can be arranged in different orders. Hence, system 100 can be customized according to user preference. For example, a right handed user may want telecommunication module 130 on one side of system 100 and a left-handed user may want module 130 on the other side.

The purpose is to highly coordinate and speed up the critical functions of resuscitation attempts by integrating devices that are typically used as separate devices and that are manually coordinated by separate individuals. It is also an objective to provide a voice/data link whereby collaboration or remote control with other specialists or whose response entities aid may be enlisted during an emergency. Each module may share data with the other as well as a remote PC and communications workstation, such as computer system 109. A standardized battery system is used so that life support may be maintained even when changing a battery in one module while another temporarily powers it through a commonly connected module. Modules may be used in stand-alone fashion or plugged together or used for expansion into greater functionality at a later date. When battery power is shared, additional safe guards may be in place to ensure that a short across one components does not drain the battery of all the components.

Ventilator 105 communicates with defibrillator 104 that it should shock after coordinating to a specific point in time. In this way, system 100 provides procedures corresponding to ABC protocols. This is beneficial because most defibrillators provide only the "C" or circulation resuscitation and do not coordinate their operation with ventilators to provide ABC resuscitation, as medical system 100. If patient 102 is confirmed in cardiac arrest or ventricular fibrillation defibrillator tells communications system 106 to call 911 or an assigned radio or telephone connection. If patient 102 is not in cardiac arrest, but hits help button 114 on communications unit, communications system 106 dials health support service instead of 911 dispatch. If system 100 is connected to remote computer system 109 managing communications, then system 109 can communicate commands for remote control of each module or all resuscitator functions.

In one example, if OnStar™ service gets a call about a crash, then they typically look up the local 911 dispatch center and then contact them. However, this is slow. System 100 is useful because it provides the ability to conference call to the 911 dispatch center so that no look up is necessary. Medical system 100 calls the local 911 dispatch center automatically. If communication system 106 calls a medical service, hospitals, then they can initiate their own emergency service, which gives them more control over where patient 102 is taken for treatment.

Figure 3A:
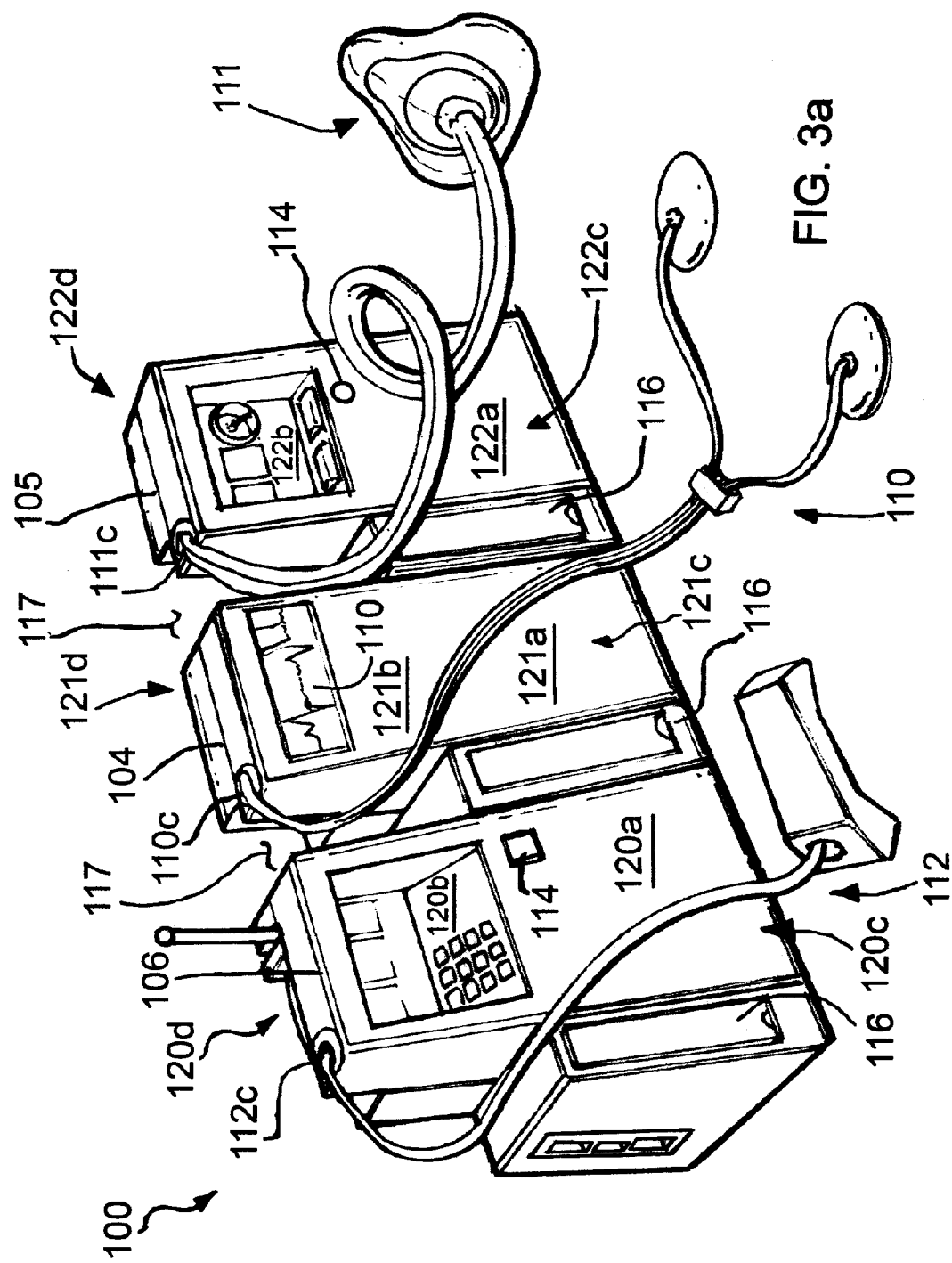
FIGS. 3a and 3b are simplified perspective and front views, respectively, of another embodiment of the medical system of FIG. 1a in accordance with the present invention.
Figure 3B:
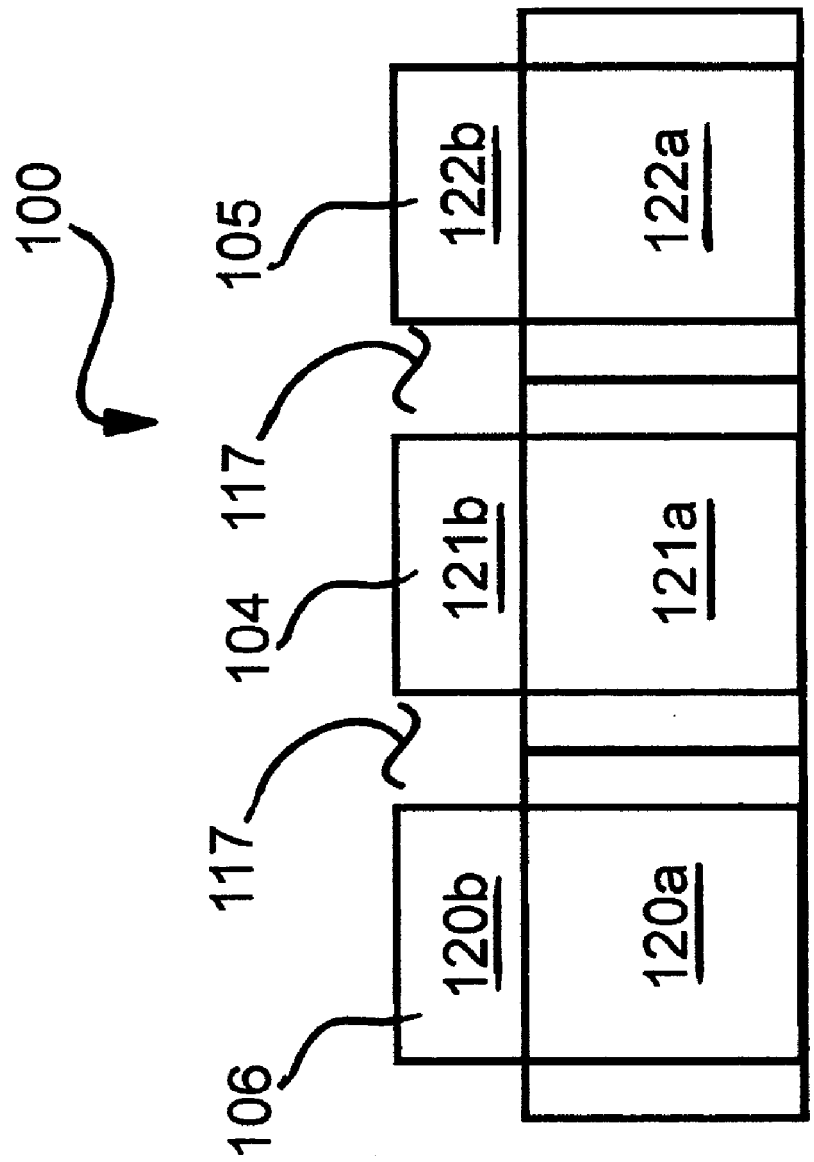

FIGS. 3a and 3b are simplified perspective and front views, respectively, of another embodiment of system 100 in accordance with the present invention. In this embodiment, system 100 includes defibrillator 104 positioned between communication system 106 and ventilator 105. Communication system 106, defibrillator 104, and ventilator 105 include bottom portions 120a, 121a, and 122a, respectively. Further, communication system 106, defibrillator 104, and ventilator 105 include top portions 120b, 121b, and 122b, respectively. Bottom portion 121a is shown in an attached condition with bottom portions 120a and 122a. Top portions 121b is spaced apart from top portions 120b and 122b by an opening 117. As shown in FIG. 3a, openings 117 can be used to guide components, such as electrode system 110, breathing circuit 111, and/or phone system 112 away from front portions 120c, 121c, and 122c of communication system 106, defibrillator 104, and ventilator 105, respectively. This is so that the user of system 100 can better see front portions 120c, 121c, and 122c. In this example, phone system 112 is connected to communication system 106 through port 112c, which is positioned on a top surface 120d of top portion 120b. Electrode system 110 is connected to defibrillator 104 through port 110c, which is positioned on a top surface 121d of top portion 121b. Breathing circuit 111 is connected to ventilator 105 through port 111c, which is positioned on a top surface 122d of top portion 122b. In this example, communication system 106, defibrillator 104, and ventilator 105 include battery packs 116 which can be used as replacement batteries if needed.

Figure 4:
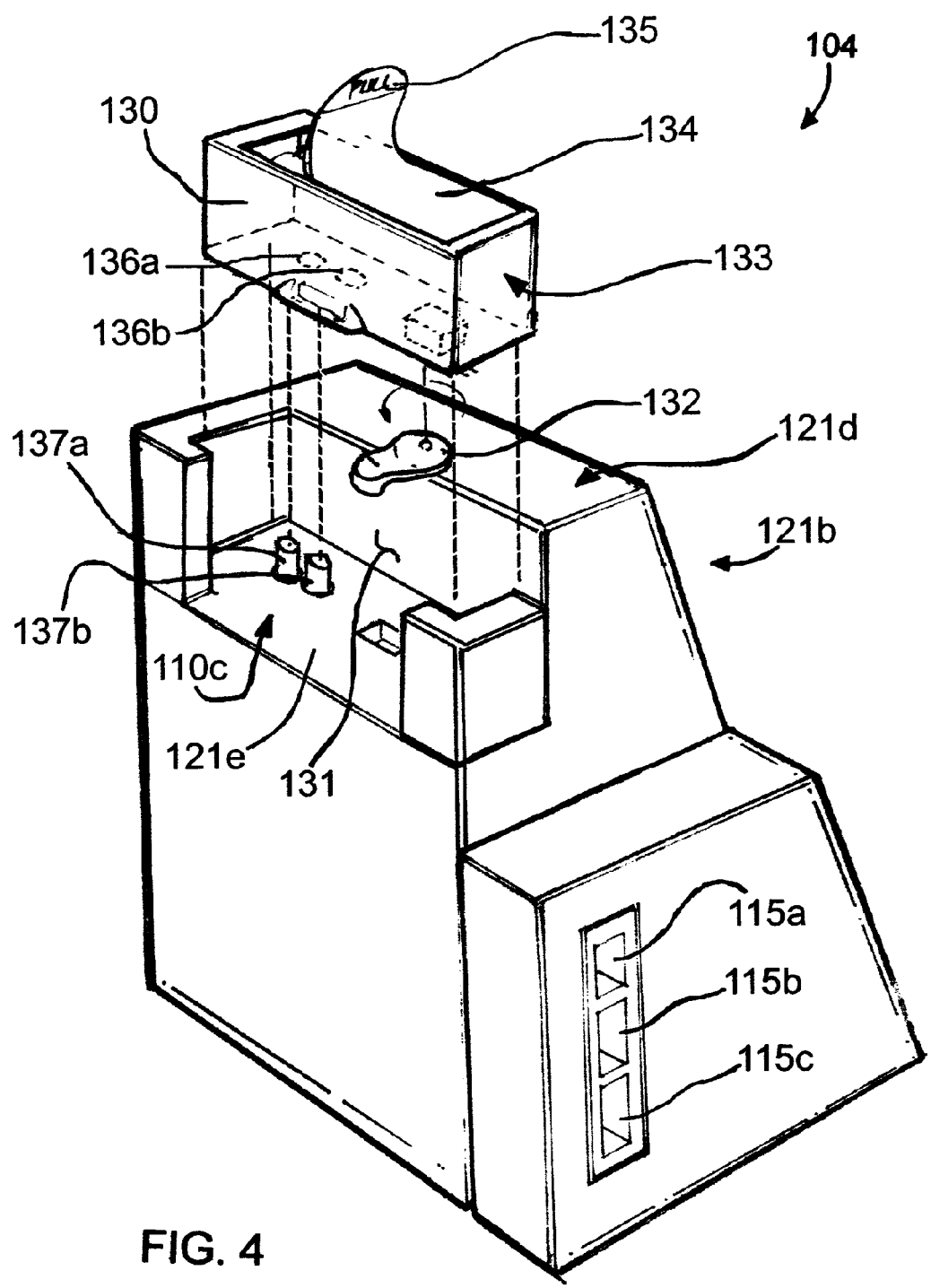

FIG. 4 is a simplified back view of another embodiment of top portion 121b of defibrillator 104 in accordance with the present invention. In this embodiment, top portion 121b includes an opening 131 which extends between top surface 121d and a surface 121e. Port 110c includes connectors 137a and 137b which extend upwardly from surface 121e towards surface 121d. Connectors 137a and 137b are for connecting to electrode system 110. Opening 131 is shaped and dimensioned to receive a storage container 133.

Storage container 133 includes openings 136a and 136b which are sized and dimensioned so that connectors 137a and 137b extend therethrough when container 133 is inserted into opening 131 and carried by surface 121e. A holder 132 is mounted to surface 121d. In this example, holder 132 is a spring clip used to lock container 133 in place. The spring clip can be held back so that container 133 can be removed from opening 131. In other examples, holder 132 is an arm rotatably mounted to surface 121d so that it can be moved between positions towards and away from opening 131. When holder 132 is in the position towards opening 131, it holds container 133 therein. When holder 132 is in the position away from opening 131, container 133 can be removed from opening 131. Container 133 includes a lid 134 which can be detached from container 133 by pulling a tab 135.

In accordance with the invention, storage container 133 includes a receptacle 130 which is sized and shaped to store various items for use with it defibrillator 104. A removable lid 175 is provided which can be easily detached from receptacle 130 so that the item can be removed therefrom. Storage container 133 is preferably sealed until the items stored therein are needed. This reduces the likelihood of contamination and increases the item's useable lifetime. This protects the electrodes from contamination, increases the lifetime of them, protects them from physical abuse and moisture, etc.

The items stored in storage container 133 can be of many different types, but in this example, they include electrode system 110. In other examples, receptacle 130 can store spare batteries for system 100 or other items. It should be noted that ventilator 105, communication system 140, and monitor can also include containers similar to container 133. For such a container for ventilator 105, it can be used to house an airway system similar to breathing circuit 111. For communication system 140, it can be used to store batteries and/or phone system 112. For monitor 107, it can be used to store electrodes similar to electrodes 113.

In operation, electrode system 110 is connected to port 110c when container 133 is positioned in opening 131. Container 133 with electrode system 110 positioned therein is inserted into opening 131 while holder 132 is away from opening 131. Container 133 is positioned so that it is carried by surface 121e and electrode system 110 is connected to 110c. When electrode system 110 is needed, tab 135 is pulled and top 134 disengages from body 130 of container 133. Electrode system 110 is then removed from body 130 and coupled to the patient. After use, holder 132 is moved to a position away from opening 131 and the empty container 133 is removed from opening 131. A new container 133 with a new electrode system 110 positioned therein is inserted into opening 131 so that the new electrode system 110 is coupled to port 110c. Holder 132 is then moved towards opening 131. The sequence is then repeated the next time electrode system 110 is needed.

Figure 5A:
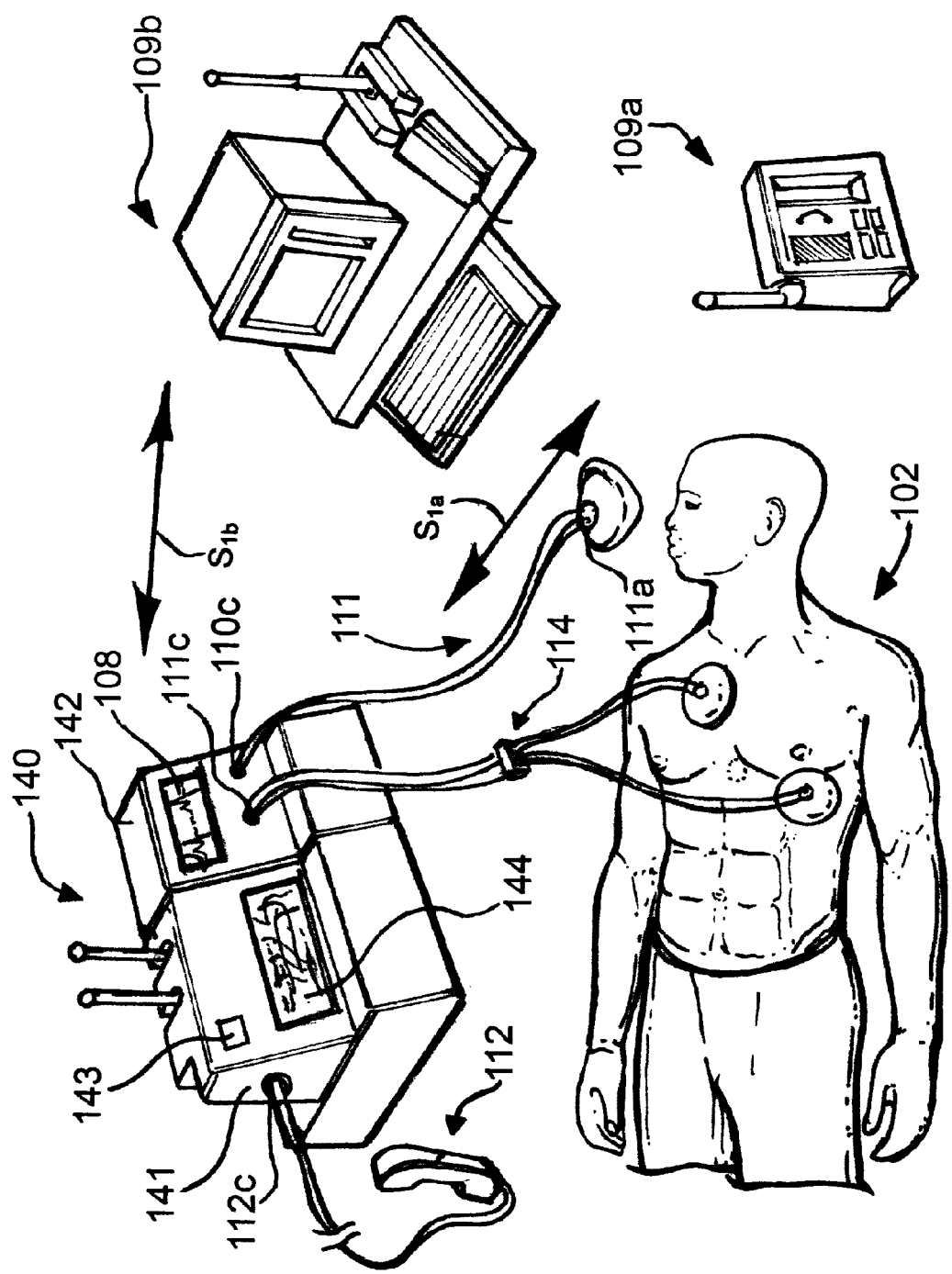
FIG. 5a is a simplified perspective view of a medical system with a resuscitation system in an attached condition with a communication system, in accordance with the present invention.

FIG. 5a is a simplified perspective view of a system 140 with a resuscitation system 142 in an attached condition with a communication system 141. System 140 is similar to system 100 discussed above. In this example, system 140 includes global positioning system 144 integrated with communication system 141. System 141 also includes a selector 143 for calling for help (help button). Selector 143 can be of many different types known in the art. In this particular example, it is a button, but in other examples, it can be a switch. Selector 143 is preferably labeled with "Help" so facilitate its use during an emergency when the person using system 140 is typically panicking or in a hurry. In these examples and others, selector 143 is colored, such as red or green, so that it can be visually located quickly. In some examples, it can even be lighted.

Resuscitation system 142 includes several systems which are integrated into a single module. In this example, these systems include a defibrillator, ventilator, and monitor. The defibrillator is the same or similar to defibrillator 104 described above. The ventilator and monitor are the same or similar to ventilator 105 and monitor 106, respectively, as described above.

In this embodiment, system 141 is programmed to initiate contact with an external emergency service in response to an indication from system 142 that patient 102 needs assistance. The contact can be initiated in several different ways. In this example, it is initiated when system 141 calls a predetermined phone number corresponding to a computer system 109*b* or an emergency service or provider. Communications system 141 can also include GPS system 144 to provide location information. The location information is relayed to the computer system 109*b* after the phone number is dialed. This can be done automatically in some examples.

In some embodiments, communication system 141 can be used by an outside maintenance or service company to initiate self-checks and/or confirm its location. During the self-checks, failures can be reported to the service company to initiate a maintenance or service call. Communication system 141 can also confirm its GPS location such that if it is stolen, then it can provide the new GPS location so that it can be recovered more easily. In this way, system 141 can operate as an asset recovery device.

Communication system 141 further includes communication system 112 to allow the user of system 100 to converse with a user of computer system 109*b*. Communication system 112 (such as a phone or radio) may also be used or triggered, if necessary, by the rescuer or patient, to initiate a local 911 or another emergency call to an emergency center 109*a*. In some examples, communication system 112 can be replaced with a "hands-free" communication system similar to that described above.

Communication system 141 has dual communication links may also be capable of having one link control the other link. For example, an initial call is made to a service that determines that a serious situation is evolving, such a cardiac arrest, and then the primary communications can control the second communications link. Thus, the call is made to a service which determines if a patient is in arrest and that person then issues commands from his or her location for the other communications link to call local 911 dispatch. There is the advantage of not having to look up remote 911 dispatch locations and then call.

In addition, the GPS information when transferred to the computer system 109*b* or emergency center 109*a*, can be used to assist in determining the estimated time of arrival to the scene or to the emergency center when the emergency center's GPS information is also included. Weather and traffic information can also be included in determining the estimated time of arrival. Moreover, based upon the estimated time of arrival, the emergency center or rescuer can relay commands through the system 140 to aid patient 102 and increase his or her survivability.

Software may also be developed for computer system 109*b* to perform communications through system 141. In one example, the software can speed interaction between computer system 109*b* and system 140 by requesting information, like GPS location or patient status, through built-in preprogrammed requests to resuscitation system 140.

In some embodiments, communication system 141 dials wirelessly (on radio or cellphone) or a directly connected phone line or integrated wireless phone detachable connection system. Calls can be auto-initiated by detection of cardiac arrest by system 140. System 141 can also try 9,911 or 8,911 dialing prefixes automatically if it cannot dial out of a private phone system.

System 140 with communication system 141 can also be equipped with one or more radios or cellular phones that autodial or repeatedly attempt to find help until a call is answered. This is useful if busy signals or communications resources are unavailable. It is also valuable if patient 102 us unconscious because system 141 will still attempt to communicate with systems 109*a* and/or 109*b* or provide GPS location information. System 140 can also verbally report its GPS location by using a programmed computer voice. An advantage is that it is not necessary to contact a third party. This feature of auto communication can be used to ensure that a patient or arrest victim or first responder or rescuer can get connected fast to communicate with available resources, such as 911 dispatch, the hospital, medical personnel, or relatives. It also frees the hands of the rescuer or patient should other critical needs arise.

System 141 can also prioritize the calling of various hospitals based on location so that there is a hierarchy in calling. To accomplish this, communication system 141 is programmed to try many phone numbers or number combinations including dialing '9,' or '8,' etc. to establish an outside line or link to a radio channel until a successful call is confirmed. If patient 102 has become unconscious, then system 140 can still verbally announce its location, such as GPS location, so listeners to the call can tell where patient 102 is located. Similarly, other notification or pertinent data can be relayed to the listener by system 141.

In this example, communication system 141 is activated with selector 143 which operates as a "Help button". When selector 143 is activated, it initiates a preprogrammed sequence of calls using telephone, radio, and/or cellular communications.

When a communication link is established, system 112 function 'hands free' for voice communications with the use of microphone and speakers built into system 141. It may also automatically initiate this sequence if the resuscitator detects symptoms of cardiac arrest. System 141 may record all communications and data for replay after the event. System 141 may trigger GPS and data announcements if no response originates from the remote scene. System 141 may announce identification data so that a related database of information can be consulted. In one example, the identification data includes the name and address of the person that owns system 100. This may be useful in identifying patient 102.

In some examples, system 140 includes a touch pad, similar to that found with a conventional phone. The touch pad can be used by the user of system 160 to dial a particular number, such as that corresponding to a home, friend, neighbor, doctor, hospital, etc. If selector There will be a help button and a touch tone pad to dial a specific number. The help button is equivalent to a dial button on a phone. If a number is not punched, it goes through its dialing sequence already programmed in.

Figure 6:
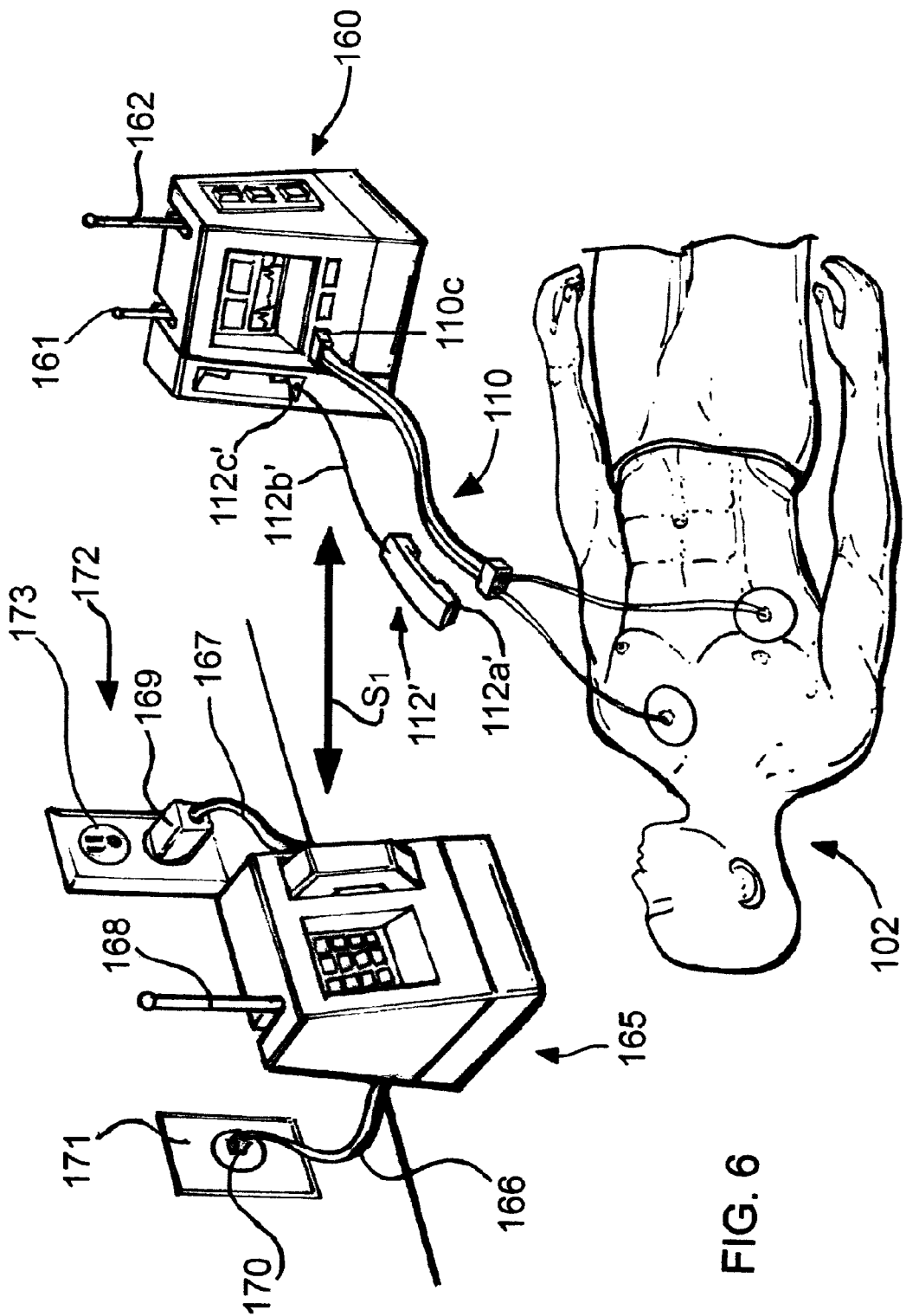
FIG. 6 is a simplified perspective view of a defibrillator in accordance with the present invention.

FIG. 6 is a simplified perspective view of a defibrillator 160 in accordance with the present invention. Defibrillator 160 is similar to defibrillator 104 discussed above only it includes an integrated communications system, similar to system 106, which can be used as a portable phone. In this example, however, the integrated communication system includes a low power radio system which is lower in cost. One reason it is lower in cost is because it has a smaller range than system 106, so it can include less expensive electronic components. One example of a low power radio system is a walkie talkie or a portable telephone. System 165 is useful in situations where the end user has land line phone service, but not wireless service. This reduces the need for the end user to have to pay for wireless service.

In this example, defibrillator 160 includes a low power radio system 112'. Here, system 112' includes a telephone 112a' coupled to defibrillator 160 through a cable 112b'. Cable 112b' has an end connected to telephone 112a' and an oppose end connected to a port 112c' of defibrillator 160. Port 112c' is connected to an antenna 162 and GPS system 144 is coupled to a GPS antenna 161. In other embodiments, system 112 can be a hands free phone system, such as speaker phone, as described in detail above. In this way, system 112' provides voice communications for system 100 through telephone 112a' and antenna 162, so that data and/or voice signals can flow between it and an external communication system.

In accordance with the invention, one type of external communication system is portable communication system 165. Portable communication system 165 includes an antenna 168, a communication cable 166 with one end connected to a connector 170. System 165 also includes a power cable 167 with one end connected to a power plug 169. Power plug 169 is connected to a socket 173 of an outlet 172 in a known manner. In this way, system 165 is provided with power through cable 167. In other examples, system 165 is battery powered. Cable 166 is connected in a conventional manner to a phone line (not shown) through a phone jack 171 which receives connector 170. In this way, system 165 can transmit and receive data through the phone line, as will be discussed in more detail below. The phone line preferably provides access to an emergency medical system or a medical dispatch center, such as 911.

In some examples, a phone jack may not be conveniently located. In these instances, connector 170 can be coupled to a phone box through a punch block, which is known in the art. The punch block generally allows multiple connections so more than one connector 170 can be coupled thereto. This is useful in a setting, such as an office, where a number of systems 160 may be needed.

There are several situations in which system 165 is useful. One situation is where defibrillator 160 is needed for use at a location away from a land-line phone system. In these situations, portable communication system 165 is coupled to socket 172 and phone jack 171 as described above. Defibrillator 160 is moved to a location near patient 102 so that electrode system 110 can be coupled thereto as described in detail above. Telephone 112a' can be used by patient 102 or another user of system 160 to communicate with the phone line through cable 166, system 165 defibrillator 160, and voice/data communication system 112'. Signal $S_1$ is flowed between antennas 168 and 162. In this way, defibrillator 160 can be used as a portable phone. An advantage of system 160 is that it has a lower cost because it includes a low power radio system which is less expensive than a more powerful system.

Another situation where system 165 is useful is where defibrillator 160 is needed for use at a location inside a building where wireless communications may not be possible or reliable. This is often the case in buildings that include materials that attenuate the flow of wireless signals therethrough. In these situations, defibrillator 160 and system 165 can be used as described above to couple telephone 112a' to a phone line in the building. This is also useful in the case where wireless service is unavailable or interrupted and an available option is using a land line. This can be the case in a remote location where a land line is available, but wireless service is not. Another location where wireless communications may not be possible is in a basement of a house or in an underground structure.

In some situations, system 165 can be preconnected to the phone line or a wireless network so that the user or patient does not have to take the time to set it up. In some situations, such as in a single building, a number of defibrillators 160 can be located. Each defibrillator 160 can be in communication with a central system 165. System 165 can support one or more communication links from corresponding defibrillators. In some examples, connector 170 can be connected to an alarm system. The alarm system can contact emergency center, 911 response center, police, fire department, ambulance, etc. in response to the user using system 112'.

FIG. 7 is a simplified perspective view of a system 180 in accordance with the present invention. System 180 is the same or similar to system 100 discussed above. System 180 includes a microphone 183 and speaker 184 for receiving and transmitting, respectively, audio signals. System 180 also includes an antenna 162 for receiving a radio signal. Antenna 162 can be of many different types, but is shown here as an external antenna for illustrative purposes. In other examples, however, it can be an internal antenna such as those used in some cell phones or other communication devices.

System 180 includes control circuitry that allows the operation of microphone 183 and speaker 184 to be coordinated. The operation of microphone 183 and 184 can be coordinated in many different ways. In a particular example, speaker 184 is deactivated when microphone 183 is activated and speaker 184 is activated when microphone 183 is deactivated. In this way, microphone 183 does not record the audio signals transmitted by speaker 184. In this example, microphone 183 will receive other audio sounds, such as those from the patient and responder. System 180 can also include control and sensor circuitry so that a human audio signal is given priority over an audio signal provided by speaker 184. This will permit select voice information from being obscured or interfered with when the patient or rescuers, or hospital or 911 personnel speak during live communications. This feature restricts recorded conversations from being 'corrupted' when recorded because full conversations will be recorded.

System 180 includes audio circuitry that differentiates between audio signals transmitted from speaker 184 and other audio signals, such as those from patient, responder, and other nearby humans. The audio signals can also be from rescuers on the scene, the victim or patient, and connected personnel 430, such as hospital, 911, or other communication links System 180 deactivates speaker 184 when others in the communication link or links are speaking unless life-threatening communications are preferred. Life-threatening communications are preferred in several different situations, such as when a defibrillator signal is to be provided by defibrillator 104 (FIG. 1a). In some examples, the audio circuitry provides the capability for a user at a remote location to override functions provided by system 180. These functions can be audio sounds provided by speaker 184 and audio sounds recorded by microphone 183. In this way, system 180 prioritizes the function according to the situation.

In accordance with the invention, system 180 includes software which controls the operation of a computer included therein. The computer can be of many different types known in the art and generally includes a processor for executing instructions in the software and memory for storing data. The audio sounds transmitted by speaker 426 can be stored by system 180 in many different ways. In this example, the audio sounds are stored on a memory chip included in the computer. In other examples, however, the audio sounds are stored on a hard drive or magnetic tape included in the computer. In some examples, system 180 provides a computer voice through speaker 184 to guide rescuers and/or patients through procedures. These procedures can include instructions on the use of system 180 and/or instructions on how to deal with the particular emergency situation.

The software provides many different functions for system 180. In this example, the software provides language recognition so that system 180 can interact with the user of system 180. The language recognition software can include software that recognizes many different languages. This is useful so that system 180 can interact with people who speak and understand different languages. The particular language can depend on the location of system 180 as provided by GPS system 144. This can also be used so that speaker 184 transmits audio sounds in the appropriate language as determined by GPS system 144. System 180 may also switch languages based on GPS location for both communications and local audio responses to rescuers and patients. The audio sounds can include voice commands and instructions and/or signals, such as a beep to provide a warning.

In some embodiments, speaker 184 is deactivated by control circuitry in response to an indication that the patient, responder, and/or connected communications at the scene tries to talk. This feature is useful to reduce the likelihood that speaker 184 emits an audio sound when commands or conversations near system 180 being spoken by the user of system 180 or other people nearby. An example of one exception to this is when system 180 is about to provide signal $S_{Defib}$ to the patient. In these instances, it is desired for speaker 184 to emit a warning sound so that people are warned to stand back from the patient while he or she is being defibrillated. As mentioned above, speaker 184 can also be deactivated remotely by a user in communication with system 180.

FIG. 8 is a simplified perspective view of system 100 in communication with emergency centers 190a, 190b, and 190c. Emergency centers 190a-190c can be of many different types. In this example, they include hospitals, but they can include fire departments, emergency call centers, such as a 911 call center, and ambulances, etc. in other examples.

In accordance with the invention, system 100 includes GPS system 144 and antenna 162, which are discussed above. In this example, system 100 includes control system 98 (FIG. 1d) for determining which emergency center to contact in response to an indication of an emergency. Control system 98 and its software is connected to data system 182 for storing emergency numbers therein. The particular emergency number called depends on the distance of GPS system 144 away from centers 190a-190c. This feature is useful because it is generally desirable to contact the emergency center that is closest to GPS system 144. This is because it is more likely to take the closest call center less time to send a responder to GPS system 144 and the patient that needs help.

In some examples, control system 98 can also call multiple call centers in a sequence based on availability. For example, call center 190a may be the closest to GPS system 144 and very busy. Call center 190b may be farther from GPS system 144, but not too busy. In these situations, system 100 can contact center 190a to determine this and then contact center 190b as an alternative.

Control system 98 can initiate the communications or this can be done manually by a user of system 100. System 100 can include a data port so that numbers stored in data system 182 can be updated. It is desirable to update the numbers if system 100 is moved from one geographical region to another because the desired numbers typically change with geographical region.

System 100 can change location in many different situations. For example, it can be carried in a car or vehicle to different states, countries, suburbs, or other locations. It is generally known that when the location changes, the local 911 or emergency access number(s) or radio frequency(s) do too. As a result, the numbers stored in system 100 should correspondingly change to reduce the emergency response times by calling the closest services.

The database of appropriate number or numbers stored by system 100 can be dialed and communications initialized to the appropriate number or frequency. The database can determine which number to contact in response to the GPS location provided by GPS system 144. In some instances, communications may fail. In these instances, system 100 attempts to contact emergency centers 190a-190c using other resources, such as with phone system 112. In some examples, system 100 can dial multiple numbers until it successfully makes contact with one of centers 190a-190c.

In some embodiments, system 100 includes GPS locator selector 193 (FIG. 1d) connected to GPS system 144 which can be activated to communicate its location. An advantage of this feature is that the location of system 100 is provided to the responder faster and more accurately. The location can be provided in many different ways, such as by a phone call, an audio sound, and a radio signal. This locator selector operates in a similar manner to a fire alarm sensor which indicates the location of smoke or a fire to emergency personnel.

GPS locator selector 193, when activated, causes the computer voice of communications system 106 to announce its location. This is convenient for rescuers or conscious cardiac arrest victims who want system 106 to quickly convey location information to the parties that are being communicated with. This is especially important if patient 102 is alone and is having difficulty speaking.

FIG. 9a is a simplified perspective view of an embodiment of a system 100', in accordance with the present invention. In this embodiment, system 100' includes a ventilator 105' in an engaged condition with defibrillator 104. Defibrillator 104 provides electrotherapy to the heart of patient 102 through electrode system 110. Ventilator 105' is similar to ventilator 105 but it provides Airway Pressure Release Ventilation (ARPV) and includes a chemical source, as will be discussed in more detail below. The chemical source is in communication with the airway or lungs of patient 102 through ventilator 105' and provides a chemical agent thereto when patient 102 is being ventilated.

System 100' is useful because if the heart is paced or defibrillated by defibrillator 104 and it does not have enough replacement oxygen, then patient 102 can die in response. This is because when the heart is stimulated with a pacing and defibrillating signal, the amount of oxygen included therein decreases and should be replaced. If it is not replaced, then it is more likely that patient 102 will die. In other words, the heart should get replacement oxygen so it does not run out or it can undesirably stop working.

In this embodiment, ventilator 105' is in communication with the airway and lungs of patient 102 through an air-way breathing circuit 111'. As an example, air-way breathing circuit 111' provides a closed ventilation circuit for patient 102. A closed or semi-closed ventilation system reduces the likelihood of spreading contagious diseases to others if patient 102 is infected. Air-way breathing circuit 111' includes an expiratory tube 128 and an inspiratory tube 129. Ends of tubes 128 and 129 are connected at one end to ventilator 105' at port 111c and their opposed ends are connected to mask 111a.

In some examples, ventilator 105' can be controlled with a single or dual venturi driven oxygen or air jet positive or negative pressure inducing system. Ventilator 105' is typically programmed so that it operates interactively with defibrillator 104. The operation of defibrillator 104 and ventilator 105' is interactive so that defibrillation, pacing, ventilation, CPR, and monitoring functions for specific behavior or protocols during their critical procedures all from the same device. Ventilator 105' typically houses an oxygen tank coupled to circuit 111'. The oxygen tank is generally replaceable, rechargeable, and/or refillable. Ventilator 105' also includes a compressor to produce pressure.

In some examples, ventilator 105' also includes a means for detecting cardiac arrest of the patient. The means for detecting cardiac arrest would be part of defibrillator 104 and is known in the prior art. Ventilator 105' also includes a means for hyperventilating the patient through the means for providing an airway to a patient when the patient is in cardiac arrest, such that the ventilation system automatically hyperventilates the patient when the patient is detected to be in cardiac arrest.

Furthermore, fail-safe valves may also be installed on both inspiratory 129 and expiratory 128 parts of the airway to provide the ability for the patient to breath outside air if ventilator 105' fails. If ventilator 105' should fail, the compressor is turned off to preserve battery power. Expiratory valve 128 is included to maintain and control pressure values. A gas port 119 is used to extend ventilation for long periods.

Circuit 111' also includes sensors to monitor breathing, insertion into the mouth, and protocols are adjusted to these events. For example, if no breathing and no ECG occurs for predetermined period of time, then attempts at resuscitation or modifying ventilation rate based of rate of breaths.

In accordance with the invention, ventilator 105' also includes a chemical source 194. Chemical source 194 is attached to air-way breathing circuit 111' so that it can provide a chemical agent to tube 128. The chemical agent can be of many different types. For example, it can include vasopressin, epinephrine, and/or other chemical agents. This is useful because if patient 102 has poor circulation, then chemical agents injected by needle into his or her veins will not readily flow because the blood pressure will be too low. Non-invasive infusion into the airway and lungs are much faster and more effective than invasive infusion, such as using a needle. In this way, system 100' provides more effective and rapid infusion of drugs, agents, and/or gases into patient 102.

FIG. 9b is a simplified front view of air-way breathing circuit 111' showing mask 111a in more detail. In accordance with the invention, mask 111a includes contact 149 for ionizing the chemical agent as it flows therethrough tube 129. In other embodiments, contact 149 can be positioned otherwise to ionize the chemical agent. For example, it can be positioned in ventilator 105' near chemical source 194. In some example, a power source is coupled to contact 149. The power source can be an external power source or it can be a power source included in defibrillator 104 or ventilator 105'.

In this example, positive charges are proximate to electrode pads 110a and 110b and negative charges are near contact 149 proximate to mask 111a, although the polarity of charges can be reversed. Contact 149 extends along tubes 128 and 129 and includes a conductive surface to aid in charging the drugs, agents, chemicals, or gas, such as but not limited to, epinephrine, vasopressin, combinations thereof, or similar, etc.

Hence, ventilator 105' and breathing circuit 111' electrically charges drugs, oxygen, or other agents at or near the airway from oppositely electrically charged external electrodes on the patient (electrodes 110a and/or 110b). The electrical circuit formed by electrodes 110a and/or 110b and contact 149 enhances or accelerates the assimilation of the chemical agents into the blood stream of patient 102 noninvasively through the airway, trachea, and/or lungs.

If a stand-alone ventilator 105' is used for common ventilation purposes but the patient connected to it arrests, then a CPR button can be actuated manually providing CPR coordinated ventilation procedures. If ventilator 105' is interconnected with monitor 107 or defibrillator 104, then this can be automated interactively by integrating these procedures during cardiac arrest. Pressing the CPR button again may halt the CPR sequence or cycle. In this way, the CPR mode and the operation of defibrillator 104 are coordinated. Further, the CPR mode is turned off when defibrillator 104 provides signal $S_{Defib}$.

In this embodiment, mask 111a' includes a microphone 148 which provides audio sounds from patient 102. Microphone 148 is carried by mask 111a and connected to ventilator 105', but it can be positioned in other locations in other embodiments. For example, microphone 148 can be a standalone microphone which can be positioned on the chest of patient 102. Microphone 148 is useful to hear the breathing of patient 120 which is desirable so that more effective treatment can be provided. The treatment is more effective for several reasons. For example, the breathing or lack of breathing of patient 102 often indicates if he or she is in respiratory arrest. This is important because a patient in respiratory arrest often suffers from cardiac arrest soon thereafter. As a result, if the patient can be effectively treated for respiratory arrest, then he or she can be prevented from going into cardiac arrest.

The chemical agent can be provided to the blood stream of patient 102 in many different ways. The chemical agent is preferably flowed into the blood stream of patient 102 through his or her lungs, but some of the chemical agent can be flowed into the blood stream after is flows through mask 111a and before it reaches the lungs. This can happen if the chemical agent is absorbed in the mouth or trachea, for example, of patient 102. The chemical is flowed into the lungs of patient 102 in response to a potential difference between contact 149 and electrodes 110a and/or 110b.

In some examples, ventilator 105' includes an absorber 191 to prolong ventilation cycle times during individual procedures. The absorber preferably includes a soda lime carbon dioxide absorber. Soda lime $CO_2$ can pass oxygen but it absorps $CO_2$. Patient 102 is breathing in a closed circuit, so the spread of disease is reduced. Ventilator 120 and/or breathing circuit may thus have one or more filters to halt spread of infectious diseases. Separate inspiratory and expiratory nuclear, biological, and/or chemical filters may be used to protect patient and/or protect local rescue personnel.

The protocols can change if the patient is in cardiac arrest. As discussed in detail in conjunction with FIG. 1A, defibrillator 104 and ventilator 105' are in communication with each other so that data and power signals can flow therebetween. Ventilator 105' reduces the amount of carbon oxide from a tube and provides air and/or oxygen in tube for patient 102. The protocols are adjustable in response to a signal flowing between the first and second communication system.

For example, during defibrillation it is important that ventilation is performed at 'peak expiration' or with negative airway pressure to expose the heart in the chest to external countershock. In one example, ventilator 120 provides oxygen to patient 102 in response to an indication from defibrillator 104 that patient 102 is in asystole. Asystole is a term commonly used in the medical field to indicate heart standstill. A patient is generally in heart standstill when his or her heart rate is below a predetermined value or is zero. Asystole can be determined by monitor 107 or defibrillator 104 and is generally displayed as a ECG "flat line" by it. A patient in asystole is very close to dying and will generally die unless ventilation and/or defibrillation is provided.

In operation, defibrillator 104 provides cardiac arrest detection and ventilator 105' changes its protocols to provide more oxygen if needed. The ventilation rate may also increase. Ventilator 105' controls the amount of air, the composition of the air, the amount and type of chemical agents in the air, and the ventilation rate. In this way, ventilator 105 operates as a ventilator and an infusion system. An infusion system is one that feeds chemicals to the body, such as the lungs and/or blood stream. Ephenephrine injection is generally done using a needle, but this is an invasive procedure and is not as efficient as infusing it through the air-way of patient 102. Also, by infusing these chemical agents into the lungs of patient 102, they are flowed to the heart physiologically in a shorter amount of time.

It may be found that it is preferable to use a mask to allow the rescuer or system to hear the patient speaking. Moreover, to further assist the rescuer or system to hear the patient, a microphone 480 may be placed in the mask or in the ventilator to help amplify the patient's voice and breathing sounds.

In this embodiment, ventilator 105' includes a selector 118 which can be activated to initiate a CPR sequence or cycle wherein ventilation procedures are coordinated or timed with CPR efforts. If cardiac arrest or ventricular fibrillation is detected by defibrillator 104, then the CPR mode is desired. In some examples, the CPR mode involves ventilator 105' ventilating or hyperventilating patient 102 followed by a period where ventilator 105' reduces the amount of ventilation and provides audible beeps or instructions for CPR timing of required chest compressions.

An audio alarm can also provide a sound in response to selector 118 being activated. The sound is provided to warn responders to secure or reattach breathing circuit 111' and/or mask 111a. The alarm can be activated in response to an indication that there is a leak or a significant reduction in pressure.

Figure 10A:
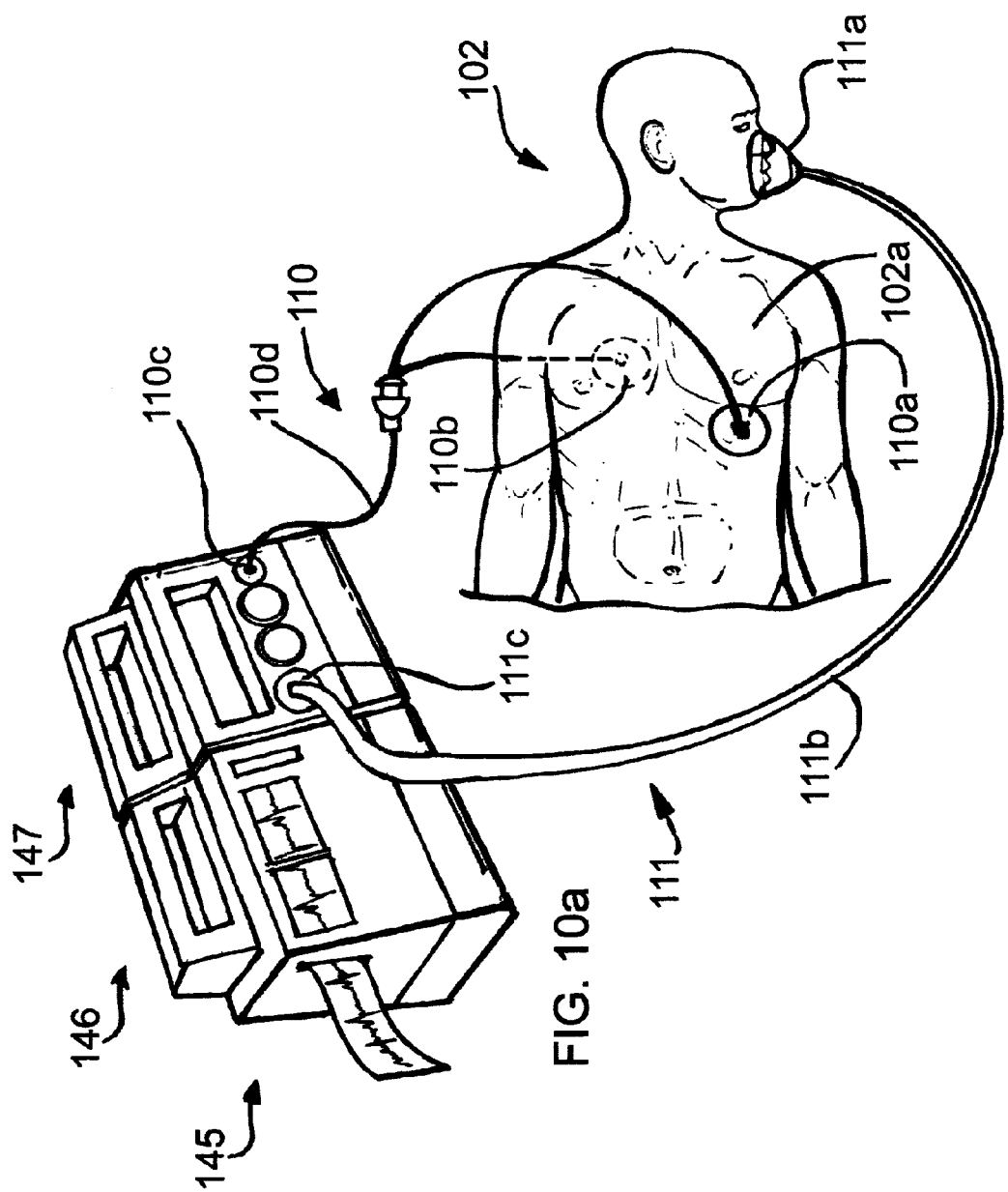
FIG. 10a is a simplified view of a medical system in accordance with the present invention.
Figure 10B:
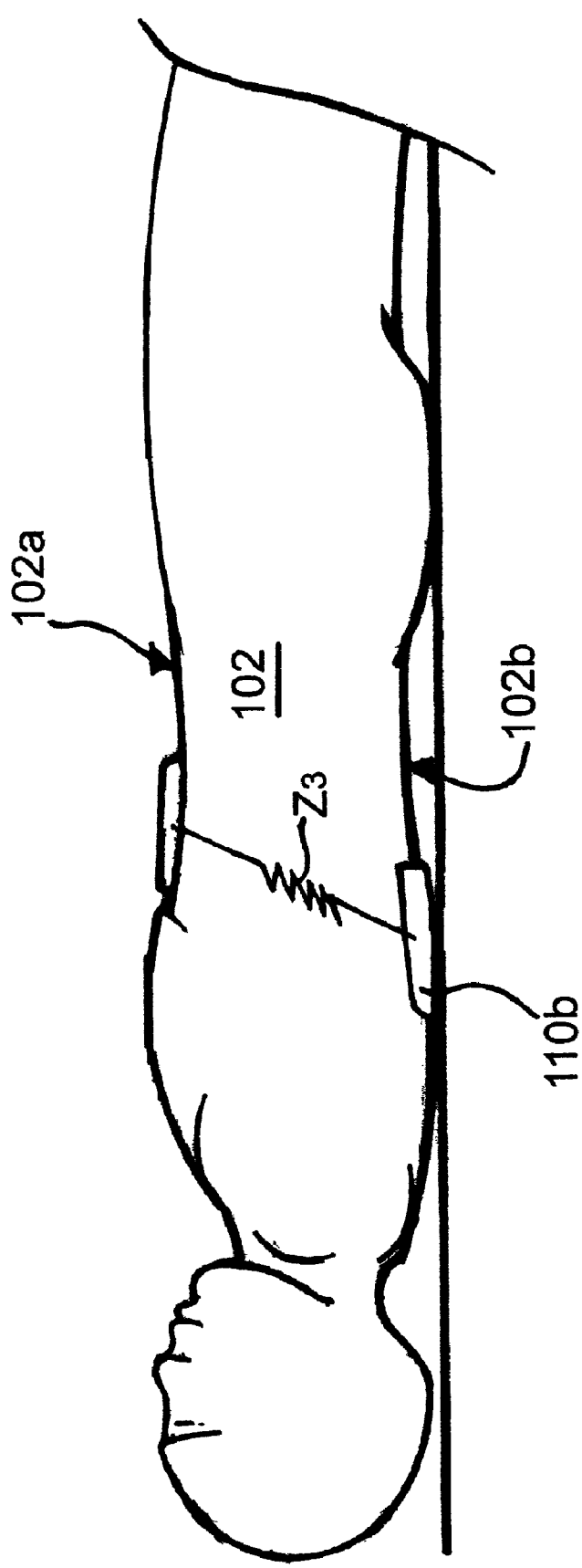

FIG. 10a is a simplified view of a system 145 in accordance with the present invention and FIG. 10b is a simplified side view of patient 102. In this embodiment, system 145 includes a monitor 146 in an attached condition with a life support system 147. Air way breathing circuit 111 extends from port 111c of system 147 and it coupled to air mask 111a. Air mask 111a is coupled to the mouth of patient 102. Electrode system 110 extends from port 110c of system 147 and is coupled to electrode pads 110a and 110b. In accordance with the invention, electrode pad 110a is coupled to patient 102 near an anterior apex (FIG. 10b) position and electrode pad 110b is coupled to posterior 102b of patient 102 (FIG. 10b) so that impedance $Z_3$ is between them. Electrodes 110a and 110b in these positions are capable of providing defibrillation, pacing, and monitoring for patient 102.

System 147 includes an oxygen source (not shown) in communication with airway breathing circuit 111 so that it can provide oxygen to patient 102. The oxygen source is typically housed within system 147 so that it is better protected. Monitor 146 includes a recorder to store the vital signs of patient 102.

An advantage provided by system 145 is that system 147 provides airway management of patient 102 and defibrillation and pacing. Monitor 146 is coupled to system 147 so that it can monitor the vital signs of patient 102. In this way, separate monitor electrodes do not need to be used because electrodes 110a and 110b are used instead. This saves money because fewer electrodes are used. It also saves time because fewer electrodes need to be coupled to patient 102. Fewer electrodes are used to provide defibrillation, pacing, and monitoring of patient 102. Fewer modules are needed to provide these functions.

FIG. 11a is a simplified perspective view of system 100 with defibrillator 104 and ventilator 105. System 100 includes reverse lighted displays 200 and 210. The display indicators included in displays 200 and 210 are activated and deactivated in response to the protocol being implemented with system 100. The protocol determines steps in resuscitation, ventilation, pacing, etc.

Here, display 200 is carried by defibrillator 104 and display 210 is carried by ventilator 105. Display 200 includes display indicators 201, 202, 203, 204, 205, 206, 207, and 208. Similarly, display 210 includes display indicators 211, 212, 213, 214, 215, 216, and 217. Display indicators 201-208 and 211-217 provide various images when activated. The images generally include text, pictures, or combinations thereof. The pictures and text provide Information to the user of system 100 regarding the procedures for its use. In some examples, the images indicate the status of system 100. Display indicators 201-208 and 211-217 can have many different structures and operate in many different ways.

FIG. 11b is a simplified side view of a portion of display 200 showing one embodiment of display indicators 204 and 205. In this embodiment, display indicator 204 includes a light emitter 220 positioned between opposed sidewalls 222 and 223. Opposed sidewalls 222 and 223 carry a plate 225 which carries the corresponding image for indicator 204. Plate 225 is carried by sidewalls 222 and 223 so that light 227 emitted from emitter 220 flows through plate 225 and is emitted therefrom as light 228 when display indicator 204 is activated. In this instance, the visibility of the image on plate 225 is increased. When display indicator 204 is deactivated, light 227 is not emitted by emitter 220 and light 228 does not flow through plate 225. In this instance, the visibility of the image carried by plate 225 is decreased.

Display indicator 205 includes a light emitter 221 positioned between opposed sidewalls 223 and 224 so that sidewall 223 separates emitters 220 and 221. Sidewalls 223 and 224 carry a plate 226 similar to plate 225 discussed above. Plate 226, however, generally has a different image on it so that display indicator 205 provides different information than indicator 204. Sidewall 223 separates emitters 220 and 221 so that light emitted from emitter 220 does not flow through plate 226 and light emitted from emitter 221 does not flow through plate 225.

In this example, emitter 221 is off so that light is not flowed through plate 226 and its corresponding image is less visible. Plates 225 and 226 can be made of many different materials, such as glass, plastic, etc. Further, light emitters 220 and 221 can be many different types of light emitters, such as light emitting diodes, light bulbs, etc., which are known in the art. Liquid crystal displays can also be used, but they tend to be more expensive. In some embodiments, plates 225 and 226 can be a single continuous piece, but they are shown as separate pieces for illustrative purposes. In this way, display indicators 204 and 205 operate as reverse lit displays. It should be noted that the other display indicators included in displays 200 and 210 can be the same or similar to displays 204 and 205 shown in FIG. 11b.

An advantage of displays 200 and 210 is that the user of system 100 is provided with a simple to read and understand display of relevant information on how to use system 100 and which procedures to follow. The procedures can be medical or operational procedures, such as turning system 100 on or off. Simplicity and clear communication by such displays are life-saving in emergency situations. Displays 200 and 210 are also sized and shaped so that they are bigger and more visible.

The images included in displays 200 and 210 are generally instructive in nature so that they show the user how to perform a particular task. This is more useful for a layperson that is generally not familiar with medical procedures. The tasks can include how to provide the electrodes, how to provide the defibrillation and/or pacing signals, how to tilt the patient's head, etc. In some examples, the images are instructive in nature by telling the user what or what not to do.

Figure 12A:
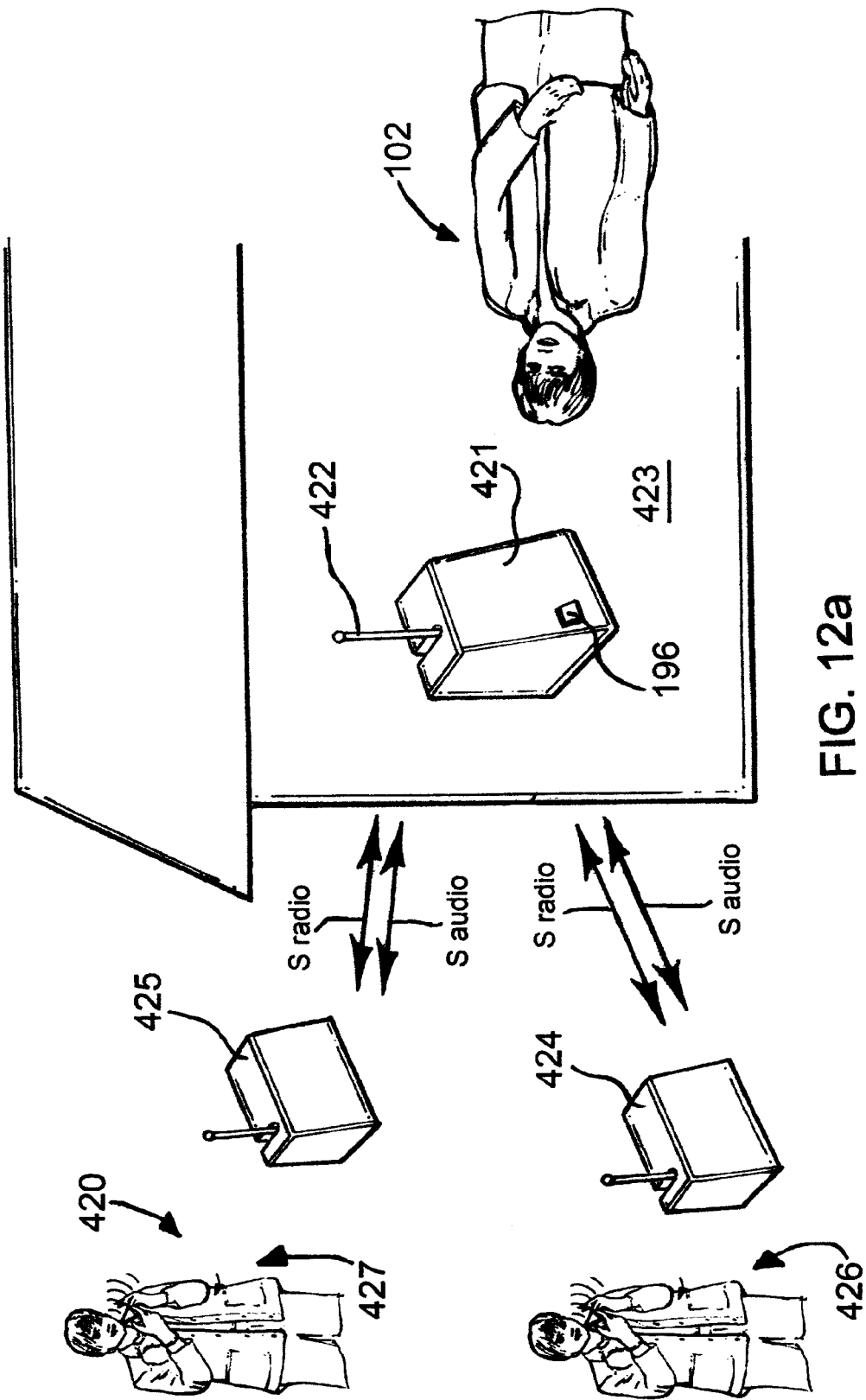
FIG. 12a is a simplified perspective view of a medical system in accordance with the present invention.

FIG. 12a is a simplified perspective view of a system 420 in accordance with the present invention. It should be noted that system 421 can be similar to system 100 discussed above. System 420 provides several advantages with one being that the location of the patient can be determined faster. This is important since the survival of the patient depends on the response time of the responder. In this embodiment, system 421 can transmit and receive audio signals in response to the presence of a person near system 421. In this example, the transmitted audio signals are emitted by speaker 184 connected to audio system 180 and the received audio signals are detected by microphone 183 connected to audio system 180.

The received audio signal can be of many different types. For example, it can be words or sounds from a person, such as the patient or a responder helping the patient. The received audio signal can also be an electronically generated voice or sound. The transmitted audio signal can be provided in many different situations by system 421. For example, it can be provided when system 421 determines that there are no local rescuers nearby. The transmitted audio signal can also be provided if the patient is determined by system 421 to be in cardiac arrest. The patient can be determined to be in cardiac arrest by system 421 if it includes a monitor the same or similar to monitor 107 discussed above.

In a typical situation, patient 102 is in structure 423 where he or she is not readily visible or locatable by responder 426 or 427. In this situation, system 421 can emit a radio signal $S_{Radio}$ and/or an audio signal $S_{Audio}$, as discussed above. The radio signal is received by units 424 and 425 and, in response, provides more information about the location of patient 102 to responders 426 and 427, respectively. In some examples, units 424 and/or 425 can transmit the radio signal to system 421 which transmits the audio signal in response. In this way, the audio sound provides more information about the location of patient 102.

Receiver units 424 and/or 425 can include an electronic voice that is audible so that responders in the vicinity knows what floor and which way to go to find patient 102. In some examples, receiver units 424 and/or 425 can include an audio system that emits a beeping sound, similar to that in other alarm systems, such as an avalanche alarm. In some example, system 421 includes a selector 195 (FIG. 1d) for activating and deactivating the audio signal. Selector 195 is connected to audio system 180 and can be of many types known in the art. For example, it can be a button or a switch similar to selector 193 discussed above.

This feature is useful in case patient 102 is unconscious or otherwise unable to communicate. Selector 195 can also be activated to turn on and off the audio signal in situations where it is inappropriate for the audio signal to be emitted. This situation can be people near system 421 are trying to communicate. In this way, selector 195 can be used to override the transmission of the audio signal.

In some embodiments, system 421 includes a selector 196 for activating a loud sound signal. Selector 196 is also coupled to audio system 180 and operates as a screamer button for providing a piercing sound that can be heard at a distance and through doors, walls, and other structure. This is useful if responder 426 and/or 427 is near patient 102, but still can't find him or her. For example, patient 102 can be hidden in the bathroom of a large house or in a back office. In these embodiments, system 421 includes a selector for deactivating the loud sound in case it is no longer needed or the patient or responder finds it to be annoying. Another problem is trying to find out what floor the patient is on.

In this embodiment, system 421 can also transmit and receive radio signals. The rescuers then carry a separate portable resuscitator 424 with a receiver unit therein or a separate stand-alone receiver unit 425. Receiver unit 425 provides the responder with the direction to the patient. The direction to the patient is provided by receiver unit 425 in response to information transmitted between system 421 and unit 425.

In accordance with the invention, the radio signal can include data, voice, and or GPS information. In this example, the data information is similar to that discussed above so that the responder has a better idea about the status of patient 102. The voice information is that between patient 102 and responder 426 and/or 427. The GPS information provides a better indication about the location of patient 102 to responders 426 and/or 427. In this way, responders 426 and 427 are guided to the location of patient 102.

In some situations, patient 102 is located in a building which has multiple levels. These buildings can be of many different types, such as a high rise or office building, or a multi-story home, etc. These situations are more complicated because GPS generally provides only its latitude and longitude and does not provide elevation information. The elevation information is useful to have in order to determine which floor system 421 is on. In these situations, it is hoped that system 421 is near patient 102 so that he or she can be located in response to locating system 421.

GPS system 144 can provide elevation information in many different ways. In this example, GPS system 144 provides elevation information by programming it with a default elevation and/or location when system 421 is manufactured. The default elevation can correspond to many different elevations. For example, it can correspond to the elevation of the location of the manufacturer or it can correspond to the location of anticipated use of system 421, if known. The default elevation provides a base elevation in which the elevation of system 421 is determined relative to as it is moved from one GPS location to another. The default location typically corresponds to the location of the position where it is programmed.

Having determined the GPS location, a database of locations and their corresponding elevations is programmed into system 421. When system 421 moves from one GPS location to another it adjusts its elevation indication in response.

There are typically two elevation changes. The first elevation change is a location elevation change which corresponds to the change in elevation when moving from one GPS location to another. The location elevation change generally corresponds changes in the distance of the ground from sea level. This generally varies from one city to another and from one location in a city to another. For example, it can change when going uphill or down hill. These locations are mapped out with changes in GPS location.

The second elevation change is when the elevation changes when at or near a particular GPS location. These elevation changes generally occur when the GPS location does not change or it changes very little. For example, when in an elevator in a building, ones elevation changes if the elevator moves vertically up and down, but ones GPS location does not change very much.

To determine the second elevation change, system 221 includes an altimeter. Altimeters are generally known in the art and determines its elevation relative to sea level. Most altimeters determine elevation relative to sea level based on pressure.

By subtracting the height from the altimeter from the ground elevation obtained from the GPS, a height from ground can be obtained. This information is used to determine the floor of the building that system 421 is located. For example, adjacent floors in a typical building are spaced apart by a distance of eight to ten feet. The specific floor height can be programmed in for a particular building. In other examples, this information is used to determine the approximate floor of the building that system 421 is located.

The height and/or approximate floor information is transmitted to receiver unit 424 and/or 425. In this way, responders 426 and 427 are guided in a multi-story building to the location or approximate location of patient 102. Unit 424 and 425 can calculate the floor number or they can provide the elevation to responders 426 and 427, respectively, so that they can determine it. It is noted that the location finder is not specific to system 421 and finds applicability to a broader range of products, such as but not limited to a medical bracelet or band, etc.

The elevation can be calibrated in several different ways. For example, it can be calibrated when system 421 is manufactured and it can be calibrated by the end user. System 421 can include a recalibration unit which adjusts the indicated GPS location and its corresponding altitude at ground level where this recalibration occurs.

Figure 13A:
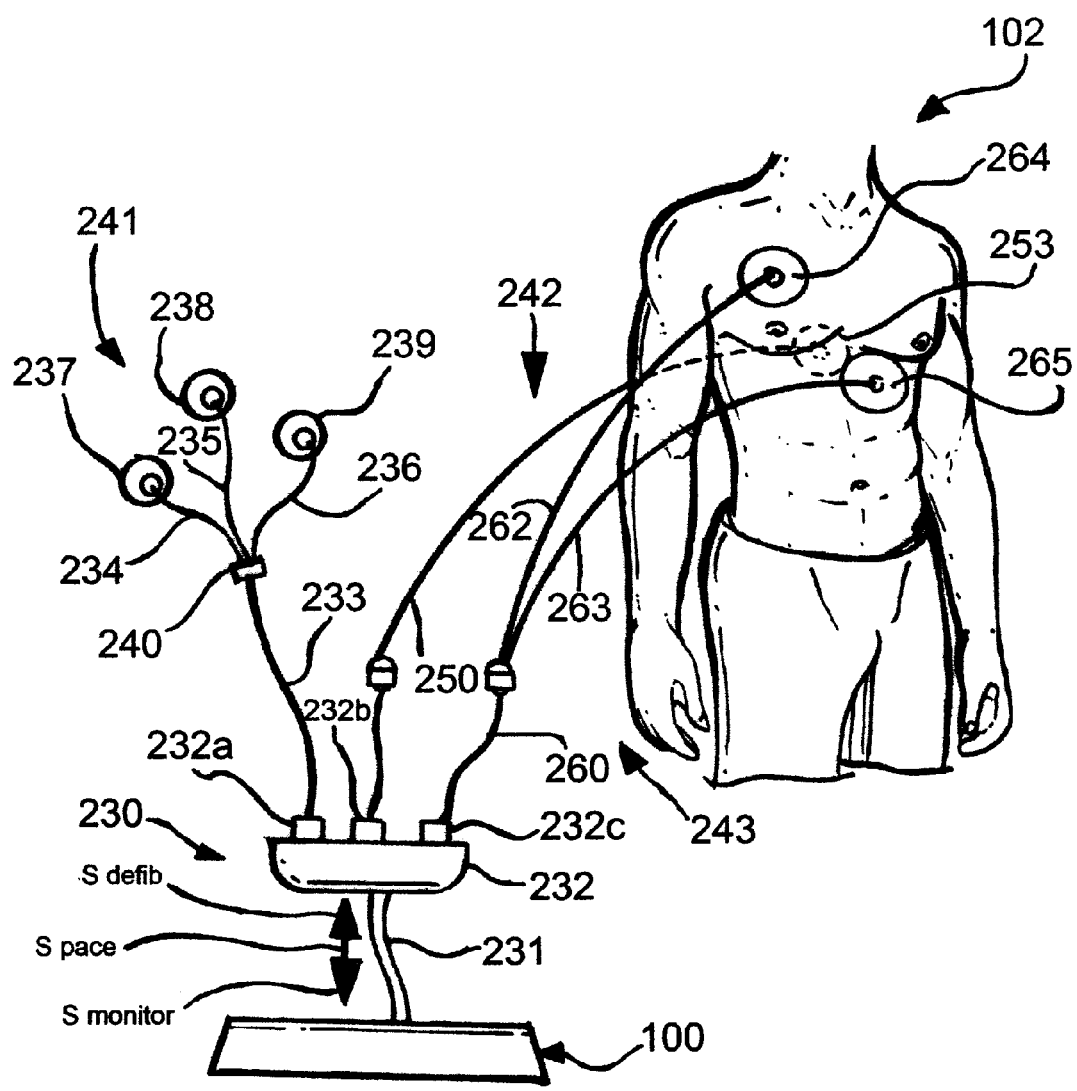
FIG. 13a is a simplified view of the medical system of FIG. 1a in communication with a patient through an electrode system, in accordance with the present invention.

FIG. 13a is a simplified view of system 100 in communication with patient 102 through an electrode system 230, in accordance with the present invention. In this embodiment, system 100 is coupled to an adapter 232 through a cable 231. Adapter 232 includes separate ports 232a, 232b, and 232c and operates to separate different signals flowed through cable 231 by system 100, as will be discussed in more detail below. These signals typically include monitoring, defibrillation, and pacing signals. Monitor, posterior defibrillation, and anterior defibrillation electrode systems 241, 242, and 243 are coupled to ports 232a, 232b, and 232c, respectively. Monitor electrode system 141 flows a monitor signal $S_{Monitor}$ therethrough. Posterior defibrillation and anterior defibrillation electrode systems 242 and 243 flow defibrillation and/or pacing signals $S_{Defib}$ and $S_{Pace}$ therethrough.

Electrode system 230 is useful because defibrillation, pacing, and/or ECG monitoring can be provided to patient 102 with fewer pads if separate electrode pads need to be applied. Normally, there is anterior-anterior placement of the electrodes and if an anterior-posterior placement is desired, then there are four electrodes used-two are at the apex, one is at the sternum, and one at the posterior. However, system 230 uses three electrodes.

This is desirable because often there are a larger number of electrode pads attached to patient 102 to provide defibrillation, pacing, and/or ECG monitoring and the pads can interfere with the operation of the others. This is especially true in situations where two apex electrodes are being used. Further, the space available to couple them to patient 102 decreases as the number of pads coupled to patient 102 increases.

Monitor electrode system 241 is used as an ECG electrode system and includes a cable 233 with one end coupled to port 232a and an opposed end coupled to a splitter 240. Cables 234, 235, and 236 have ends coupled to splitter 240 and opposed ends coupled to electrode pads 237, 238, and 239, respectively. In this example, there are three electrode pads 237, 238, and 238 so that the ECG monitoring can be done using Eindhovein's triangle, which is known in the art.

Posterior defibrillation electrode system 242 includes a cable 250 with one end coupled to port 232b and an opposed end coupled to a posterior electrode pad 253. Posterior electrode pad 253 is positioned on the posterior of patient 102. System 230 improves ECG monitoring by providing better electrical isolation between system 241 and systems 242 and 243. Anterior defibrillation electrode system 243 includes a cable 260 with one end coupled to port 232c. Cable 260 includes cables 262 and 263 which split off from it and have ends connected to anterior electrode pads 264 and 265, respectively.

Monitor pads 237, 238, and 239 are to be positioned (not shown) in a well-known manner on patient 102 so that ECG signals can flow from patient 102 through electrode system 241 to system 100. Posterior electrode pad 253 is positioned on the posterior of patient 102 and anterior electrode pads 264 and 265 are positioned on the anterior of patient 102. Electrode pads 264 and 265 can also provide ECG monitoring. Electrode pads 264 and 265 can also provide a more accurate ECG signal than anterior-posterior electrodes 264 and 253. One reason the ECG signal is more accurate is because there is less noise.

One of the objectives of system 100 is to increase the resuscitation rates of patients so that more lives are saved. The resuscitation rates are increased by system 100 because electrode systems 242 and 243 provide both anterior-anterior electrode pads as well as anterior-posterior electrode pads. It is believed that the anterior-posterior placement of electrode pads provides a better patient survival rate than anterior-anterior placement.

It should be noted that in most emergency situations, the anterior-anterior placement of the electrode pads is typically used first because of convenience and ease of limited trained rescue or lay personnel. The ability to quickly change to anterior-posterior placement of the electrode pads is difficult and time consuming. Anterior-posterior pacing is more useful because the heart responds more to signal $S_{Pacing}$ than if anterior-anterior pacing is used.

It should be noted that cables 233, 250, and/or 260 can be easily attached and detached from connector 232. In this way, the user of system 100 can quickly and easily add or removed systems 241, 242, and 243 to or from system 230. For example, in one situation 241 and 243 are being used and emergency personnel arrives and wants to add 242 to 230. This can easily and quickly be done by attaching cable 250 to port 232b of adapter 232. In previous electrode systems, 230 would have to be removed from patient 102 and replaced with the desired electrode system. However, this takes time and if the procedure is hurried, then mistakes, such as the improper attachment of the electrode pads, are more likely to occur.

Figure 13B:
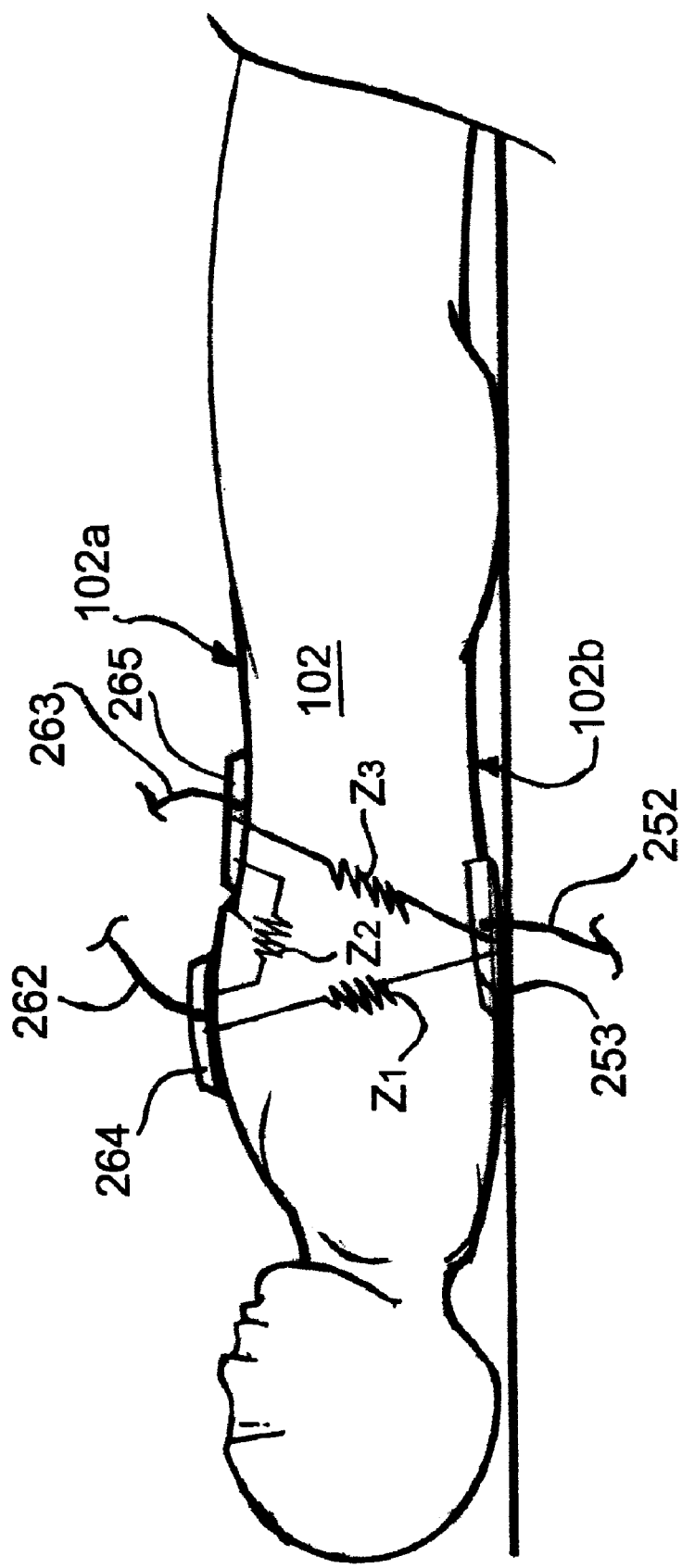
FIG. 13b is a simplified side view of a patient showing an electrode pad positioned on a posterior and electrode pads positioned on an anterior.

FIG. 13b is a simplified side view of patient 102 showing electrode pad 253 positioned on posterior 102b and electrode pads 264 and 265 positioned on anterior 102a. In general, there is an impedance $Z_1$ between pads 264 and 253, an impedance $Z_2$ between pads 264 and 265, and an impedance $Z_3$ between pads 253 and 265. System 100 includes circuitry which determines which electrode pads are coupled to patient 102.

For example, if pads 264 and 253 are coupled to patient 102 as shown, then impedance $Z_1$ is smaller than if one of pads 264 and 253 are not coupled to patient 102. Similarly, if pads 264 and 265 are coupled to patient 102 as shown, then impedance $Z_2$ is smaller than if one of pads 264 and 265 are not coupled to patient 102. Further, if pads 265 and 253 are coupled to patient 102 as shown, then impedance $Z_3$ is smaller than if one of pads 265 and 253 are not coupled to patient 102.

It is well known that the particular values for impedances $Z_1$, $Z_2$ and $Z_3$ varies in response to a number of different factors, such as the body weight of patient 102, skin type, moisture, size of the pad, contact area, pressure, etc. However, if any one of contacts 253, 264, and 265 is not sufficiently coupled to patient 102, then its corresponding impedance $Z_1$, $Z_2$ and $Z_3$ will be significantly larger. In this way, system 100 can determine whether or not pads 264, 265, and 253 are coupled to patient 102.

In FIG. 13a, there are several advantages provided by electrode system 230. One advantage is that there is electrode redundancy so that if one electrode system fails, then system 100 can use another electrode system instead. For example, if defibrillation is being provided to patient 102 between pads 264 and 265 and pad 265 fails, then system 100 can determine this by a change in impedance $Z_2$ and provide defibrillation between pads 264 and 253 instead. Pad 265 can fail in several ways, such as by decoupling from patient 102. In another example, if defibrillation is being provided to patient 102 between pads 264 and 253 and pad 253 fails, then system 100 can determine this by a change in impedance $Z_1$ and provide signal $S_{Defib}$ between pads 264 and 265 instead. Pad 253 can fail in several ways, such as by decoupling from patient 102. This can happen for the pacing signal too.

It is known that medical personnel prefer to provide one protocol rather than another in certain situations. For example, some medical personnel prefer anterior-anterior defibrillation and pacing as opposed to anterior-posterior. An advantage of electrode system 230 is that it allows both of these protocols and others to be used as chosen by the end user. Another advantage is that this choice can be made without having to remove electrode pads already in place, which saves time and lives.

As discussed above, system 100 includes circuitry which determines the particular arrangement of the electrode pads to patient 102 and provides the corresponding protocol. For example, if system 100 determines that pads 253 and 264 are coupled to patient 102 as shown in FIG. 13b, and pad 165 is not, then system 100 provides the protocol for anterior-posterior pacing and/or defibrillation. In another example, if system 100 determines that pads 264 and 265 are coupled to patient 102 as shown in FIG. 13b, and pad 253 is not, then system 100 provides the protocol for anterior-anterior pacing and/or defibrillation. This is desirable because the protocols for anterior-anterior pacing and anterior-posterior pacing and defibrillation are often different from each other. For example, they can use different signals values, pulse widths, and/or sequences, as will be discussed in more detail below.

There are several protocols which can be used with systems 100 and 230 to provide defibrillation, pacing, and/or ECG monitoring to patient 102. In a first protocol, defibrillation is provided by flowing signal $S_{Defib}$ between pads 264 and 265 and pacing is provided by flowing signal $S_{Pace}$ between pads 264 and 253. Further, signal $S_{Monitor}$ is flowed between pads 264 and 265. In this example, cardiac pacing is more effective when provided by electrodes 264 and 253 (anterior-posterior) rather than 264 and 265 (anterior-anterior). Also, anterior-posterior pacing in this first protocol is desirable because then pads 264 and 265 can be used for ECG monitoring.

If patient 102 is being defibrillated using pads 264 and 265 then system 100 will determine that impedance $Z_2$ is small and impedances $Z_1$ and $Z_3$ are large. When pad 253 is coupled to patient 102 at a later time, then system 100 will determine that impedances $Z_1$ and $Z_3$ become smaller to indicate the placement of pad 253.

In a second protocol, signals $S_{Defib}$ and $S_{Pace}$ are flowed between pads 264 and 253. In this second protocol, signal $S_{Monitor}$ is flowed between pads 264 and 265. This is desirably because signal $S_{Pace}$ can undesirably interfere with signal $S_{Monitor}$ if they are both flowed between pads 264 and 265. This can happen for several reasons, such as heart polarization and depolarization effects. Since, in this protocol, pad 265 is not used for pacing and defibrillation, ECG monitoring is substantially relieved of this problem.

In either of these protocols and others, posterior electrode 253 can operate as a current return for electrode systems 241 while electrode pads 264 and 265 flow defibrillation and/or pacing signals.

Electrode 253 can also operate as an ECG reference electrode for electrodes 264 and 265 providing more stability and clinical validity for ECG monitoring. In this instance, a major advantage is provided if 264 and 263 are used for stimulus, then better isolation is provided when using 264 and 265 for ECG monitoring.

Two electrodes should be used to monitor the heart. Pace-defib using anterior posterior and monitor using anterior anterior. When doing monitoring, use the posterior as a ground in place of a right leg electrode, which is usually the ground electrode.

Figure 13C:
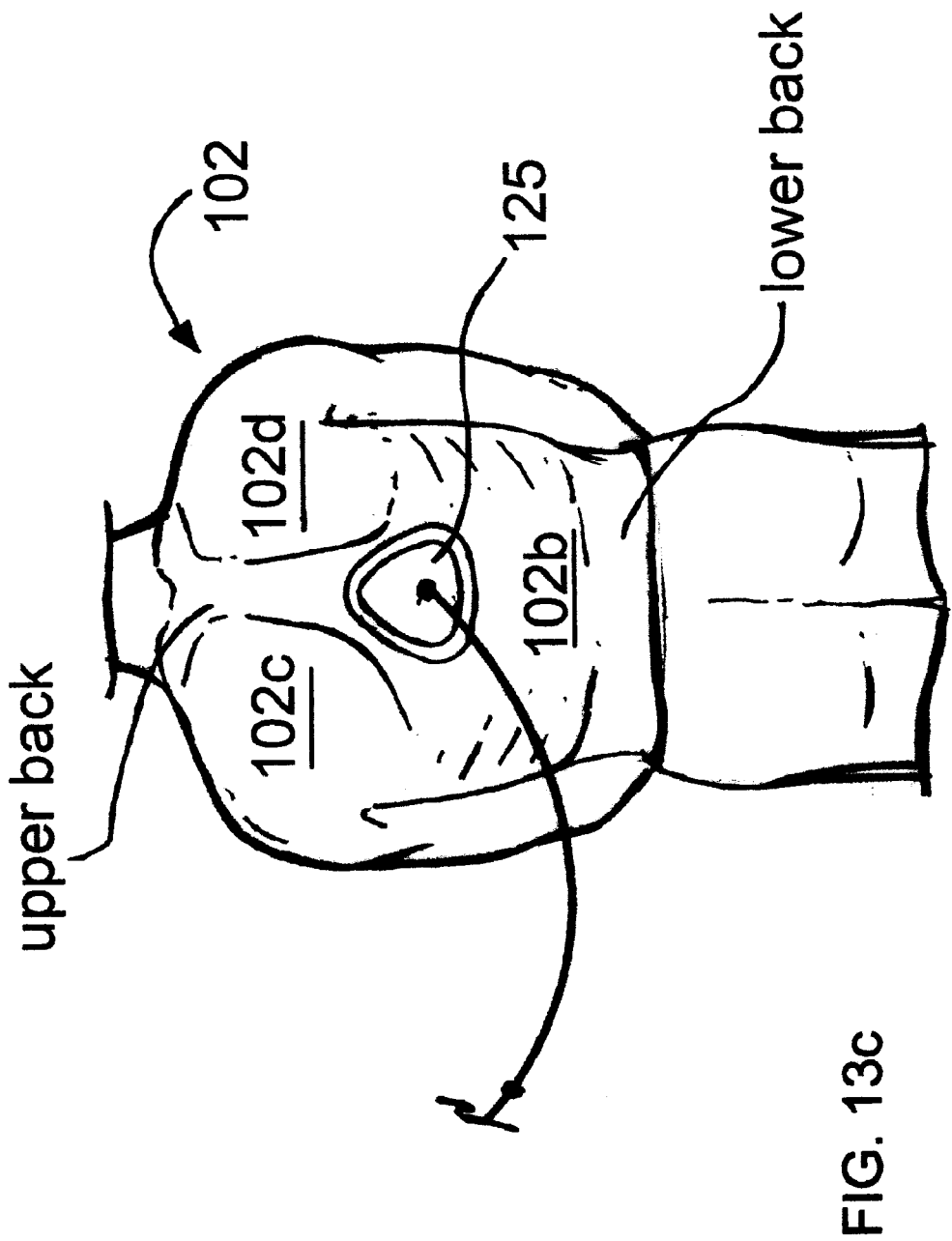
FIG. 13c is a simplified view of a posterior of a patient with a posterior electrode pad connected thereto, in accordance with the present invention.

FIG. 13c is a simplified view of posterior 102b of patient 102 with a posterior electrode pad 125 in accordance with the present invention. Pad 125 is used in a manner similar to electrode pad 253 discussed above. In this embodiment, pad 125 is ergonomic in shape and dimensioned so that it extends between left and right scapula 102c and 102d of patient 102. Pad 125 is dimensioned to extend between scapulae 102c and 102d so that it can be positioned easier and faster. Pad 125 is also dimensioned to cover more of the conductive area between scapulae 102c and 102d to increase the likelihood that the heart of patient 102 responds to a signal flowed therethrough pad 125. The signal can be of many different types, such as a defibrillation stimulus signal and/or a pacing stimulus signal, provided by a defibrillator the same or similar to defibrillator 104 discussed above.

Pad 125 can be constructed of many different types of materials and have many different structures. In this embodiment, pad 125 preferably constructed of an adhesive material, such as foam, foil, and gel, hydro-gel, or hydro-adhesives. Pad 125 typically has a pre-connected wire and a low profile. Extreme ease of use and placement is achieved by simplified training and deployment. Having a larger conductive area produces ultra low impedance to electrical current flow.

Pad 125 is preferably triangularly shaped and placed covering both upper left and right side of the back of patient 102 such that there is an increased usable contact area. Pad 125 provides several advantages. One advantage is that it placement can be placed higher on back 102b to reduce the amount of impedance between it and the heart of patient 102. One reason the impedance is reduced is because the distance between the heart and pad 125 is reduced. Another reason the impedance is reduced is because pad 125 is dimensioned to have a larger area. A further advantage of pad 125 is that it can be positioned easier and more accurately because of its larger dimension. This is beneficial since it is usually positioned in a hurry during an emergency. This placement also corresponds to windows of higher conductivity to externally applied shocks.

Figure 16:
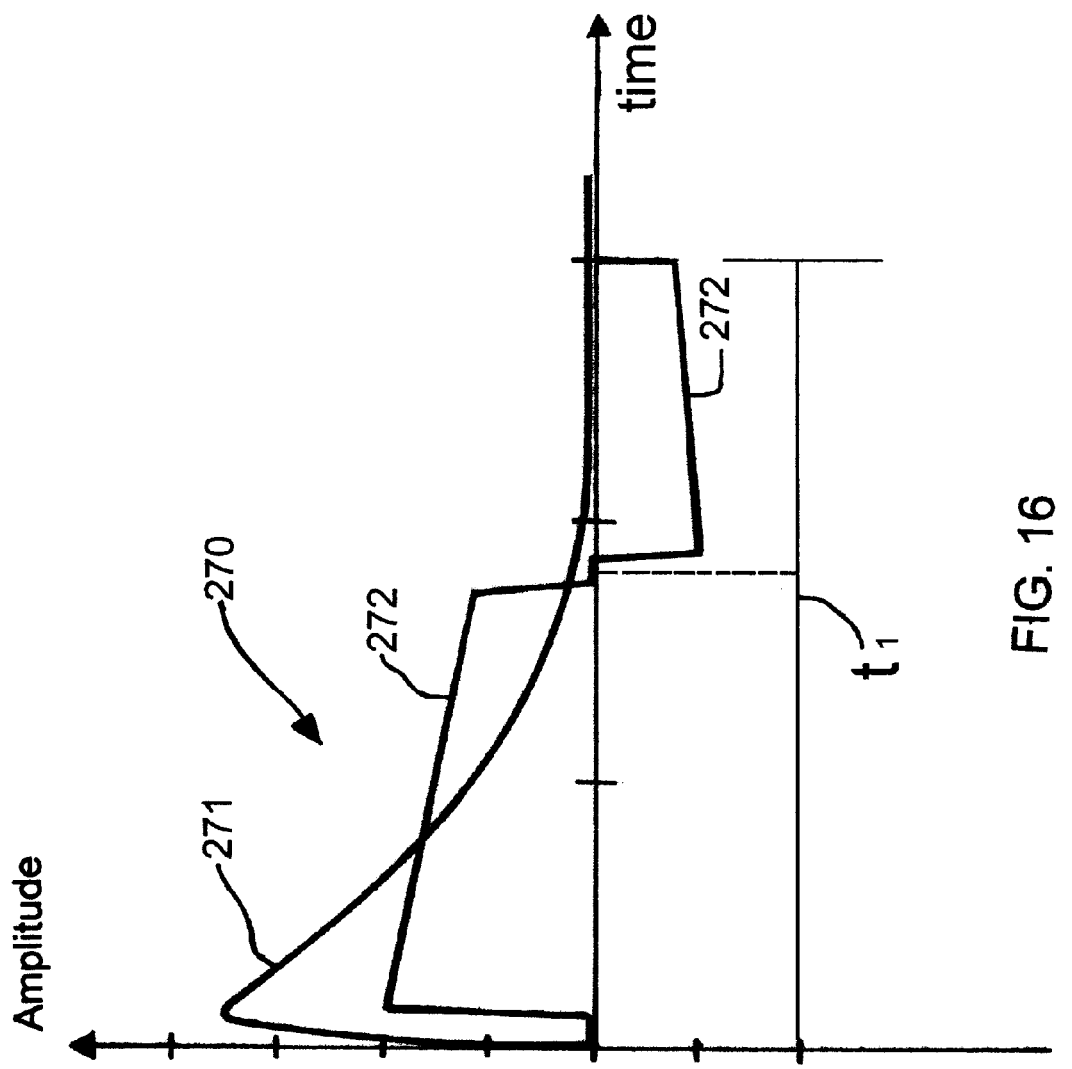
FIG. 16 shows a graph of several examples of defibrillation signal as a function of time.

FIG. 16 shows a graph 270 of several examples of defibrillation signal $S_{Defib}$ as a function of time. Defibrillation signal $S_{Defib}$ can have many different waveforms and be monophasic and multiphasic. Many defibrillation waveforms are monophasic, such as signal 271, with signal $S_{Defib}$ flowing from one electrode to another in one direction. In signal 271, the amplitude increases to a value and then decays exponentially thereafter. The amplitude typically has units of volts or amps. In one particular example, signal 271 increases from zero volts to about 3000 volts in around 2 milliseconds. It then exponentially decays to zero volts in about another 10 milliseconds. In this current, the current is about 60 amps when the amplitude is 3000 volts.

Another type of waveform is biphasic, such as signal 272, with signal $S_{Defib}$ flowing between electrodes in one direction and then in the opposite direction. In signal 272, the amplitude increases to a value and then switches polarity after a certain amount of time has elapsed. In one particular example, signal 272 increases from around zero volts to about 1600 volts. The amplitude then decreases linearly to about 1400 volts after about 10 milliseconds. The amplitude then switches polarity to about minus 1500 volts. The amplitude increases linearly to about minus 1300 volts after about another 10 milliseconds. For signal 272, the current is about 20 amps when the amplitude is 600 volts and the current is about 15 amps when the amplitude is 400 volts.

In these examples, the amplitude corresponds to the voltage of the signal. In order to provide the desired voltage amplitude, the current is adjusted in response to changes in the impedance to provide it, as determined by Ohm's law. In other examples, however, the amplitude corresponds to the current of the signal. In order to provide the desired current amplitude, the voltage is adjusted in response to changes in the impedance to provide it. This is also as determined by Ohm's law. In most defibrillators, the signal amplitude corresponds to the voltage and not the current of the signal.

In one example in accordance with the present invention, the defibrillation and/or pacing signals are provided with much smaller amplitudes and much longer durations, interval $t_1$ is between about 0.04 seconds and 10 seconds and preferably about 1 second. Further, the amplitude of signal $S_{Defib1}$ is between about 100 volts and 1000 volts with a current between about 50 amps and 300 milliamps. The particular signal time interval and amplitude is chosen so that signal $S_{Defib1}$ reduces the amount of fibrillation of the patient's heart. Preferably, the particular signal time interval and amplitude is chosen so stop the patient's heart from fibrillating.

In accordance with the invention, the defibrillator, such as defibrillator 104 discussed above, provides several different protocols which are user selected. These protocols relate to the defibrillation and/or pacing signals $S_{Defib}$ and $S_{Pace}$ that are provided to the patient. This is useful because the end user has more flexibility in choosing which protocol is used.

Figure 17:
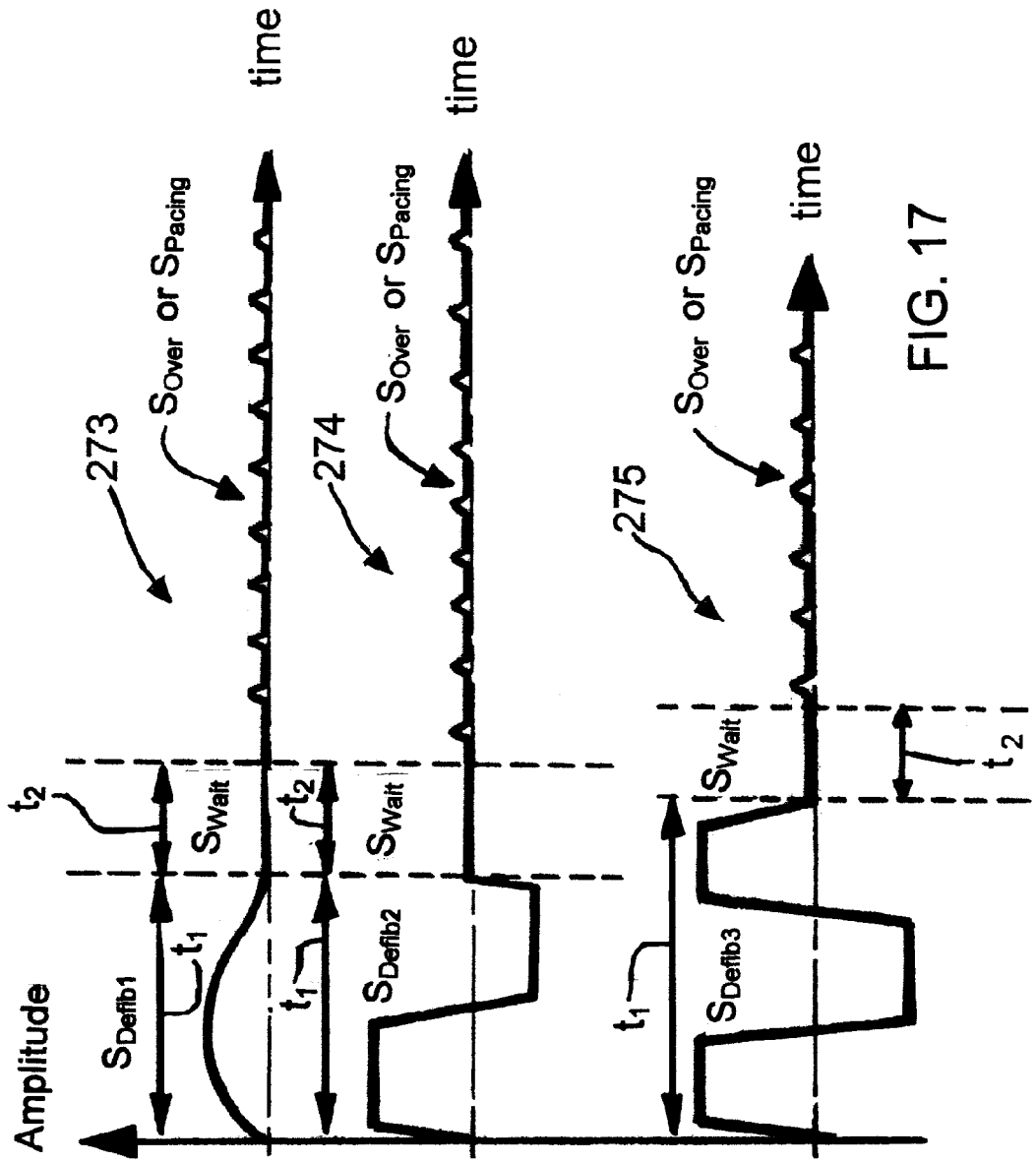
FIG. 17 is a graph showing several different waveforms that can be provided by a defibrillator to a patient.

FIG. 17 is a graph showing several different waveforms that can be provided by the defibrillator to the patient. In a waveform 273, signal $S_{Defib1}$ is provided between a time interval of $t_1$. In this particular example, signal $S_{Defib1}$ is monophasic. If interval $t_1$ is one second, then defibrillator 104 can be calibrated easier for a more accurate current discharge. During a time interval of $t_2$, a signal $S_{Wait}$ is provided. In this example, signal $S_{Wait}$ has an amplitude of zero and is included so that the heart of the patient can get to the end of its refractory period. Hence, interval $t_2$ is chosen to correspond to the heart's refractory period. In other examples, signal $S_{Wait}$ can have other non-zero values, but these non-zero values are preferably chosen so that the heart is not refibrillated or starts electrically "ringing". Signal $S_{Pacing}$ or $S_{Over}$ is provided in an interval $t_3$. Signal $S_{Pacing}$ corresponds to a pacing signal and signal $S_{Over}$ corresponds to an over-drive pacing signal. Signals $S_{Over}$ and Spacing are generally pulses provided at a particular frequency, with the frequency of signal $S_{Over}$ being greater than the frequency of signal $S_{Over}$. These pulses are typically square, but they can have other shapes. Ringing from the defibrillation signal can cause ringing in interval $t_2$.

FIG. 17 also shows waveforms 274 and 275 which are similar to waveform 273 discussed above. One difference, however, is that waveform 274 and 275 have signals $S_{Defib2}$ and $S_{Defib3}$ during time interval $t_1$. Signal $S_{Defib2}$ is a biphasic signal in this example and signal $S_{Defib3}$ is triphasic. It should be noted that time interval $t_2$ is after interval $t_1$ and before interval $t_3$. It should also be noted that the amplitude of the various signals shown in FIG. 17 can have units of volts or amps, as discussed above in more detail with FIG. 16.

If the signals shown in FIG. 17 have units of volts, then defibrillation and pacing are provided by adjusting the signal current to provide a desired voltage and the defibrillator operates as a voltage source. If the signals shown in FIG. 17 have units of amps, then defibrillation and pacing are provided by adjusting the signal voltage to provide a desired current and the defibrillator operates as a current source.

It should be noted that in some examples, time intervals $t_1$, $t_2$, and $t_3$ can overlap with each other. For example, the time near the end of time interval t1 can overlap with the time near the beginning of time interval t2. Further, the time near the end of time interval t2 can overlap with the time near the beginning of time interval t3.

It should be noted that in some situations, the patient will be revived during or after time interval t1. For example, the patient can be revived during time intervals t2 or t3. The patient is usually revived during or after time interval t1 in response to the signal provided therein. In these situations, it is generally undesirable to provide another signal, such as signals SDefib1, SDefib2, SDefib3, SPacing, and SOver, to the patient.

In some embodiments, it is desired to provide the signal with units of amps so that the defibrillator operates as a current source. An advantage of this is the current provided to the patient is more accurately controlled. Another advantage is that the current provided is less dependent on the impedance of the patient and the electrodes used to provide the signal.

Most defibrillators provide defibrillation signals wherein time interval $t_1$ is 5 milliseconds to 200 milliseconds. However, a problem with this is that the electronic circuitry needed to provide these signals is expensive and more difficult to control, especially if the signal has a voltage amplitude of over 1500 volts, as is often the case. By using the defibrillator to provide signals with time interval $t_1$ being greater than about 0.04 seconds and 10 seconds, and the voltage and current amplitude below about 1000 volts and 50 amps, respectively, less costly electronic circuitry is needed and the signals are easier to control. One way in which a signal is easier to control is if its shape is better controlled.

After time interval $t_1$, the patient is monitored to determine his or her vital signs. This is often done with a monitor similar to monitor 107. The vital signs often provide information about the operation of the heart. For example, the vital signs can indicate arrhythmia, asystole, tachyarrhythmia, and/or fibrillation. It is believed that very high rate arrhythmias cannot be detected because only bipolar electrodes are used almost exclusively for monitoring. A complex vector-cardiograph might be able to isolate these complex ECG heart signals but only with some difficulty.

In response to the operation of the patient's heart, the defibrillator provides the appropriate signals to the patient.

For example, if the monitor indicates that asystole is occurring, then the defibrillator provides one of waveforms 273, 274, and 275 (FIG. 17), as chosen by the user, wherein signal $S_{Pacing}$ is provided in time interval $t_3$. If the monitor indicates that tachyarrhythmia or fibrillation is occurring, then the defibrillator provides one of waveforms 273, 274, and 275 (FIG. 17), as chosen by the user, wherein signal $S_{Over}$ is provided in time interval $t_3$.

Time interval $t_2$ is provided so that the pacing and defibrillation signals are synchronized to reduce the likelihood of providing a defibrillation or pacing signal to the heart before it is at its end of its refractory period. It is more preferably to provide the defibrillation or pacing signals at the end of the refractory period. One reason for this is to give the heart time to repolarize. The pacing and defibrillation is preferably done in response to each other so that these signals are less likely to damage the heart. These signals can damage the heart if they are provided while the heart is in a particular phase of beating. The damage can cause fibrillation or arrest, for example.

Figure 18B:
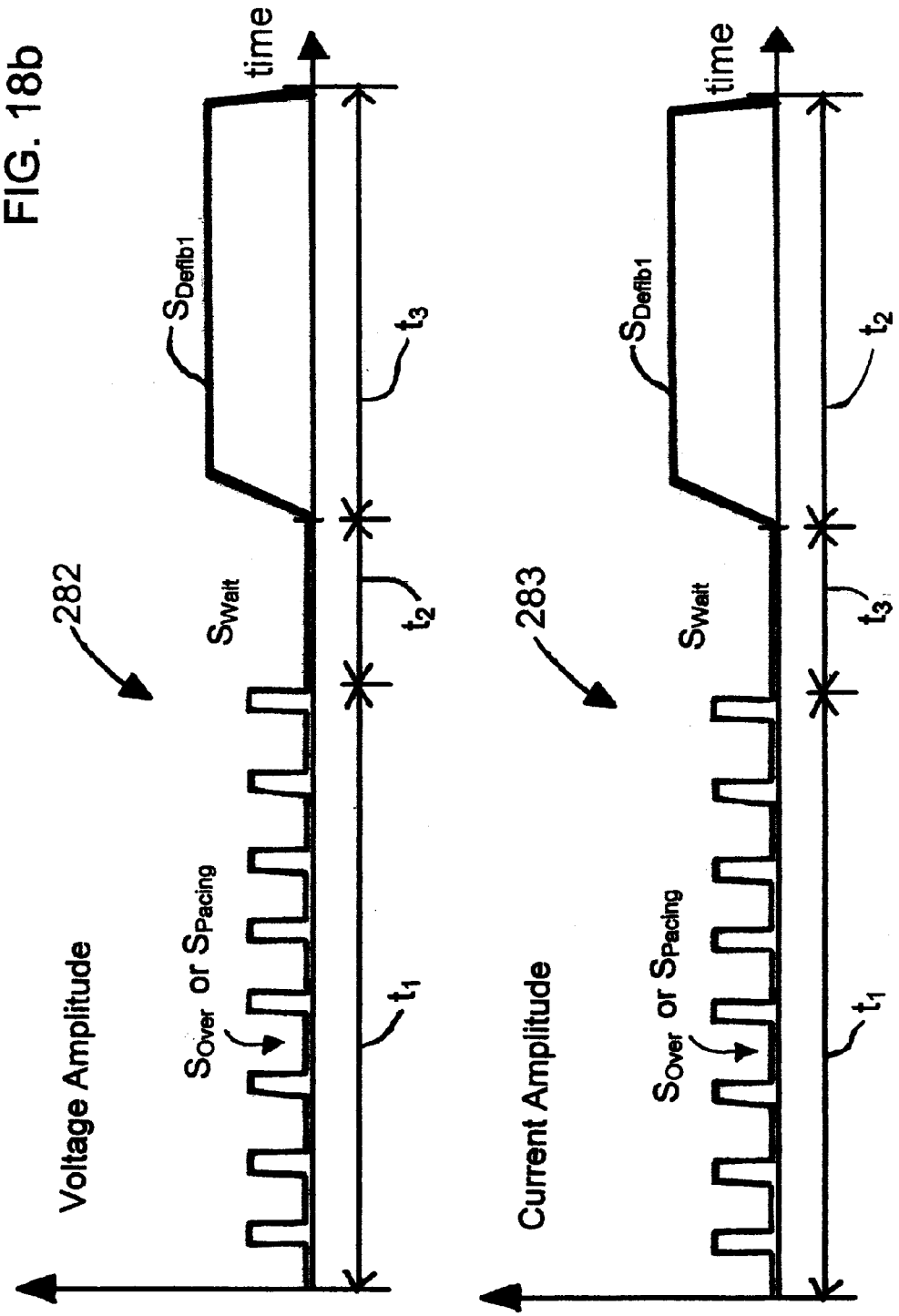

FIGS. 18a and 18b are simplified graphs of various waveforms in accordance with the present invention. FIG. 18a shows waveforms 280 and 281 and FIG. 18b shows waveforms 282 and 283. Waveform 280 has a voltage amplitude and includes monophasic defibrillation signal $S_{Defib1}$ in time interval $t_1$, signal $S_{Wait}$ in time interval $t_2$, and signals $S_{Over}$ or $S_{Pacing}$ in time interval $t_3$. Waveform 281 is similar to waveform 280 except it has a current amplitude instead of a voltage one.

In FIG. 18b, waveform 282 has a voltage amplitude and includes signals $S_{Over}$ or $S_{Pacing}$ in time interval $t_1$, signal $S_{Wait}$ in time interval $t_2$, and monophasic defibrillation signal $S_{Defib1}$ in time interval $t_3$. Waveform 283 is similar to waveform 282 except it has a current amplitude instead of a voltage one. It should be noted that in other examples, signal $S_{Defib1}$ can be replaced with a multiphasic signal, such as $S_{Defib2}$ and $S_{Defib3}$ shown in FIG. 17.

Figure 14:
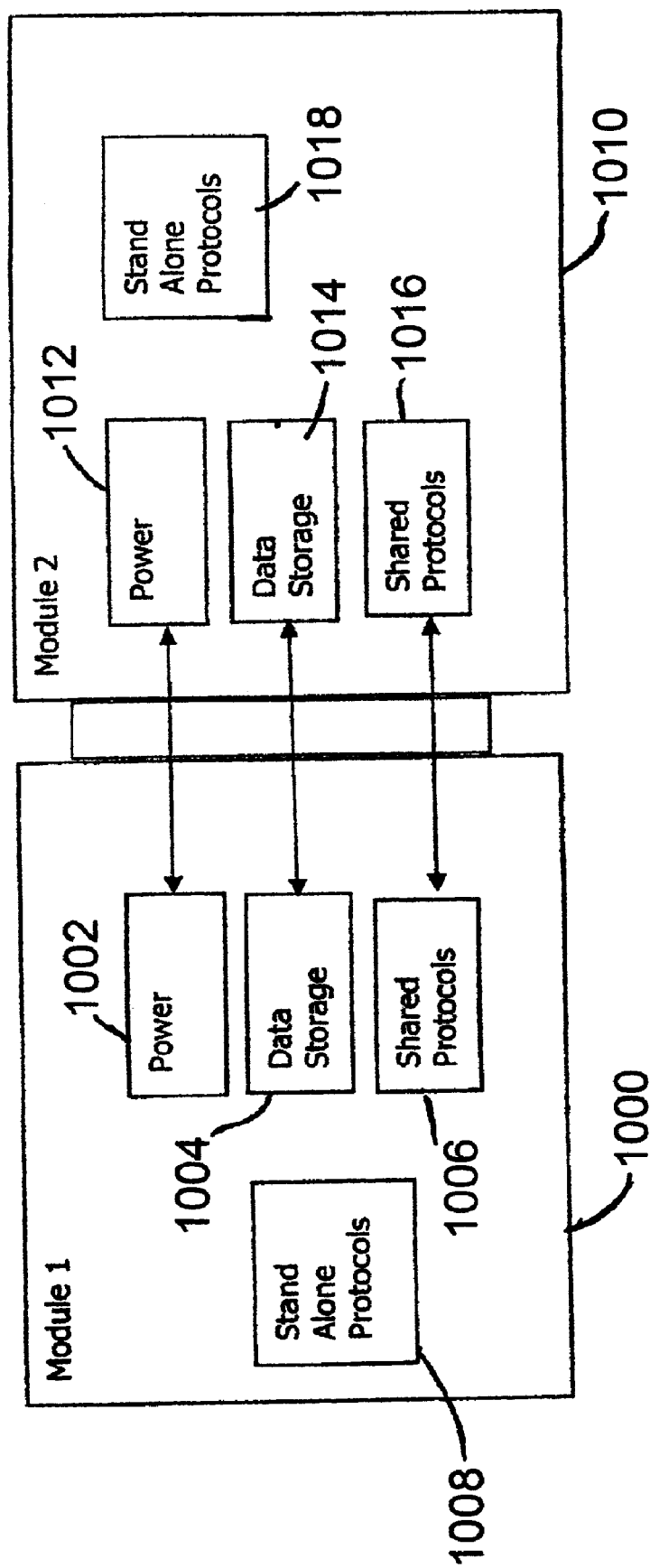
In FIG. 14, show two modules which are interconnected, in accordance with the present invention.

In FIG. 14, two modules 1000 and 1010 are interconnected. When the modules are interconnected power 1002 and 1012; data 1004 and 1014; and protocols 1006 and 1016 are shared and used between the multiple modules. However, the modules may include separate set of protocols 1008 and 1018 used when the modules are not connected.

The modules may also contain connections 'both sides' so they may be arranged by users or rescuers in the desired order without compromising communications between modules. The modules will share battery power among themselves when plugged together. The modules will share external power if one of them is acquiring it. Dual communications will 'conference call' with hands-free is also provided. If modules are plugged together they will record call and actions into a central module. If used separately they will record into only the separate module. Mechanically the cases of each module may have slide in storage cases that fit on them, perhaps on the back, which will also function as connectors for air or electricity. These may be disposable or reusable. In other words the cases function as both storage box and connector for the materials inside the storage box. When storage boxes are stored upon the back of the units the modules will have openings mechanically upon the top of each module, when needed, to hold wires or breathing circuits out of the way of the displays of each unit. If modules are plugged into central module (AED perhaps) then the audio system in that module may be used for by docked modules for the sake of efficiency and reduced costs over using audio modules in each module separately.

Figure 15A:
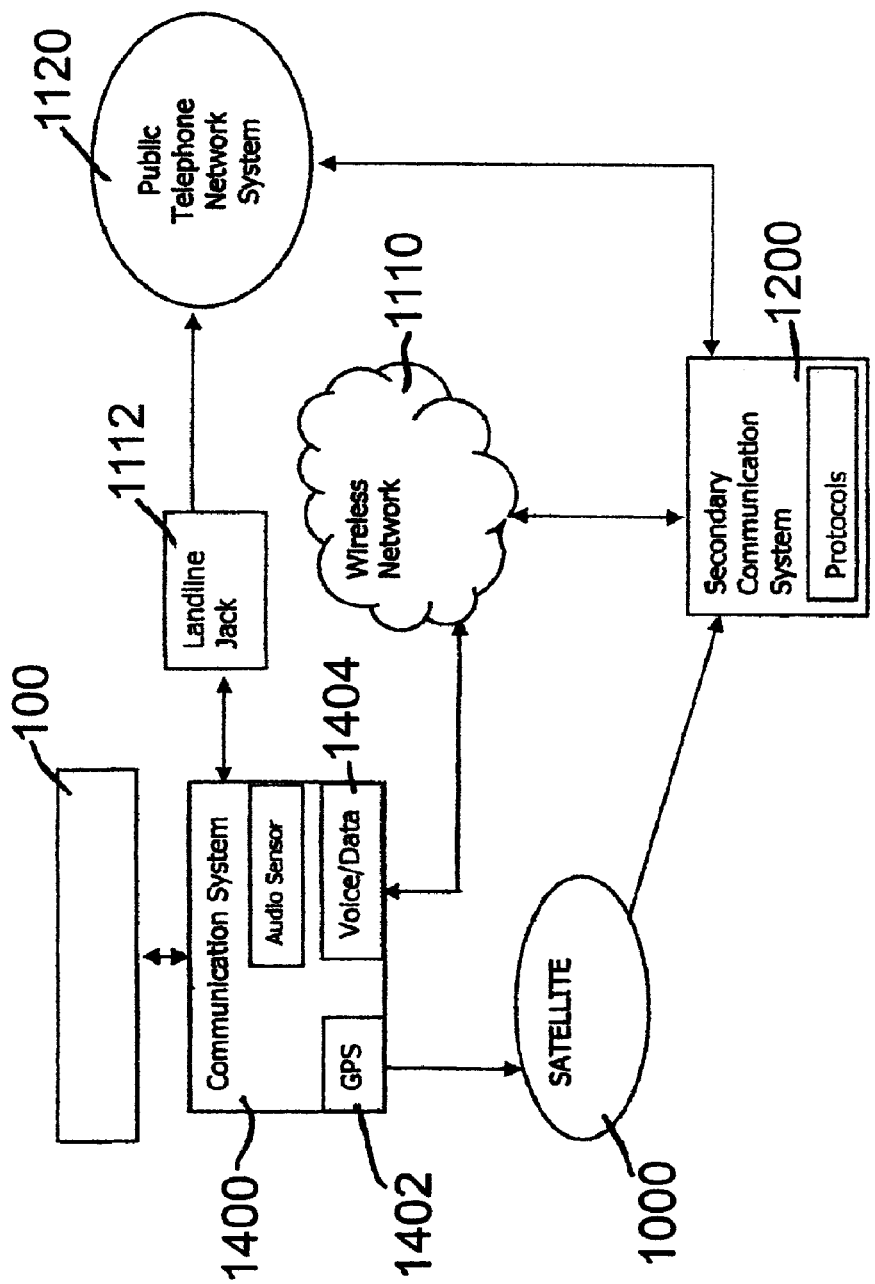
FIGS. 15a, 15b, and 15c show various embodiments of communication systems in accordance with the present invention.
Figure 15B:
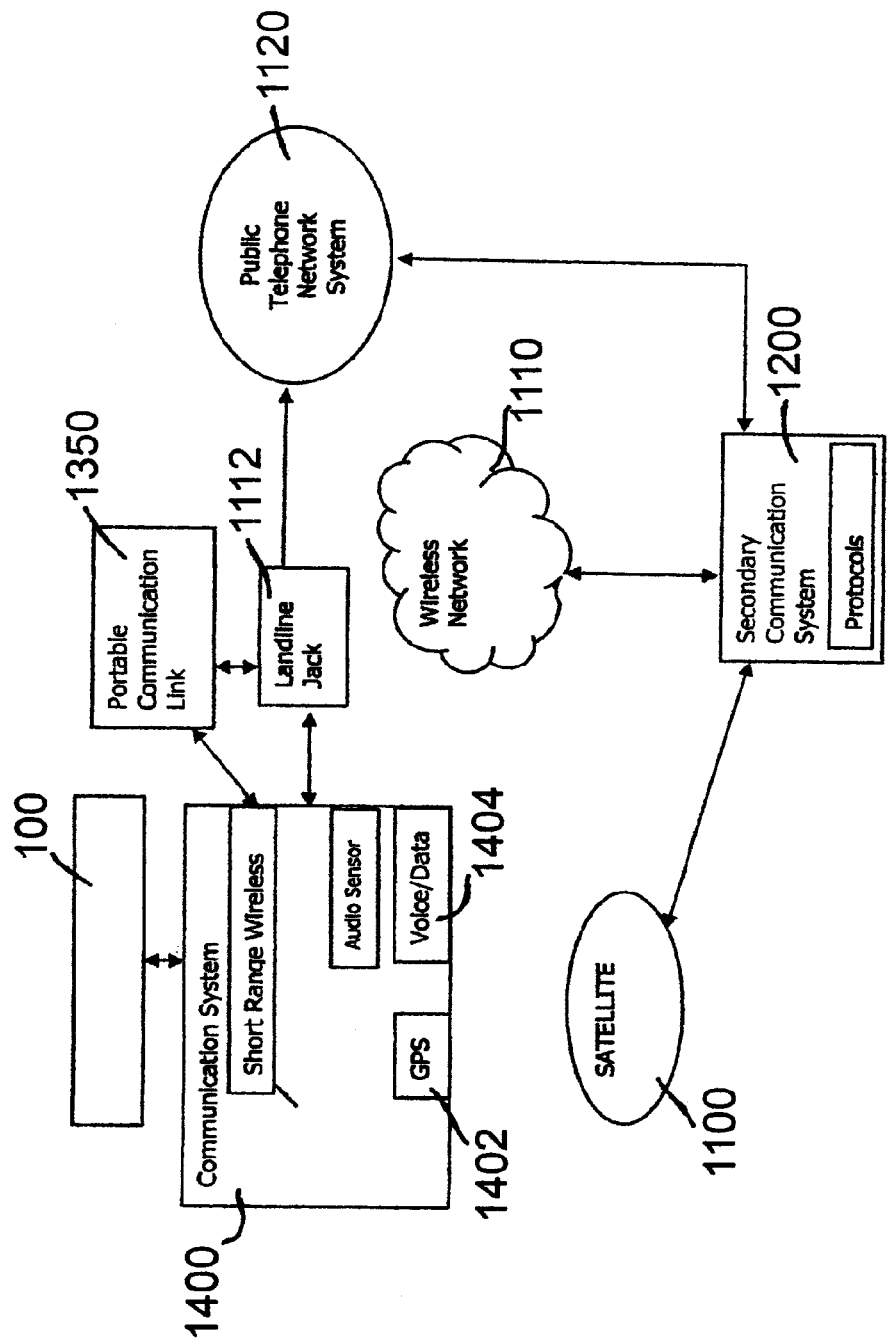

As illustrated in FIG. 15a, system 100 can include a communication system 1400 (or is attached to a telecommunication module). The communication system 1400 includes a GPS communication link 1402 to communicate with a satellite 1100. The communication system 1400 also includes a voice/data wireless link 1404 to communicate with a wireless network 1110. The communication system 1400 includes a link to secure to a landline jack 1122 to communicate with a Public telephone network system 1120. The communication system 1400 may include any or each of these communication links. Each link would further communicate with a secondary emergency system 1200 (such as but not limited to an emergency center, hospital, medical personnel, rescuer, third party, or medical center. The secondary emergency system 1200 may include protocols and/or software to communicate and/or control the resuscitator 100 or other modules secured thereto. In other embodiments discussed in greater detail below, see FIG. 15b, the communication system 1400 may include a short range wireless communication 1300 to communicate with a portable communication link 1350 (referred to below as the detachable battery operated portable communications link 1416). The communication link 1350 is plugged into a landline jack 1112 to communication with a public telephone network system 1120 to the secondary communication system 1200. This may be needed when the communication with a satellite and wireless networks are unavailable.

Figure 15C:
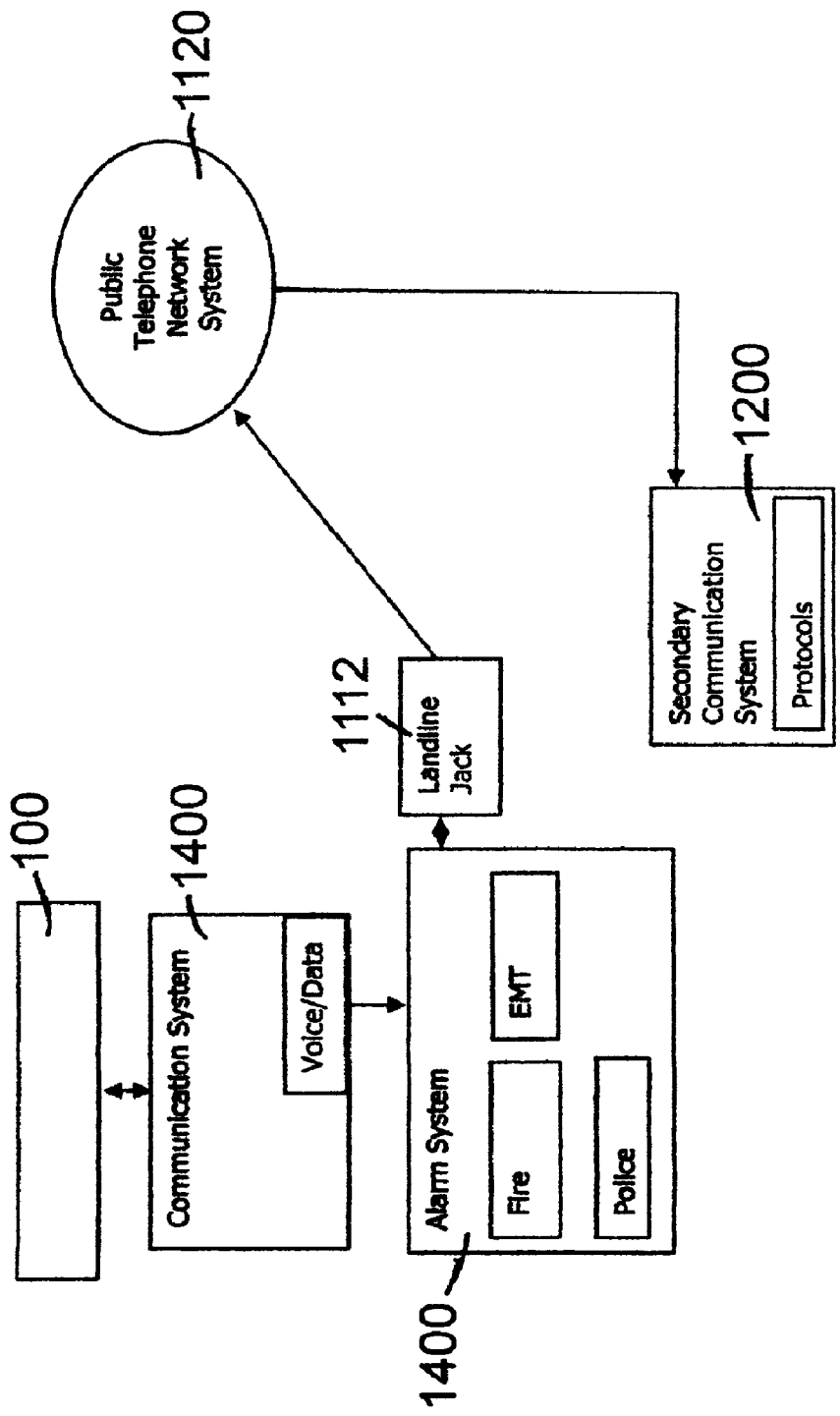

FIG. 15c shows resuscitator 100 with communication system 1400. The communication system 1400 is in communication with an alarm system 1400. The alarm system 1400 is attached to a landline such that communications from system 100 will notify EMT personal monitoring from the secondary communication system 1200.

While in the resuscitator 1410, the portable communications link 1416 includes a battery that charges while the main resuscitator battery is charged. When the portable communications link 1416 is needed, it is then taken out of the resuscitator and carried to a phone line and plugged in thereto with an RJ 11 jack 1420. It will function on its pre-charged batteries, but may also include an external conventional AC adaptor plug 1422. The resuscitator 1410 is designed to automatically attempt connection through the portable communications link 1416 and should a dial tone or confirmation of the connection occur, it will dial its appropriate number or numbers for establishing a voice and/or data connection.

In summary, the present invention thus provides for an AED with a built-in or interconnected ventilator system and/or a built-in APRV ventilation system. The APRV ventilator is preferably portable and would include its own battery pack. The APRV ventilator further includes the ability to detect if a pressure drop off or leak in the ventilation system occurs and is able to increase flow automatically to compensate for the leak or pressure drop. The AED preferably has software that causes the ventilator to pause, or wait for peak expiration to discharge the defibrillator, and/or to produce a negative airway pressure during countershock.

The ventilator disclosed herein also may use electrically controlled micropumps in on/off modes to control ventilation pressure and flow without a regulator. The pumps are piezoelectric pumps which helps save battery power. An inline venturi flow booster may be used to boost pressure and/or flow in the ventilator. The pumps are miniaturized and usually used to cool circuit boards. In one example, ten pumps can be positioned on a circuit board. For half the possible pressure, only five are turned on. For more pressure, more pumps are turned on and for less pressure, more pumps are turned off. These pumps are generally more accurate in controlling the amount of flow. The pumps are normally off when not needed to save battery power. In other examples, a control circuit is used to control, regulate, and maintain pressure which would use more power.

The ventilator would also use positive pressure and monitor oxygen content in a closed circuit and would further bleed $O_2$ in only when needed to maintain $O_2$, but also prolong $O_2$ storage efficiently. The ventilator would also maintain a high level or high percentage of $O_2$ if patient is detected in respiratory or cardiac arrest. The system would also maintain ventilator $O_2$ and air-flow relative to detected number or frequency of patient breaths to preserve $O_2$ and battery power. Internal chamber or tank for storage of pressurized oxygen or air with optional recharging by internal pump(s) (piezoelectric) while batteries are charged. As mentioned in previous embodiments (FIG. 4) the ventilator module 120 may include removable packets 130 with O2 bottles or simply removable O2 bottles for fast replacements of oxygen supply. System can include an extra oxygen bottle with a fast change mechanism in case it is needed. The ventilator may utilize pulse oximeter or similar sensor to detect arterial oxyhemoglobin saturation and then regulate use of oxygen in the breathing circuit to preserve oxygen supplies and/or monitor and automatically adjust ventilation based upon the patient's needs. An oxygen membrane generator could be built into the ventilator such that the oxygen may be recharged at same time the batteries are recharged. Regulate the flow of oxygen based on the condition of the patient. There are oxygen generators which take oxygen out of the air. Recharge the batteries as well as the oxygen.

Software and hardware is used for monitoring patient 102 and determining cardiac arrest and well as for controlling the ventilation system for hyperventilation.

A medical system is disclosed which provides an "intelligent" instrument to adapt to optimal electrode or sensor system coordinating behavior of each. It may be extended for example, when separate ECG monitoring electrodes are applied then they might be used as a preferential monitoring path over the other electrodes. In the medical field separate electrodes or sensors may be applied for each procedure. Multifunctioning electrodes may exist in separate locations. This would allow an instrument to automatically choose to use the most desired pathway.

Therefore, a low amplitude defibrillator or overdrive demand pacing unit could make obsolete all defibrillators currently on the market. This also means that implantable devices should be redesigned, although many use overdrive pacing already for tachyarrhythmias. This aspect of the present invention finds applicability in implantable invasive cardiac defibrillators as well as the external nonportable and portable defibrillators.

The defibrillator preferably includes circuitry that monitors the impedance of the patient through the defibrillation electrodes and adjusts the defibrillation and/or pacing signals in response. In some examples, the defibrillator adjusts the frequency of the pacing signal until there is "heart capture".

Since defibrillators used today do not utilize pacing as a part of or following defibrillation, it is contemplated by the present invention to include a unit that also includes pacing, which would aid the original defibrillation pulse in causing successful defibrillation of the heart. If the heart does not produce its own contractions, then the heart standstill, which may follow a defibrillation shock, would require pacing anyway.

This novel approach would immediately institute this in its normal functions, a totally novel approach. This is essentially defibrillation aided by immediate overdrive or regular pacing, a unique methodology. The current methodology is to simply defibrillate over and over.

After which, the unit waits for repolarization of the patient or a refractory period of the patient's heart. After the refractory period the invention will begin to apply a pacing pulse of about 75 milliamps for 0.040 seconds duration. The pacing pulse may continue while the unit monitors the patient. The unit will automatically stop the pacing pulses if spontaneous pulses occur from the patient. This is to avoid a second defibrillation signal. We want a continuous recovery period. The purpose of this embodiment is to enable production of very small low cost defibrillator pacers or automatic external defibrillators (AED) so they may be used in many public access programs.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

I claim:

1. A system for providing life support to a patient, comprising:
   a communication system being removably attached to either a defibrillator and/or a ventilator, the communication system having dual communication links, defined as primary communication and secondary communication links, each of the primary and secondary communication links having a transmitter and a receiver for sending and receiving voice and/or data information obtained from the defibrillator and/or ventilator to separate external communication systems, and the primary communication link having the means for controlling the secondary communication link such that the primary communication link in communication to a first external communication system can control the secondary communication link to initiate contact to a second external communication system.

2. The system of claim 1, further including a global positioning system for providing a location of the system.

3. The system of claim 1, wherein the communication system includes a phone.

4. The system of claim 1, further including an audio system which provides a sound in response to vital signs of the patient.

5. The system of claim 1 further comprising:
   a defibrillator for providing circulatory resuscitation to the patient and/or a ventilator for providing respiratory resuscitation to the patient, and wherein the defibrillator and/or the ventilator and the communication system have separate circuits with conductive lines that permit the at least two of the communication system to be in communication with the defibrillator and/or the ventilator.

6. The system of claim 5, further including a monitor for monitoring vital signs of the patient.

7. The system of claim 6, wherein the monitor displays the vital signs of the patient.

8. The system of claim 6, wherein the operation of the defibrillator, ventilator, and/or monitor is controllable in response to the vital signs being send to an external communication system.

9. The system of claim 5, wherein the defibrillator and/or ventilator is controllable in response to one or more protocol procedures for providing life support to the patient and wherein the one or more protocol procedures are adjustable in response to a signal flowing between the communication system and the external communication system.

10. The system of claim 5, wherein the ventilator provides oxygen to the patient in response to an indication from the defibrillator that the patient is in asystole.

11. A communication system for providing emergency life support, comprising:
   dual communication links, defined as primary communication and secondary communication links, each of the primary and secondary communication links having a transmitter and a receiver for sending and receiving voice and/or data information to separate external communication systems, and the primary communication link having the means for controlling the secondary communication link such that the primary communication link in communication to a first external communication system can control the secondary communication link to initiate contact to a second external communication system.

12. The system of claim 11, further including a global positioning system for providing a location of the system.

13. The system of claim 11, wherein the communication system includes a phone.

14. The system of claim 11 further comprising:
   a defibrillator for providing circulatory resuscitation to a patient and/or a ventilator for providing respiratory resuscitation to a patient, and wherein a communication system being removably attached to either the defibrillator and/or the ventilator, the communication system the defibrillator and/or the ventilator and the communication system have separate circuits with conductive lines that permit the at least two of the communication system to be in communication with the defibrillator and/or the ventilator.

15. The system of claim 14, further including a monitor for monitoring vital signs of the patient.

16. The system of claim 15, wherein the monitor displays the vital signs of the patient.

17. The system of claim 15, wherein the operation of the defibrillator, ventilator, and/or monitor is controllable in response to the vital signs being send to an external communication system.

18. The system of claim 14, wherein the defibrillator and/or ventilator is controllable in response to one or more protocol procedures for providing life support to the patient and wherein the one or more protocol procedures are adjustable in response to a signal flowing between the communication system and the external communication system.

19. The system of claim 14, wherein the data information includes data information obtained from the defibrillator and/or ventilator.

* * * * *